US010364275B2

(12) United States Patent
Miller et al.

(10) Patent No.: US 10,364,275 B2
(45) Date of Patent: Jul. 30, 2019

(54) METHODS FOR TREATING INFLAMMATORY RESPONSES OR DISEASES CAUSED BY INFLAMMATION USING APOA-I BINDING PROTEIN (APOA1BP)

(71) Applicant: THE REGENTS OF THE UNIVERSITY OF CALIFORNIA, Oakland, CA (US)

(72) Inventors: Yury Miller, La Jolla, CA (US); Longhou Fang, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 161 days.

(21) Appl. No.: 14/894,281

(22) PCT Filed: May 27, 2014

(86) PCT No.: PCT/US2014/039549
§ 371 (c)(1),
(2) Date: Nov. 25, 2015

(87) PCT Pub. No.: WO2014/193822
PCT Pub. Date: Dec. 4, 2014

(65) Prior Publication Data
US 2016/0115211 A1    Apr. 28, 2016

Related U.S. Application Data

(60) Provisional application No. 61/827,729, filed on May 27, 2013.

(51) Int. Cl.
| | | |
|---|---|---|
| A61K 38/17 | (2006.01) | |
| A61P 29/00 | (2006.01) | |
| C07K 14/47 | (2006.01) | |
| C12N 15/113 | (2010.01) | |
| C07K 16/18 | (2006.01) | |
| A61P 3/06 | (2006.01) | |
| A61K 38/00 | (2006.01) | |

(52) U.S. Cl.
CPC .......... *C07K 14/47* (2013.01); *A61K 38/1709* (2013.01); *A61K 38/1761* (2013.01); *A61P 29/00* (2018.01); *C07K 16/18* (2013.01); *C12N 15/113* (2013.01); *A61K 38/00* (2013.01); *A61P 3/06* (2018.01); *C07K 14/4702* (2013.01); *C07K 2317/76* (2013.01); *C12N 2310/11* (2013.01); *C12N 2310/111* (2013.01); *C12N 2310/14* (2013.01); *C12N 2310/3233* (2013.01)

(58) Field of Classification Search
None
See application file for complete search history.

(56) References Cited

U.S. PATENT DOCUMENTS

2012/0252744 A1    10/2012  Li et al.

FOREIGN PATENT DOCUMENTS

WO    2012019060 A1    2/2012

OTHER PUBLICATIONS

Fang et al (2013. Nature. 498(7452): 118-122).*
Proudfoot, 2011. Dis Model Mech. 4(2): 145-153; 19 pages as printed to pdf.*
Jha et al, "Biochemical and Structural Characterization of Apolipoprotein A-I Binding Protein, a Novel Phosphoprotein with a Potential Role in Sperm Capacitation" Endocrinology, May 2008, v 149, n 5, pp. 2108-2120.
Boisvert et al., "Biochemical and Structural Characterization of Apolipoprotein A-I Binding Protein, a Novel Phosphoprotein with a Potential Role in Sperm Capacitation" Arterioscler Thromb Vasc Biol., 1999; v 19; pp. 525-530.
Gao et al., "L-5F, an apolipoprotein A-I mimetic, inhibits tumor angiogenesis by suppressing VEGF/basic FGF signaling pathways" Integr Biol (Camb), Apr. 2011; v 3, n 4: pp. 479-489.
Fang et al., "Control of Angiogenesis by AIBP-mediated Cholesterol Efflux" Nature, Jun. 6, 2013, v 498, pp. 118-122.
Young, International Search Report and Written Opinion for PCT/US2014/039549, dated Oct. 10, 2014.
Nickitas-Etienne, International Preliminary Report on Patentability for PCT/US2014/039549, dated Dec. 1, 2015.

* cited by examiner

Primary Examiner — Zachary C Howard
(74) Attorney, Agent, or Firm — Greer, Burns & Crain, LTD.; Gregory P. Einhorn

(57) ABSTRACT

The invention provides pharmaceutical compounds and formulations comprising nucleic acids and polypeptides for regulating (including upregulating or inhibiting) the expression of ApoA-1 Binding Protein (APOAIBP, AIBP, or AI-BP) and methods for making and using them. In alternative embodiments, APOAIBP-inhibiting pharmaceutical compositions and formulations of the invention are administered to an individual in need thereof in an amount sufficient to stimulate tissue revascularizaton, e.g., supporting or stimulating revascularization of heart tissue, e.g., after a cardiac ischemia. In alternative embodiments, pharmaceutical compositions and formulations of the invention that comprise APOAIBP nucleic acids and polypeptides or result in an increase in expression or activity of APOAIBP nucleic acids and polypeptides are administered to an individual in need thereof in an amount sufficient to treat, prevent, reverse and/or ameliorate a dyslipidemia, e.g., to treat, prevent, reverse and/or ameliorate conditions responsive to increasing cholesterol efflux from cells, including cardiovascular disease and atherosclerosis.

10 Claims, 49 Drawing Sheets
(26 of 49 Drawing Sheet(s) Filed in Color)
Specification includes a Sequence Listing.

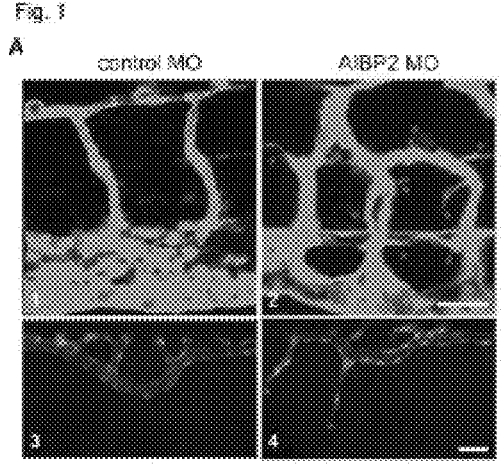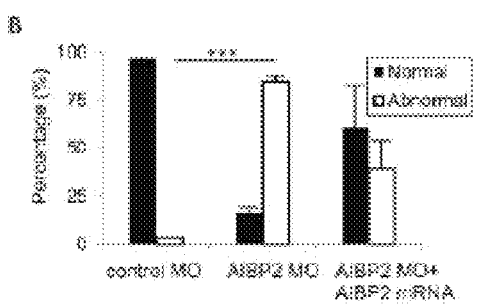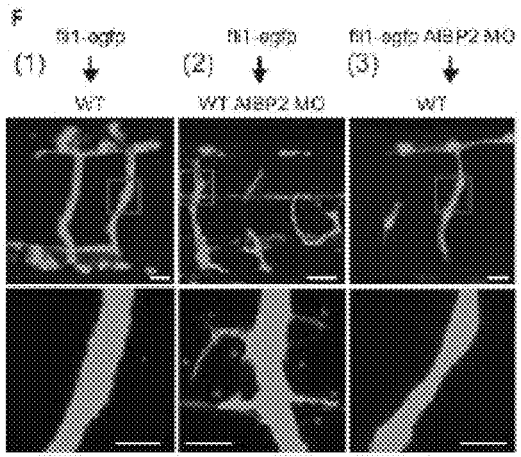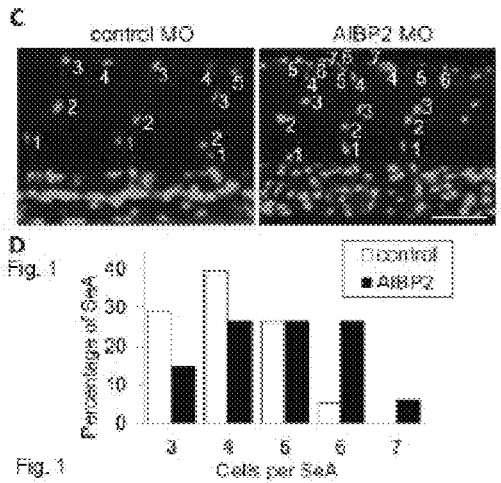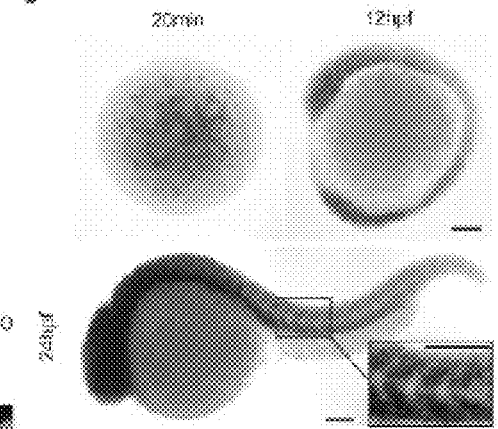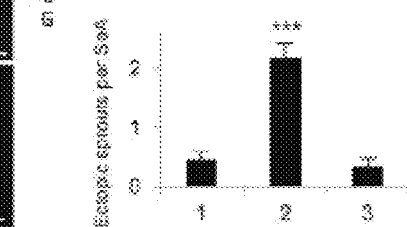

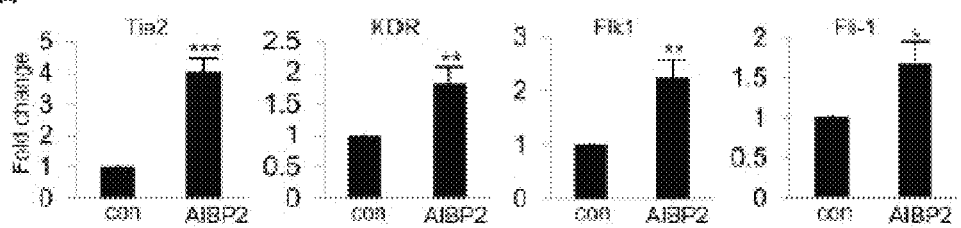
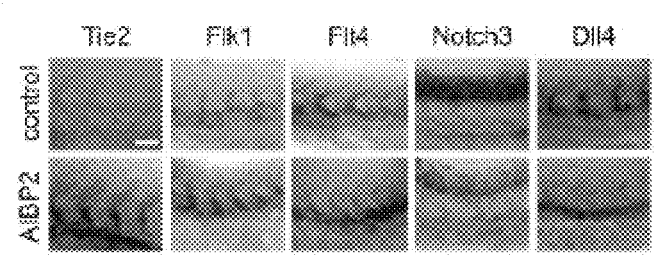
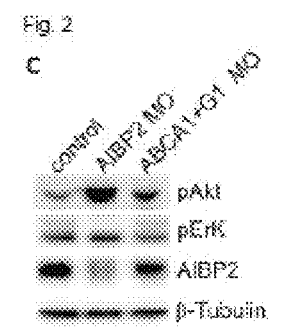
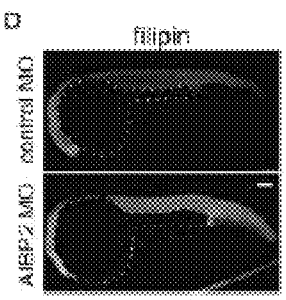
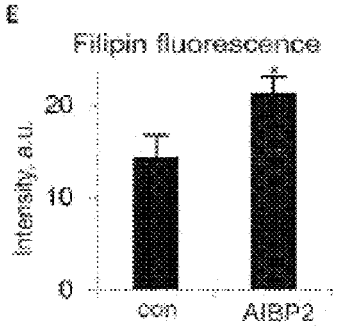
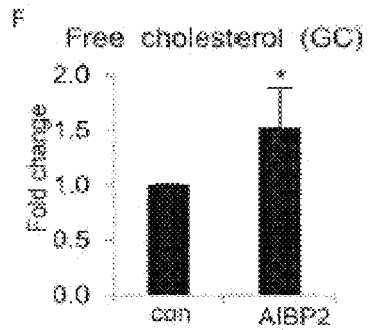

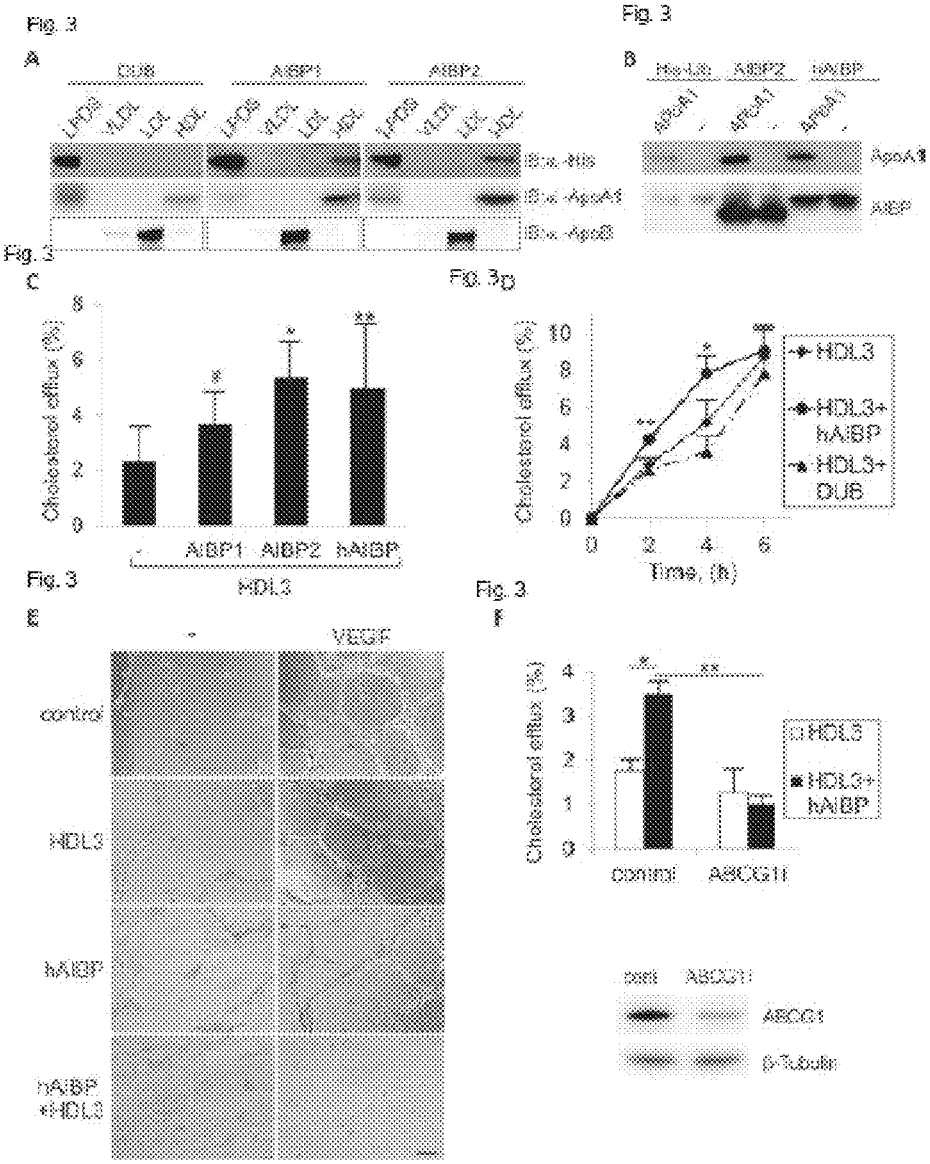

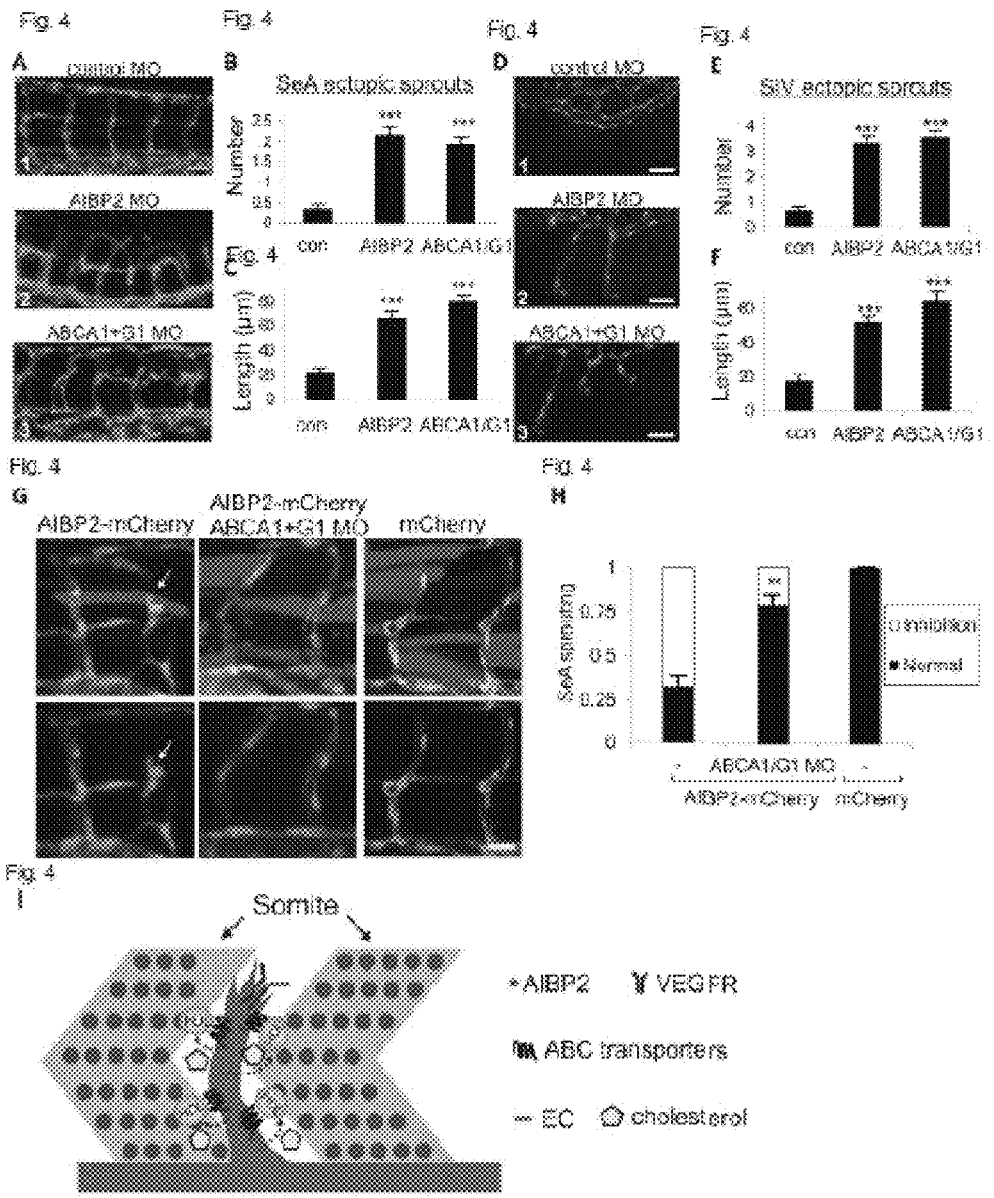

Consensus: 56.1%
Identity: 40.0%

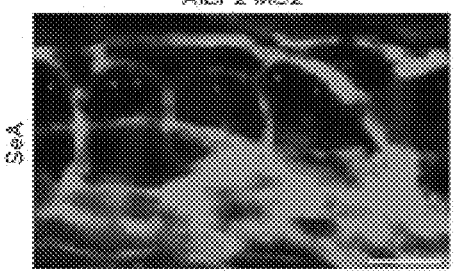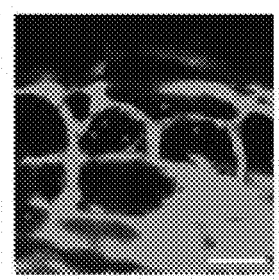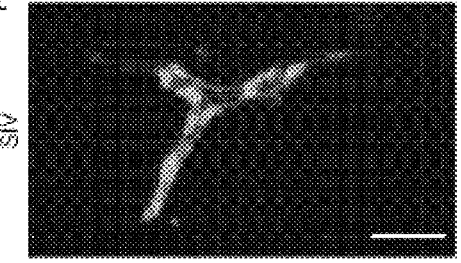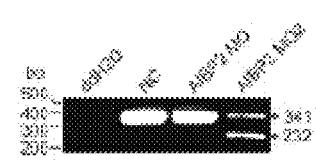

FIG. 8

| GO term | p-value |
|---|---|
| anatomical structure development | 4.3E-07 |
| anatomical structure morphogenesis | 6.4E-07 |
| cell differentiation | 1.4E-06 |
| cellular developmental process | 4.4E-06 |
| nucleotide binding | 6.3E-06 |
| localization of cell | 8.4E-06 |
| cellular component organization | 9.5E-06 |
| DNA-dependent DNA replication | 1.6E-05 |
| cell migration | 1.7E-05 |

| Gene | Full name | Synonyms | AIBP2 morphant/control |
|---|---|---|---|
| mcm5 | minichromosome maintenance deficient 5 (S. cerevisiae) | | 5.2 |
| mcm4 | minichromosome maintenance deficient 4, mitotin (S. cerevisiae) | | 4.3 |
| mcm3 | minichromosome maintenance deficient 3 (S. cerevisiae) | | 3.3 |
| met | met proto-oncogene (hepatocyte growth factor receptor) | c-met | 2.6 |
| tie2 | endothelium-specific receptor tyrosine kinase 2 | | 2.4 |
| pak1 | p21/Cdc42/Rac1-activated kinase 1 | | 2.1 |
| fgfr1 | fibroblast growth factor receptor 1 | bFGFR-1A | 1.9 |
| ephb4a | eph receptor B4a | ntk5 | 1.6 |
| flt4 | fms-related tyrosine kinase 4 | VEGFR-3 | 1.3 |
| kdr | kinase insert domain receptor | VEGFR-2 | 1.3 |

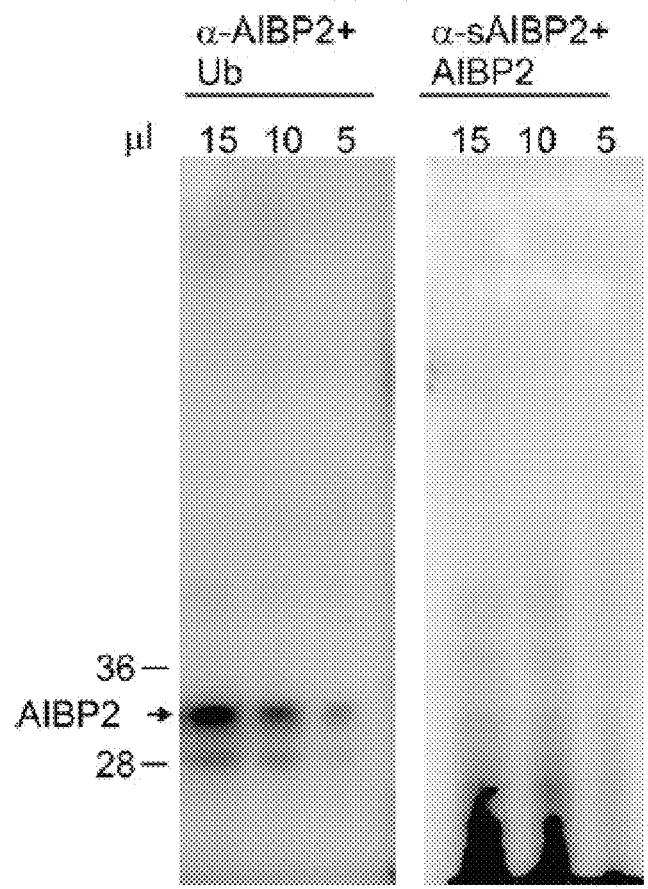
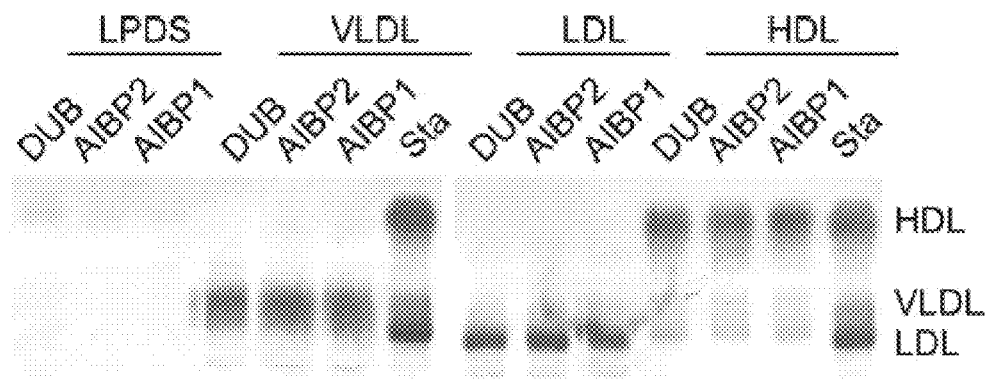

control

AIBP2

ABCA1/G1

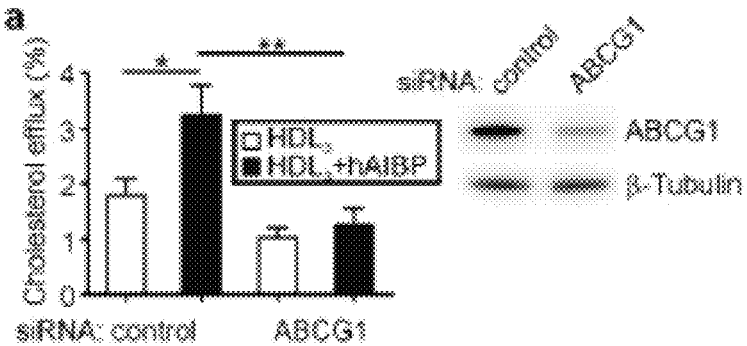
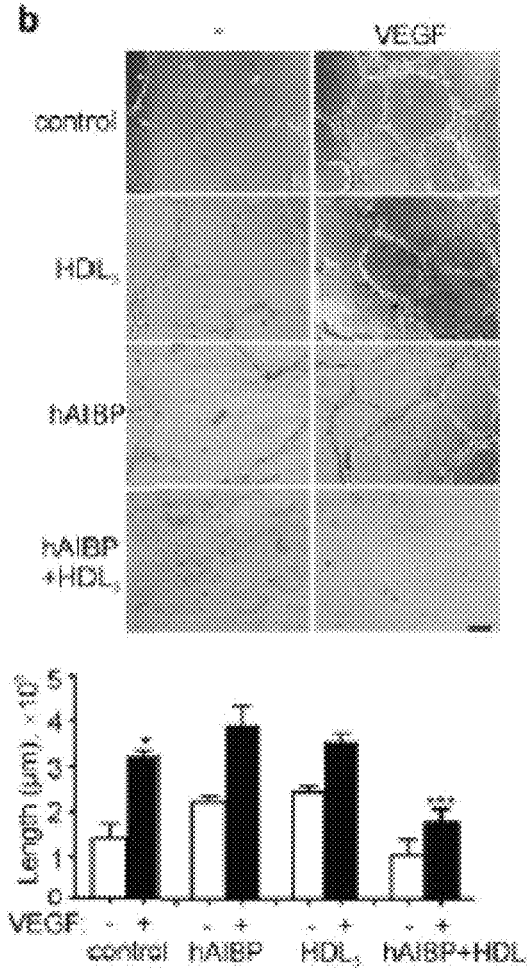
Fig. 12

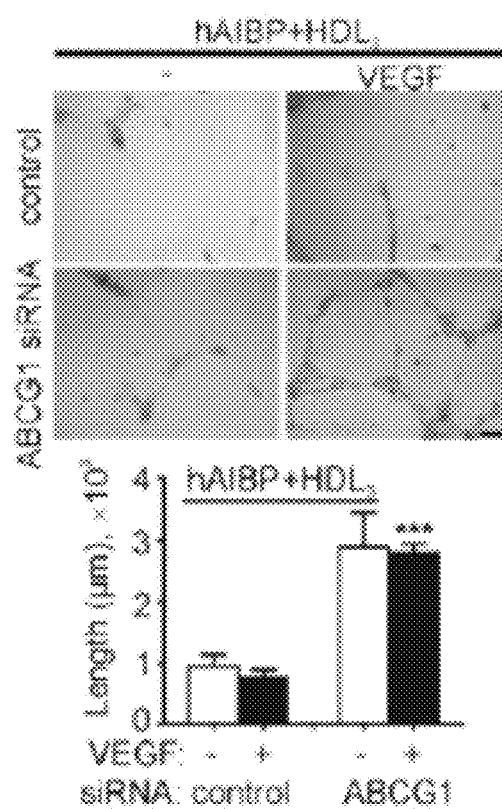

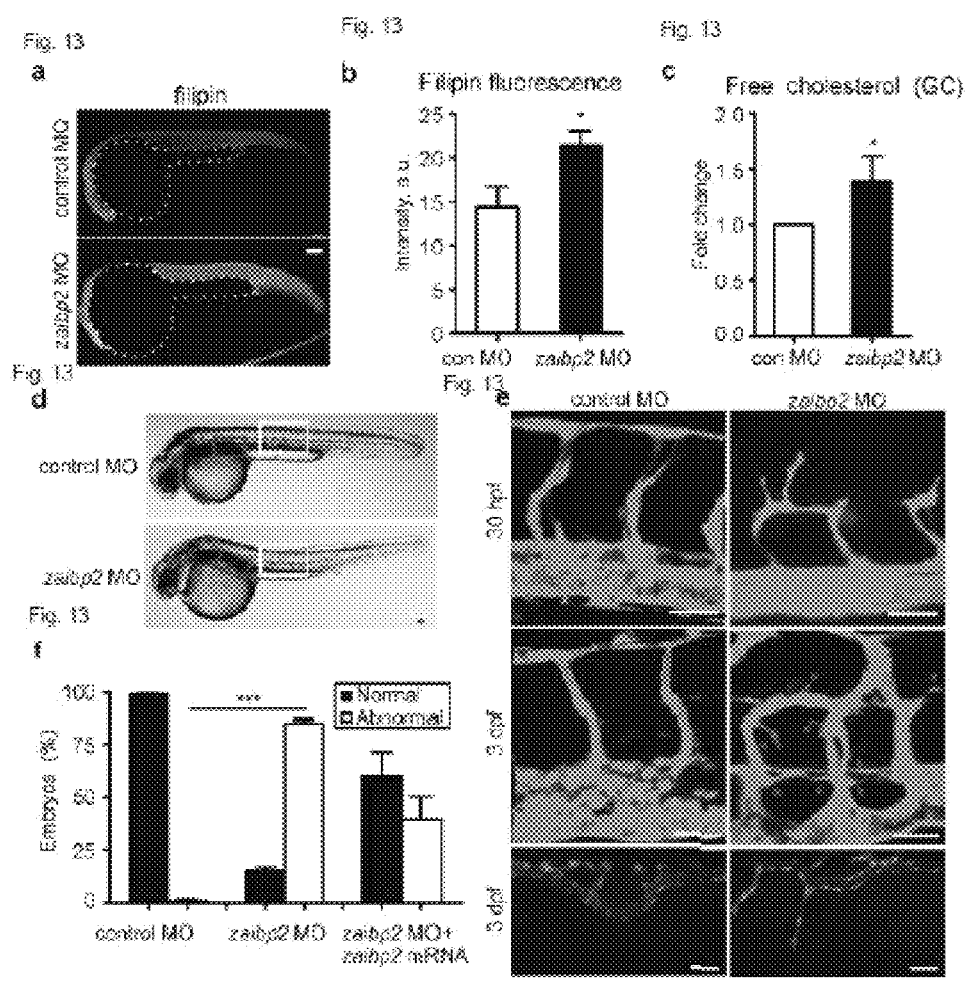

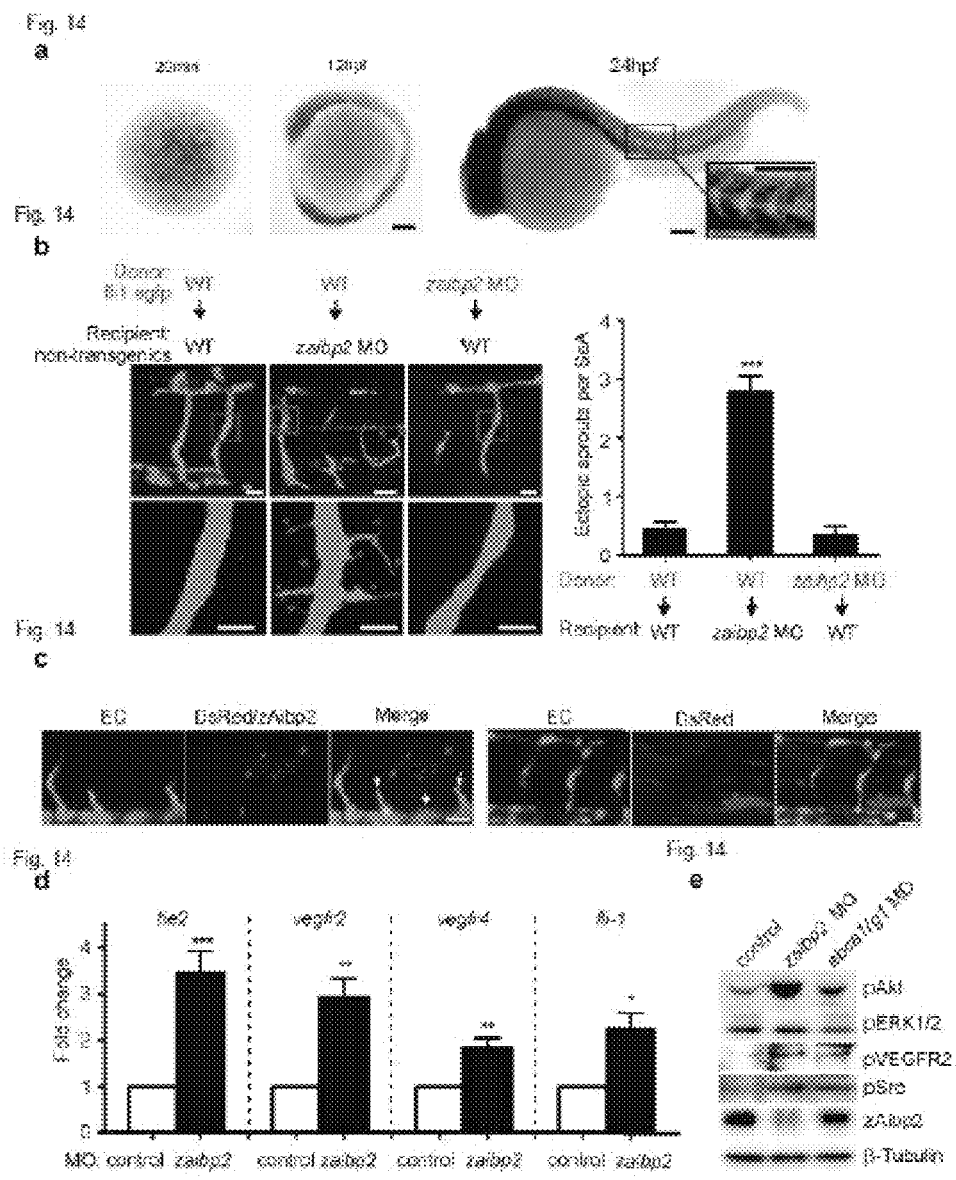

Fig. 15
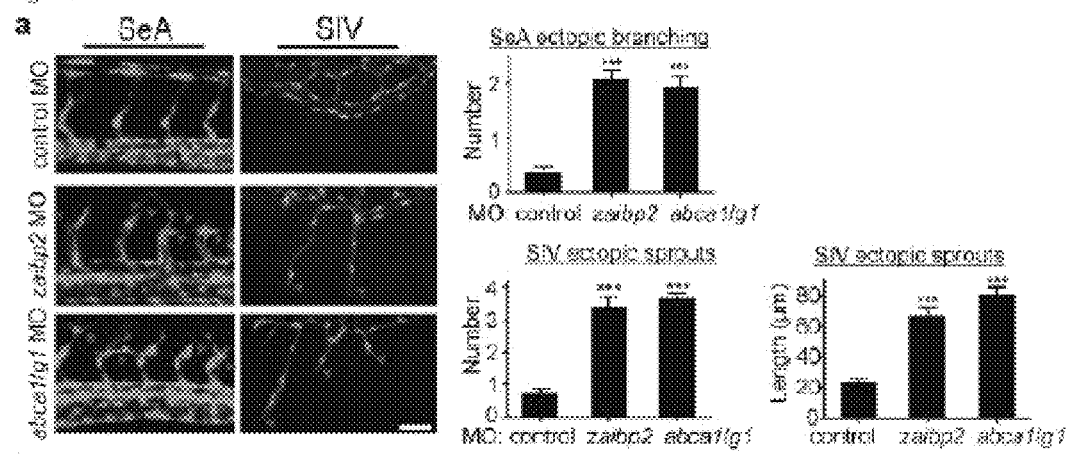
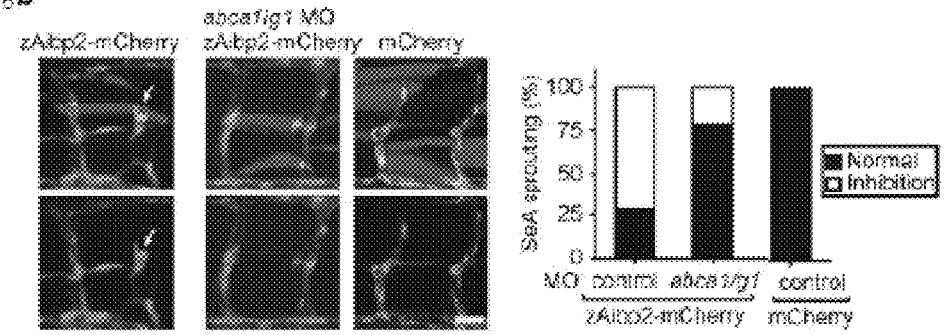

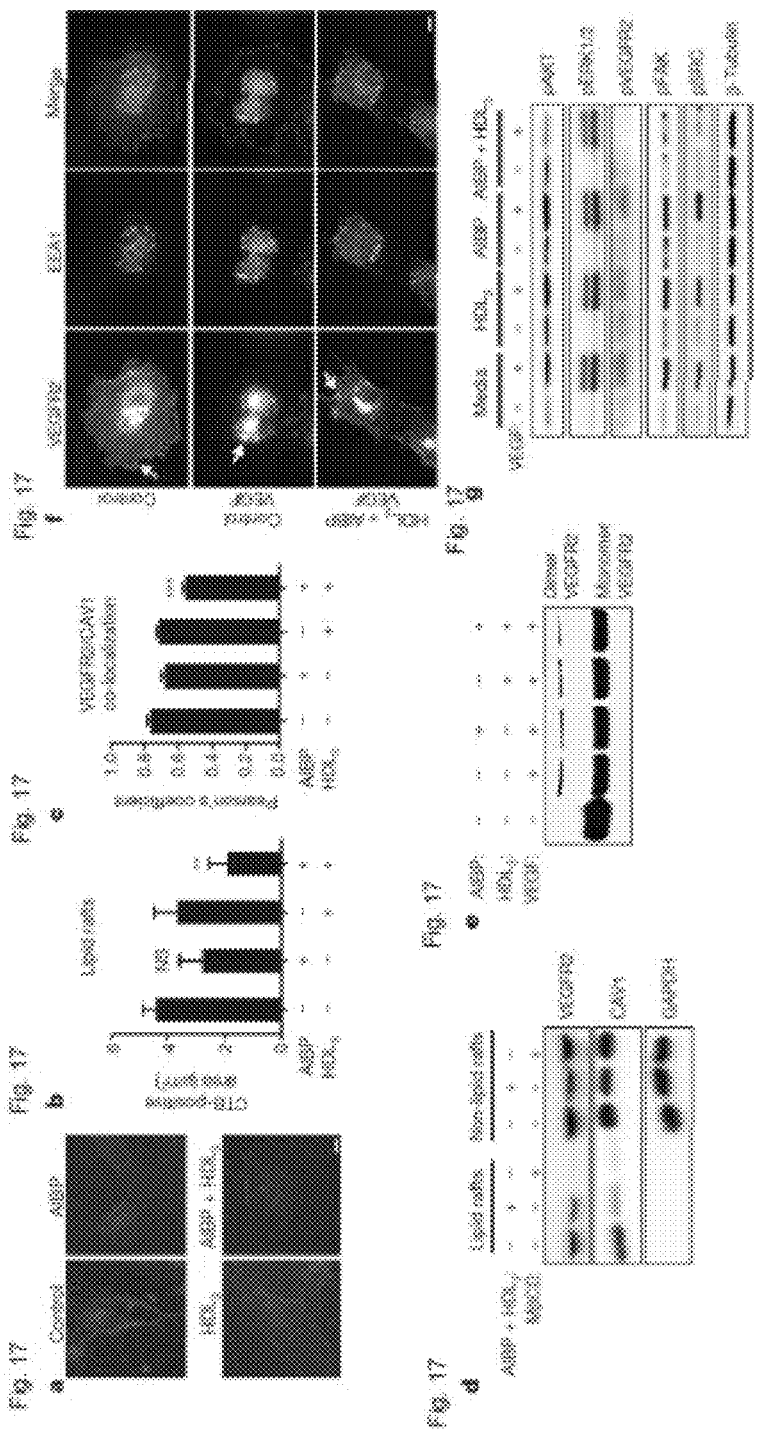

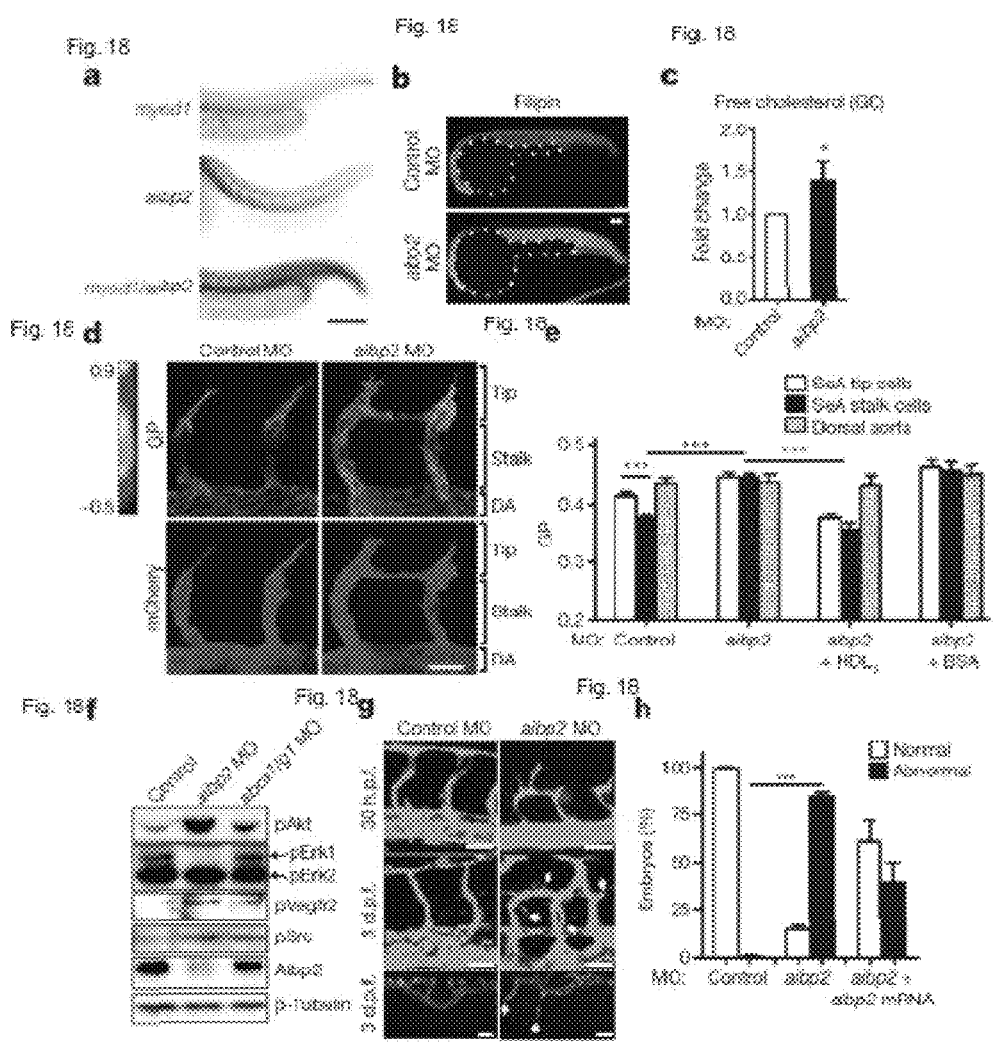

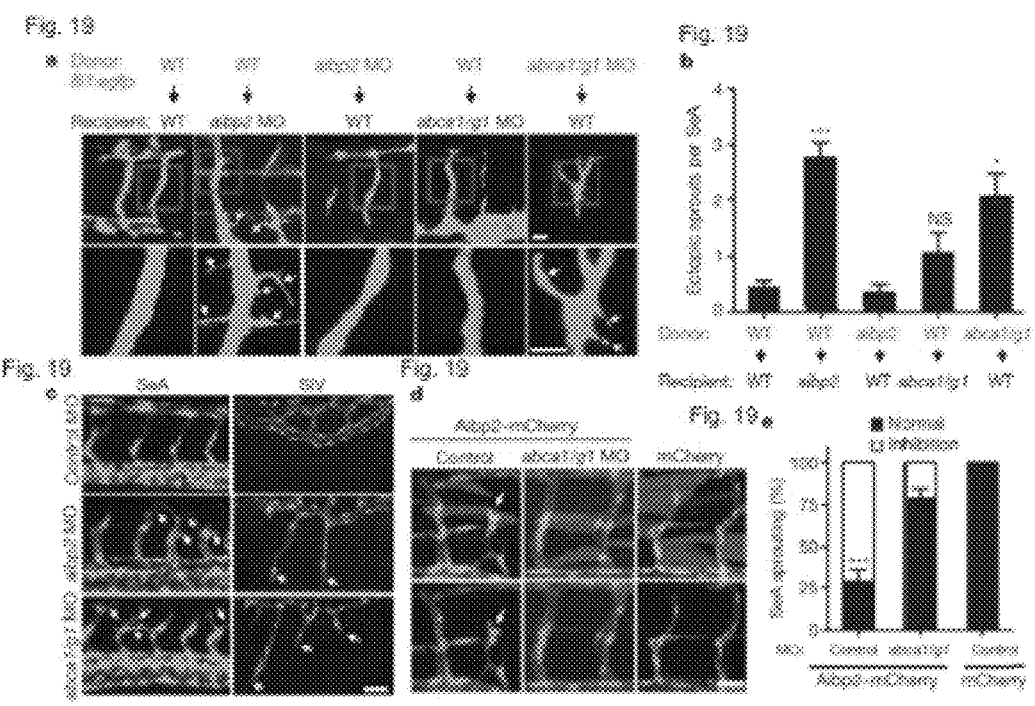

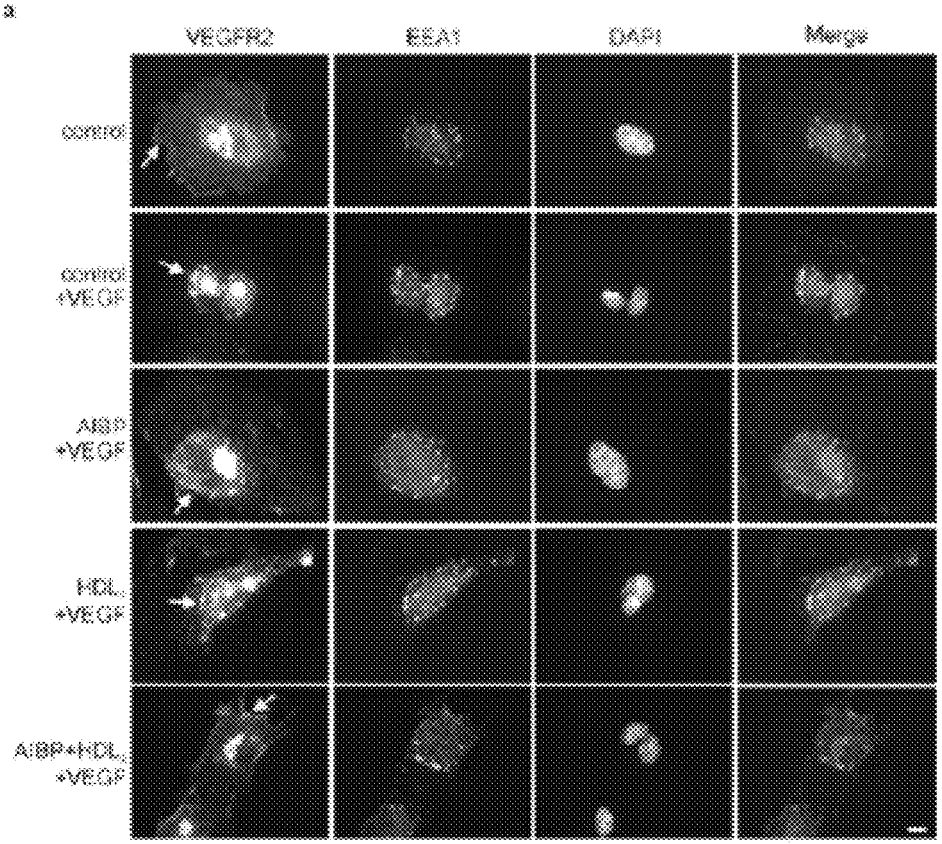
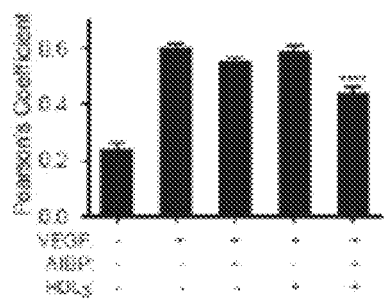

Fig. 28
a
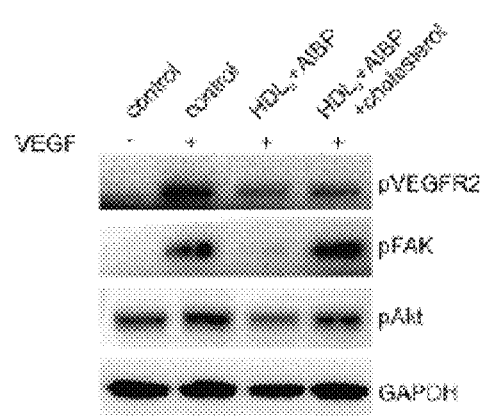
Fig. 28
b
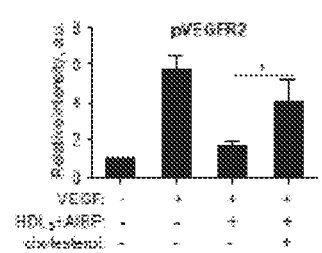 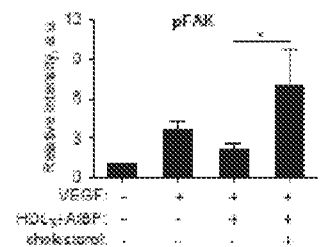 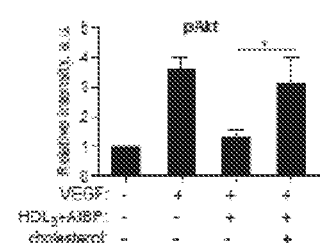

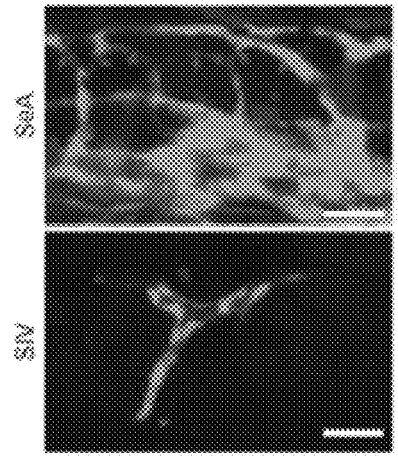
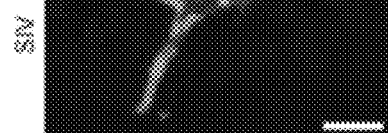
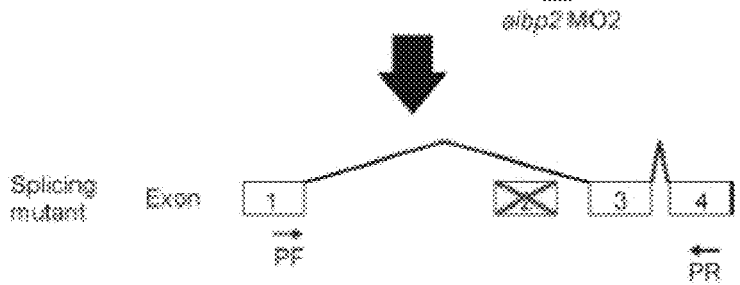
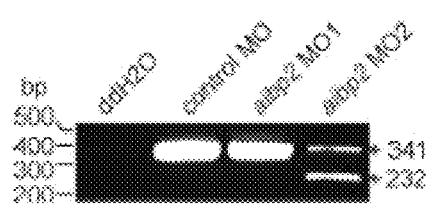

FIG. 38A
Abcg1-mCherry
+control MO
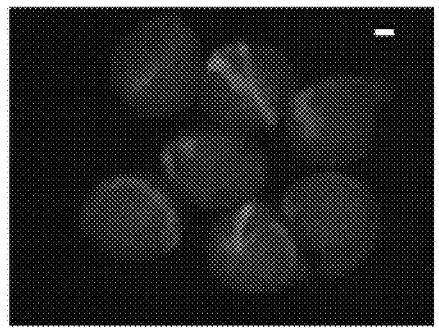
Abcg1-mCherry
+*abcg1* MO
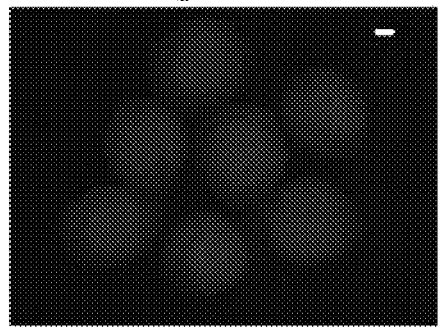
FIG. 38B
Abca1a-mCherry
+control MO
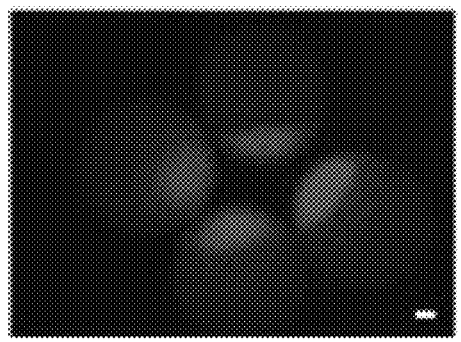
Abca1a-mCherry
+*abca1a* MO
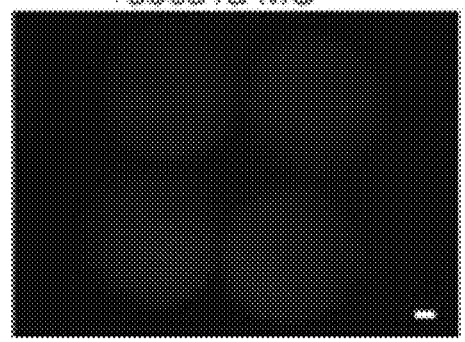

SEQUENCE LISTING

```
<160> NUMBER OF SEQ ID NOS: 47

<210> SEQ ID NO 1
<211> LENGTH: 25
<212> TYPE: DNA
<213> ORGANISM: artificial sequence
<220> FEATURE:
```

<223> OTHER INFORMATION: synthetic oligonucleotide

<400> SEQUENCE: 1
tgagcttcat gttcatttat tccgc                                              25

<210> SEQ ID NO 2
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 2
tgtggttcat cttgatttat tcggc                                              25

<210> SEQ ID NO 3
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 3
tgttgagtgt cagacaaacc ttggt                                              25

<210> SEQ ID NO 4
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 4
tctgtattca aatcagacgc tcagt                                              25

<210> SEQ ID NO 5
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 5
aacccaactg agtggagaca gccat                                              25

<210> SEQ ID NO 6
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 6
aaaaggctgc catgagacat gccat                                              25

<210> SEQ ID NO 7
<211> LENGTH: 31
<212> TYPE: DNA
<213> ORGANISM: artificial sequence
<220> FEATURE:
<223> OTHER INFORMATION: synthetic oligonucleotide

<400> SEQUENCE: 7
ccggaattcc atgttggggg ttcgagctct g                                       31

<210> SEQ ID NO 8
<211> LENGTH: 33
<212> TYPE: DNA
<213> ORGANISM: artificial sequence
<220> FEATURE:
<223> OTHER INFORMATION: synthetic oligonucleotide

<400> SEQUENCE: 8
cgcggatcct cagttgagct gaaacacaca ctc                                33

<210> SEQ ID NO 9
<211> LENGTH: 35
<212> TYPE: DNA
<213> ORGANISM: artificial sequence
<220> FEATURE:
<223> OTHER INFORMATION: synthetic oligonucleotide

<400> SEQUENCE: 9
ccggaattcc gccaccatga accacagctc caacg                              35

<210> SEQ ID NO 10
<211> LENGTH: 34
<212> TYPE: DNA
<213> ORGANISM: artificial sequence
<220> FEATURE:
<223> OTHER INFORMATION: synthetic oligonucleotide

<400> SEQUENCE: 10
cgcggatccc gcagttctat aatacattct gtgc                               34

<210> SEQ ID NO 11
<211> LENGTH: 40
<212> TYPE: DNA
<213> ORGANISM: artificial sequence
<220> FEATURE:
<223> OTHER INFORMATION: synthetic oligonucleotide

<400> SEQUENCE: 11
cggaattcca tgtccaggct gcgggcgctg ctgggcctcg                         40

<210> SEQ ID NO 12
<211> LENGTH: 33
<212> TYPE: DNA
<213> ORGANISM: artificial sequence
<220> FEATURE:
<223> OTHER INFORMATION: synthetic oligonucleotide

<400> SEQUENCE: 12
cggggtacct cactgcagac gatagacaca ctc                                33

<210> SEQ ID NO 13
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 13
cttggcacgt tgccttgata ag                                            22

<210> SEQ ID NO 14
<211> LENGTH: 23
<212> TYPE: DNA
<213> ORGANISM: artificial sequence
<220> FEATURE:
<223> OTHER INFORMATION: synthetic oligonucleotide -continued

<400> SEQUENCE: 14
ccttcatatc tgagagtgat ccc                                    23

<210> SEQ ID NO 15
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 15
tccacgaggg tgggcagtca                                        20

<210> SEQ ID NO 16
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 16
agacgggtgg tgtggagtaa cga                                    23

<210> SEQ ID NO 17
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 17
gcgatggatg gcaatagagt                                        20

<210> SEQ ID NO 18
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 18
cgacagcagg atctgagaga                                        20

<210> SEQ ID NO 19
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 19
tgcccacatg gagctgctag ca                                     22

<210> SEQ ID NO 20
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 20
tgtggcacat tcaaccacat gagc                                   24

<210> SEQ ID NO 21
<211> LENGTH: 31

```
<212> TYPE: DNA
<213> ORGANISM: artificial sequence
<220> FEATURE:
<223> OTHER INFORMATION: synthetic oligonucleotide

<400> SEQUENCE: 21
ccggaattcc atgttggggg ttcgagctct g                            31

<210> SEQ ID NO 22
<211> LENGTH: 33
<212> TYPE: DNA
<213> ORGANISM: artificial sequence
<220> FEATURE:
<223> OTHER INFORMATION: synthetic oligonucleotide

<400> SEQUENCE: 22
cgcggatcct cagttgagct gaaacacaca ctc                          33

<210> SEQ ID NO 23
<211> LENGTH: 35
<212> TYPE: DNA
<213> ORGANISM: artificial sequence
<220> FEATURE:
<223> OTHER INFORMATION: synthetic oligonucleotide

<400> SEQUENCE: 23
ccggaattcc gccaccatga accacagctc caacg                        35

<210> SEQ ID NO 24
<211> LENGTH: 34
<212> TYPE: DNA
<213> ORGANISM: artificial sequence
<220> FEATURE:
<223> OTHER INFORMATION: synthetic oligonucleotide

<400> SEQUENCE: 24
cgcggatccc gcagttctat aatacattct gtgc                         34

<210> SEQ ID NO 25
<211> LENGTH: 41
<212> TYPE: DNA
<213> ORGANISM: artificial sequence
<220> FEATURE:
<223> OTHER INFORMATION: synthetic oligonucleotide

<400> SEQUENCE: 25
ccggaattcc atgtccaggc tgcgggcgct gctgggcctc g                 41

<210> SEQ ID NO 26
<211> LENGTH: 33
<212> TYPE: DNA
<213> ORGANISM: artificial sequence
<220> FEATURE:
<223> OTHER INFORMATION: synthetic oligonucleotide

<400> SEQUENCE: 26
cggggtacct cactgcagac gatagacaca ctc                          33

<210> SEQ ID NO 27
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 27
```
tgagcttcat gttcatttat tccgc                                          25

<210> SEQ ID NO 28
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 28
tgtggttcat cttgatttat tcggc                                          25

<210> SEQ ID NO 29
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 29
tgttgagtgt cagacaaacc ttggt                                          25

<210> SEQ ID NO 30
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 30
tctgtattca aatcagacgc tcagt                                          25

<210> SEQ ID NO 31
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 31
aacccaactg agtggagaca gccat                                          25

<210> SEQ ID NO 32
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 32
aaaaggctgc catgagacat gccat                                          25

<210> SEQ ID NO 33
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 33
cttggcacgt tgccttgata ag                                             22

<210> SEQ ID NO 34
<211> LENGTH: 23
<212> TYPE: DNA
<213> ORGANISM: artificial sequence

```
<220> FEATURE:
<223> OTHER INFORMATION: synthetic oligonucleotide

<400> SEQUENCE: 34
ccttcatatc tgagagtgat ccc                                              23

<210> SEQ ID NO 35
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 35
gcgatggatg gcaatagagt                                                  20

<210> SEQ ID NO 36
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 36
cgacagcagg atctgagaga                                                  20

<210> SEQ ID NO 37
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 37
tccacgaggg tgggcagtca                                                  20

<210> SEQ ID NO 38
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 38
agacgggtgg tgtggagtaa cga                                              23

<210> SEQ ID NO 39
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 39
tgcccacatg gagctgctag ca                                               22

<210> SEQ ID NO 40
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 40
tgtggcacat tcaaccacat gagc                                             24
```

<210> SEQ ID NO 41
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 41
ctcttccagc cttccttcct                                                    20

<210> SEQ ID NO 42
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 42
ggttggttcg ttcgtttgaa t                                                  21

<210> SEQ ID NO 43
<211> LENGTH: 288
<212> TYPE: PRT
<213> ORGANISM: Homo sapiens

<400> SEQUENCE: 43

Met Ser Arg Leu Arg Ala Leu Leu Gly Leu Gly Leu Leu Val Ala Gly
1               5                   10                  15

Ser Arg Leu Pro Arg Ile Lys Ser Gln Thr Ile Ala Cys Arg Ser Gly
            20                  25                  30

Pro Thr Trp Trp Gly Pro Gln Arg Leu Asn Ser Gly Gly Arg Trp Asp
        35                  40                  45

Ser Glu Val Met Ala Ser Thr Val Val Lys Tyr Leu Ser Gln Glu Glu
    50                  55                  60

Ala Gln Ala Val Asp Gln Glu Leu Phe Asn Glu Tyr Gln Phe Ser Val
65                  70                  75                  80

Asp Gln Leu Met Glu Leu Ala Gly Leu Ser Cys Ala Thr Ala Ile Ala
                85                  90                  95

Lys Ala Tyr Pro Pro Thr Ser Met Ser Arg Ser Pro Thr Val Leu
            100                 105                 110

Val Ile Cys Gly Pro Gly Asn Asn Gly Gly Asp Gly Leu Val Cys Ala
        115                 120                 125

Arg His Leu Lys Leu Phe Gly Tyr Glu Pro Thr Ile Tyr Tyr Pro Lys
    130                 135                 140

Arg Pro Asn Lys Pro Leu Phe Thr Ala Leu Val Thr Gln Cys Gln Lys
145                 150                 155                 160

Met Asp Ile Pro Phe Leu Gly Glu Met Pro Ala Glu Pro Met Thr Ile
                165                 170                 175

Asp Glu Leu Tyr Glu Leu Val Val Asp Ala Ile Phe Gly Phe Ser Phe
            180                 185                 190

Lys Gly Asp Val Arg Glu Pro Phe His Ser Ile Leu Ser Val Leu Lys
        195                 200                 205

Gly Leu Thr Val Pro Ile Ala Ser Ile Asp Ile Pro Ser Gly Trp Asp
    210                 215                 220

Val Glu Lys Gly Asn Ala Gly Gly Ile Gln Pro Asp Leu Leu Ile Ser
225                 230                 235                 240

Leu Thr Ala Pro Lys Lys Ser Ala Thr Gln Phe Thr Gly Arg Tyr His
                245                 250                 255

```
Tyr Leu Gly Gly Arg Phe Val Pro Pro Ala Leu Glu Lys Lys Tyr Gln
            260                 265                 270

Leu Asn Leu Pro Pro Tyr Pro Asp Thr Glu Cys Val Tyr Arg Leu Gln
            275                 280                 285
```

<210> SEQ ID NO 44
<211> LENGTH: 282
<212> TYPE: PRT
<213> ORGANISM: Mus musculus

<400> SEQUENCE: 44

```
Met Ser Gly Leu Arg Thr Leu Gly Leu Gly Leu Leu Val Ala Gly
1               5                   10                  15

Ser Arg Leu Pro Arg Val Ile Ser Gln Gln Ser Val Cys Arg Ala Arg
            20                  25                  30

Pro Ile Trp Trp Gly Thr Gln Arg Gly Ser Glu Thr Met Ala Gly
            35                  40                  45

Ala Ala Val Lys Tyr Leu Ser Gln Glu Ala Gln Ala Val Asp Gln
        50                  55                  60

Glu Leu Phe Asn Glu Tyr Gln Phe Ser Val Asp Gln Leu Met Glu Leu
65                  70                  75                  80

Ala Gly Leu Ser Cys Ala Thr Ala Ile Ala Lys Ala Tyr Pro Pro Thr
                85                  90                  95

Ser Met Ser Lys Ser Pro Pro Thr Val Leu Val Ile Cys Gly Pro Gly
            100                 105                 110

Asn Asn Gly Gly Asp Gly Leu Val Cys Ala Arg His Leu Lys Leu Phe
            115                 120                 125

Gly Tyr Gln Pro Thr Ile Tyr Tyr Pro Lys Arg Pro Asn Lys Pro Leu
        130                 135                 140

Phe Thr Gly Leu Val Thr Gln Cys Gln Lys Met Asp Ile Pro Phe Leu
145                 150                 155                 160

Gly Glu Met Pro Pro Glu Pro Met Met Val Asp Glu Leu Tyr Glu Leu
                165                 170                 175

Val Val Asp Ala Ile Phe Gly Phe Ser Phe Lys Gly Asp Val Arg Glu
            180                 185                 190

Pro Phe His Ser Ile Leu Ser Val Leu Ser Gly Leu Thr Val Pro Ile
            195                 200                 205

Ala Ser Ile Asp Ile Pro Ser Gly Trp Asp Val Glu Lys Gly Asn Pro
        210                 215                 220

Ser Gly Ile Gln Pro Asp Leu Leu Ile Ser Leu Thr Ala Pro Lys Lys
225                 230                 235                 240

Ser Ala Thr His Phe Thr Gly Arg Tyr His Tyr Leu Gly Gly Arg Phe
                245                 250                 255

Val Pro Pro Ala Leu Glu Lys Lys Tyr Gln Leu Asn Leu Pro Ser Tyr
            260                 265                 270

Pro Asp Thr Glu Cys Val Tyr Arg Leu Gln
            275                 280
```

<210> SEQ ID NO 45
<211> LENGTH: 283
<212> TYPE: PRT
<213> ORGANISM: Danio rerio

<400> SEQUENCE: 45

```
Met Leu Gly Val Arg Ala Leu Phe Gly Ile Gly Leu Leu Val Thr Ser
1               5                   10                  15
```

Arg Gly Gly Phe Val Leu Thr His Thr Arg Ala Cys Ser Ser Ala Ala
            20                  25                  30

Ser Asn Ile Tyr Ser Lys His Leu Thr His Arg Pro Thr Cys Thr Met
        35                  40                  45

Ala Asn Thr Gly Val Lys Tyr Leu Gly Gln Glu Ala Gln Gln Ile
    50                  55                  60

Asp Glu Glu Leu Phe Ser Asp Phe Ser Phe Ser Val Asp Gln Leu Met
65                  70                  75                  80

Glu Leu Ala Gly Leu Ser Cys Ala Thr Ala Val Ala Lys Gly Tyr Pro
                85                  90                  95

Val Thr Ser Leu Leu Lys Ser Pro Ala Arg Val Leu Val Ile Cys Gly
            100                 105                 110

Pro Gly Asn Asn Gly Gly Asp Gly Leu Val Cys Ala Arg His Leu Lys
            115                 120                 125

Leu Phe Gly Tyr Glu Pro Ser Val Leu Tyr Pro Lys Arg Pro Asn Lys
    130                 135                 140

Gln Leu Phe Gln Asn Leu Ser Ile Gln Cys Gln Lys Met Glu Ile Pro
145                 150                 155                 160

Phe Leu Thr Glu Met Pro Glu Ala Asp Leu Ile Asp Glu Ala Tyr Ser
                165                 170                 175

Leu Val Val Asp Ala Ile Phe Gly Phe Ser Phe Lys Gly Ala Val Arg
            180                 185                 190

Glu Pro Phe Gly Glu Ile Leu Ser Gln Leu Lys Lys Ile Thr Val Pro
    195                 200                 205

Ile Ala Ser Val Asp Ile Pro Ser Gly Trp Asp Val Glu Lys Gly Cys
210                 215                 220

Pro Asp Gly Ile Gln Pro Asp Met Leu Ile Ser Leu Thr Ala Pro Lys
225                 230                 235                 240

Lys Ser Ala Ala Leu Phe Lys Gly Arg Phe His Phe Leu Gly Gly Arg
                245                 250                 255

Phe Val Pro Pro Val Leu Glu Gln Lys Tyr Gln Leu Asn Leu Pro Gln
            260                 265                 270

Tyr Pro Gly Thr Glu Cys Val Phe Gln Leu Asn
        275                 280

<210> SEQ ID NO 46
<211> LENGTH: 275
<212> TYPE: PRT
<213> ORGANISM: Drosophila melanogaster

<400> SEQUENCE: 46

Met Ser Leu Ile Cys Arg Arg Phe Gly Ser Ser Leu Arg Pro Ile Ala
1               5                   10                  15

Arg Thr Leu His Pro Leu Leu Ala Ser Lys Ile Ile Glu Ala Gln Arg
            20                  25                  30

Ser Pro Leu Lys Asn Lys Arg Phe Tyr Ala Gly Lys Arg Met Asp Leu
        35                  40                  45

Lys Tyr Leu Asn Gln Lys Glu Ala Ile Ala Val Asp Gln Glu Leu Phe
    50                  55                  60

Asn Asp Tyr Lys Phe Ser Val Asp Gln Leu Met Glu Leu Ala Gly Leu
65                  70                  75                  80

Ser Cys Ala His Ala Val Ala Lys Cys Phe Pro Ala Glu Lys His Pro
                85                  90                  95

Arg Ile Leu Val Cys Cys Gly Pro Gly Asn Asn Gly Gly Asp Gly Leu

```
                100             105                 110
Val Ala Ala Arg His Leu Ala Leu Met Gly Tyr Thr Pro Thr Ile Tyr
            115                 120                 125

Tyr Pro Lys Pro Thr Ala Lys Pro Leu Phe Glu Asn Leu Ser His Gln
            130                 135             140

Cys Gln Gln Met Asp Ile Cys Asp Val Lys Glu Cys Pro Ser Val Glu
145                 150                 155                 160

Ser Ala Ala Arg Asp Tyr Asp Leu Ile Leu Asp Ala Leu Phe Gly Phe
                165                 170                 175

Ser Phe Lys Pro Pro Val Arg Ala Asp Phe Val Ala Val Val Glu Leu
            180                 185                 190

Met Gln Gln Thr Lys Leu Pro Ile Ala Ser Val Asp Ile Pro Ser Gly
            195                 200                 205

Trp Asp Val Glu Lys Gly Lys Leu Thr Glu Cys Asp Val Glu Pro Ala
            210                 215                 220

Leu Leu Ile Ser Leu Thr Ala Pro Lys Leu Cys Ala Arg Gln Phe Arg
225                 230                 235                 240

Gly Glu His His Tyr Leu Gly Gly Arg Phe Val Pro Pro Ala Leu Gln
                245                 250                 255

Arg Lys Tyr Glu Leu Asn Leu Pro Val Tyr Pro Gly Asn Glu Leu Cys
            260                 265                 270

Val Lys Leu
        275
```

<210> SEQ ID NO 47
<211> LENGTH: 279
<212> TYPE: PRT
<213> ORGANISM: artificial sequence
<220> FEATURE:
<223> OTHER INFORMATION: synthetic polypeptide

<400> SEQUENCE: 47

```
Met Ser Gly Leu Arg Ala Leu Leu Gly Leu Gly Leu Leu Val Ala Gly
1               5                   10                  15

Ser Arg Leu Pro Arg Val Leu Ser Gln Thr Ile Ala Cys Arg Ser Arg
            20                  25                  30

Pro Ser Trp Trp Gly Ser Gln Arg Leu Ser Gly Ser Glu Thr Met Ala
            35                  40                  45

Thr Ala Val Lys Tyr Leu Ser Gln Glu Glu Ala Gln Ala Val Asp Gln
            50                  55                  60

Glu Leu Phe Asn Asp Tyr Gln Phe Ser Val Asp Gln Leu Met Glu Leu
65                  70                  75                  80

Ala Gly Leu Ser Cys Ala Thr Ala Ile Ala Lys Ala Tyr Pro Pro Thr
                85                  90                  95

Ser Met Ser Lys Ser Pro Pro Thr Val Leu Val Ile Cys Gly Pro Gly
            100                 105                 110

Asn Asn Gly Gly Asp Gly Leu Val Cys Ala Arg His Leu Lys Leu Phe
            115                 120                 125

Gly Tyr Glu Pro Thr Ile Tyr Tyr Pro Lys Arg Pro Asn Lys Pro Leu
            130                 135                 140

Phe Thr Asn Leu Val Thr Gln Cys Gln Lys Met Asp Ile Pro Phe Leu
145                 150                 155                 160

Gly Glu Met Pro Glu Pro Met Ser Ile Asp Glu Leu Tyr Glu Leu Val
                165                 170                 175

Val Asp Ala Ile Phe Gly Phe Ser Phe Lys Gly Asp Val Arg Glu Pro
```

-continued

```
                180             185             190
Phe His Ser Ile Leu Ser Val Leu Lys Gly Leu Thr Val Pro Ile Ala
        195             200             205

Ser Ile Asp Ile Pro Ser Gly Trp Asp Val Glu Lys Gly Asn Pro Gly
        210             215             220

Ile Gln Pro Asp Leu Leu Ile Ser Leu Thr Ala Pro Lys Lys Ser Ala
225             230             235             240

Thr Gln Phe Thr Gly Arg Tyr His Tyr Leu Gly Gly Arg Phe Val Pro
                245             250             255

Pro Ala Leu Glu Lys Lys Tyr Gln Leu Asn Leu Pro Tyr Pro Gly Thr
                260             265             270

Glu Cys Val Tyr Arg Leu Gln
                275
```

US 10,364,275 B2

METHODS FOR TREATING INFLAMMATORY RESPONSES OR DISEASES CAUSED BY INFLAMMATION USING APOA-I BINDING PROTEIN (APOA1BP)

RELATED APPLICATIONS

This application is a national phase application claiming benefit of priority under 35 U.S.C. § 371 to Patent Convention Treaty (PCT) International Application serial number PCT/US2014/039549, filed May 27, 2014, which claims the benefit of priority under 35 U.S.C. § 119(e) of U.S. Provisional Application No. 61/827,729, filed May 27, 2013. The aforementioned applications are expressly incorporated herein by reference in their entirety and for all purposes.

GOVERNMENT RIGHTS

This invention was made with government support under grants HL093767, HL055798, HL114734 and HL081862, awarded by the National Institutes of Health (NIH). The government has certain rights in the invention.

REFERENCE TO SEQUENCE LISTING

A sequence listing that has been submitted on electronic form and also duplicated on paper after the abstract is part of this specification.

TECHNICAL FIELD

This invention generally relates to medicine and cell biology. In particular, in alternative embodiments, the invention provides pharmaceutical compounds and formulations comprising nucleic acids and polypeptides for regulating (including upregulating or inhibiting) the expression of ApoA-I Binding Protein (APOA1BP, AIBP, or AI-BP), and methods for making and using them. In alternative embodiments, APOA1BP-inhibiting pharmaceutical compositions and formulations of the invention are administered to an individual in need thereof in an amount sufficient to stimulate tissue revascularization, e.g., supporting or stimulating revascularization of heart tissue, e.g., after a cardiac ischemia. In alternative embodiments, pharmaceutical compositions and formulations of the invention that comprise APOA1BP nucleic acids and polypeptides or result in an increase in expression or activity of APOA1BP nucleic acids and polypeptides are administered to an individual in need thereof in an amount sufficient to treat, prevent, reverse and/or ameliorate a dyslipidemia, e.g., to treat, prevent, reverse and/or ameliorate conditions responsive to increasing cholesterol efflux from cells, including cardiovascular disease and atherosclerosis. In alternative embodiments, pharmaceutical compositions and formulations of the invention that comprise APOA1BP nucleic acids and polypeptides or result in an increase in expression or activity of APOA1BP nucleic acids and polypeptides are administered to an individual in need thereof in an amount sufficient to treat, prevent, reverse and/or ameliorate neovascularization of a growth, an infection, a cancer or a tumor whose growth or survival depends on neovascularization. In alternative embodiments, the administered formulations and pharmaceutical compositions of the invention comprise an APOA1BP polypeptide or protein that is a human or a mammalian APOA1BP, or an AIBP1 or an AIBP2, or a recombinant, peptidomimetic or a synthetic APOA1BP, or a bioisostere of an ApoA-I Binding Protein.

BACKGROUND

Cholesterol is one of the building blocks of the cell and is absolutely required for normal cellular function, but its excess often leads to abnormal proliferation, migration, inflammatory responses and/or cell toxicity. Removal of cholesterol from the cells to apoA-I and to HDL, an apoA-I-containing lipoprotein, is mediated by ATP-binding cassette transporters (ABC), predominantly ABCA1 and ATP-binding cassette sub-family G member 1 (ABCG1) (1-3). Recent reports that ABCA1/G1-deficient hematopoietic cells tend to hyperproliferate (4-6) and that ABCG1 and HDL protect against endothelial dysfunction in hypercholesterolemic mice (7) suggest the importance of efficient cholesterol efflux in maintaining cellular function.

ApoA-I binding protein (AIBP) is a secreted protein discovered in a screen of proteins that physically associate with apoA-I (8). The human AIBP gene (APOA1BP) is located at 1q22. 1q21.2 on chromosome 1, which corresponds to the 1q21-q23 locus for familial combined hyperlipidemia, a common, multifactorial and heterogeneous dyslipidemia predisposing to premature coronary artery disease (9). This chromosomal location of the gene and the protein binding to apoA-I, the primary apolipoprotein involved in removal of cholesterol from cells, prompted the hypothesis that AIBP is involved in cholesterol efflux (8, 10). However, a function of AIBP in cholesterol metabolism has not been experimentally tested.

SUMMARY

In alternative embodiments, the invention provides formulations and pharmaceutical compositions comprising:
(a) an ApoA-I Binding Protein (APOA1BP, AIBP, or AI-BP) polypeptide or peptide, or a compound or composition that increases expression or activity of a APOA1BP polypeptide or nucleic acid, or a polypeptide or peptide having a APOA1BP activity,
wherein optionally the polypeptide or peptide having a APOA1BP activity, or the APOA1BP polypeptide or peptide, comprises a recombinant, a synthetic, a peptidomimetic or an isolated polypeptide or peptide having a APOA1BP activity or APOA1BP polypeptide or peptide; or
(b) the formulation or pharmaceutical composition of (a), wherein the compound that increases expression or activity of a APOA1BP polypeptide is a nucleic acid that expresses a APOA1BP polypeptide or a polypeptide having a APOA1BP polypeptide activity,
and optionally a APOA1BP-stimulating compound or composition increases or stimulates (activates) the activity of a APOA1BP promoter or transcriptional regulatory sequence or motif.

In alternative embodiments, the invention provides formulations and pharmaceutical compositions comprising:
(a) an ApoA-I Binding Protein (APOA1BP, AIBP, or AI-BP)-inhibiting compound or composition;
(b) the formulation or pharmaceutical composition of (a), wherein the APOA1BP-inhibiting compound or composition inhibits or decreases the expression of a APOA1BP nucleic acid,
wherein optionally the nucleic acid inhibited is a APOA1BP gene or a APOA1BP message (mRNA),
and optionally the APOA1BP-inhibiting nucleic acid is an APOA1BP antisense oligonucleotide, or a APOA1BP-inhibiting miRNA or siRNA, and optionally the APOA1BP antisense oligonucleotide, or a APOA1BP-inhibiting miRNA or siRNA, comprises a morpholino oligonucleotide, and optionally a APOA1BP-inhibiting compound or composition inhibits or decreases the activity of a APOA1BP promoter or transcriptional regulatory sequence or motif; or (c) the formulation or pharmaceutical composition of (a), wherein the APOA1BP-inhibiting compound or composition inhibits or decreases the expression of a APOA1BP polypeptide, wherein optionally the APOA1BP polypeptide-inhibiting compound is an anti-APOA1BP antibody or a APOA1BP-binding antibody or antibody-like fragment, a small molecule, a lipid or a carbohydrate.

In alternative embodiments of the formulations and pharmaceutical compositions of the invention:

the APOA1BP polypeptide or protein is a human or a mammalian APOA1BP, or a AIBP1 or a AIBP2, or a recombinant, peptidomimetic or a synthetic APOA1BP, or a bioisostere of an ApoA-I Binding Protein (APOA1BP, AIBP, or AI-BP); or the APOA1BP-inhibiting or APOA1BP-stimulating compound or composition is formulated:

(a) for administration in vitro or in vivo;
(b) for enteral or parenteral administration;
(c) as a liposome, a nanoparticle, or a nanoliposome;
(d) as a tablet, a pill, a capsule, a gel, a hydrogel, a geltab, a liquid, a powder, an emulsion, a lotion, an aerosol, a spray, a lozenge, an aqueous or a sterile or an injectable solution, an eye drop, or an implant; or
(e) intravenous injection, subcutaneous injection, intramuscular injection, inhalation, or intravitreal injection.

In alternative embodiments, the invention provides methods for stimulating cholesterol efflux from a cell, comprising:

(a) contacting the cell with an effective amount of a APOA1BP activity-increasing formulation or pharmaceutical composition comprising:

an ApoA-I Binding Protein (APOA1BP, AIBP, or AI-BP) polypeptide or peptide, or a compound or composition that increases expression or activity of a APOA1BP polypeptide or nucleic acid, or a polypeptide or peptide having a APOA1BP activity, or a compound that increases expression or activity of a APOA1BP polypeptide is a nucleic acid that expresses a APOA1BP polypeptide or a polypeptide having a APOA1BP polypeptide activity, wherein optionally the administration is in vitro, ex vivo or in vivo; or (b) stimulating the expression of an exogenous or an endogenous nucleic acid expressing a polypeptide or peptide having an APOA1BP activity, or an APOA1BP polypeptide or peptide, wherein the nucleic acid comprises a gene or a message (mRNA), or an APOA1BP promoter or transcriptional regulatory sequence or motif;

and optionally the cell is an endothelial cell, or a human cell.

In alternative embodiments, the invention provides methods for:

inhibiting, reversing or reducing the rate of formation of lipid rafts or cholesterol-/sphingolipids membrane microdomains, inhibiting receptor dimerization, or increasing levels of high density lipoprotein (HDL) and/or improving HDL function, comprising:

(a) administering to an individual an effective amount of an APOA1BP activity increasing formulation or a pharmaceutical composition of the invention, wherein optionally the formulation or pharmaceutical composition comprises a APOA1BP polypeptide or peptide having APOA1BP activity, a APOA1BP-stimulating polypeptide compound or composition, or a compound that increases expression or activity of a APOA1BP polypeptide or nucleic acid, wherein optionally the administration is ex vivo or in vivo, wherein optionally the administration is in vitro, ex vivo or in vivo; or (b) stimulating the expression of an exogenous or an endogenous nucleic acid expressing a polypeptide or peptide having an APOA1BP activity, or an APOA1BP polypeptide or peptide, wherein the nucleic acid comprises a gene or a message (mRNA), or an APOA1BP promoter or transcriptional regulatory sequence or motif, and optionally the individual is a human.

In alternative embodiments, the invention provides methods for:

inhibiting or slowing vascular endothelial cell growth, or neovascularization, or angiogenesis, treating, reversing, preventing or down-regulating an inflammatory response, an inflammation or a disease or condition caused by or creating an inflammation, or treating, reversing, preventing or down-regulating a macular degeneration or a wet macular degeneration, comprising:

(a) administering to an individual an effective amount of an APOA1BP activity increasing formulation or a pharmaceutical composition of the invention, wherein optionally the formulation or pharmaceutical composition comprises a APOA1BP polypeptide or peptide having APOA1BP activity, a APOA1BP-stimulating polypeptide compound or composition, or a compound that increases expression or activity of a APOA1BP polypeptide or nucleic acid, wherein optionally the administration is ex vivo or in vivo, wherein optionally the administration is in vitro, ex vivo or in vivo; or (b) stimulating the expression of an exogenous or an endogenous nucleic acid expressing a polypeptide or peptide having an APOA1BP activity, or an APOA1BP polypeptide or peptide, wherein the nucleic acid comprises a gene or a message (mRNA), or an APOA1BP promoter or transcriptional regulatory sequence or motif, and optionally the individual is a human, and optionally the disease or condition caused by or creating an inflammation comprise an inflammatory bowel disease (IBD).

In alternative embodiments, the invention provides methods for:

inhibiting, preventing or slowing or reversing the growth of a vascularized tumor, a vascularized dysplastic tissue, a vascularized tissue, a vascularized growth, an infection dependent on neovascularization, or a cancer, comprising:

comprising:

(a) administering to an individual an effective amount of an APOA1BP activity increasing formulation or a pharmaceutical composition of the invention, wherein optionally the formulation or pharmaceutical composition comprises a APOA1BP polypeptide or peptide having APOA1BP activity, a APOA1BP-stimulating polypeptide compound or composition, or a compound that increases expression or activity of a APOA1BP polypeptide or nucleic acid, wherein optionally the administration is ex vivo or in vivo, wherein optionally the administration is in vitro, ex vivo or in vivo; or (b) stimulating the expression of an exogenous or an endogenous nucleic acid expressing a polypeptide or peptide having an APOA1BP activity, or an APOA1BP polypeptide or peptide, wherein the nucleic acid comprises a gene or a message (mRNA), or an APOA1BP promoter or transcriptional regulatory sequence or motif, and optionally the individual is a human, and optionally the cancer is a leukemia.

In alternative embodiments, the invention provides methods for:

treating, preventing, ameliorating or reversing the effects of a dyslipidemia, a hyperlipidemia, an atherosclerosis, a heart disease, a coronary artery disease, a heart attack, an ischemic event or a stroke:

comprising:

(a) administering to an individual an effective amount of an APOA1BP activity increasing formulation or a pharmaceutical composition of the invention, wherein optionally the formulation or pharmaceutical composition comprises a APOA1BP polypeptide or peptide having APOA1BP activity, a APOA1BP-stimulating polypeptide compound or composition, or a compound that increases expression or activity of a APOA1BP polypeptide or nucleic acid, wherein optionally the administration is ex vivo or in vivo, wherein optionally the administration is in vitro, ex vivo or in vivo; or (b) stimulating the expression of an exogenous or an endogenous nucleic acid expressing a polypeptide or peptide having an APOA1BP activity, or an APOA1BP polypeptide or peptide, wherein the nucleic acid comprises a gene or a message (mRNA), or an APOA1BP promoter or transcriptional regulatory sequence or motif, and optionally the individual is a human.

In alternative embodiments, the invention provides methods for:

interfering with vascular endothelial growth factor receptor 2 (VEGRF2) (also known as kinase insert domain receptor, or KDR) dimerization or signaling, comprising:

(a) administering to an individual an effective amount of an APOA1BP activity increasing formulation or a pharmaceutical composition of the invention, wherein optionally the formulation or pharmaceutical composition comprises a APOA1BP polypeptide or peptide having APOA1BP activity, a APOA1BP-stimulating polypeptide compound or composition, or a compound that increases expression or activity of a APOA1BP polypeptide or nucleic acid, wherein optionally the administration is ex vivo or in vivo, wherein optionally the administration is in vitro, ex vivo or in vivo; or (b) stimulating the expression of an exogenous or an endogenous nucleic acid expressing a polypeptide or peptide having an APOA1BP activity, or an APOA1BP polypeptide or peptide, wherein the nucleic acid comprises a gene or a message (mRNA), or an APOA1BP promoter or transcriptional regulatory sequence or motif, and optionally the individual is a human.

In alternative embodiments, the invention provides methods for inhibiting, preventing or slowing or reversing:

a nonalcoholic steatohepatitis (NASH), a diabetes, an acute respiratory distress syndrome, or a sepsis, comprising:

(a) administering to an individual an effective amount of an APOA1BP activity increasing formulation or a pharmaceutical composition of the invention, wherein optionally the formulation or pharmaceutical composition comprises a APOA1BP polypeptide or peptide having APOA1BP activity, a APOA1BP-stimulating polypeptide compound or composition, or a compound that increases expression or activity of a APOA1BP polypeptide or nucleic acid, wherein optionally the administration is ex vivo or in vivo, wherein optionally the administration is in vitro, ex vivo or in vivo; or (b) stimulating the expression of an exogenous or an endogenous nucleic acid expressing a polypeptide or peptide having an APOA1BP activity, or an APOA1BP polypeptide or peptide, wherein the nucleic acid comprises a gene or a message (mRNA), or an APOA1BP promoter or transcriptional regulatory sequence or motif, and optionally the individual is a human.

In alternative embodiments, the invention provides methods for:

promoting or accelerating revascularization, promoting revascularization of a heart, an organ or a tissue, or promoting revascularization of a heart, an organ or a tissue following an ischemic event or a stroke (e.g., promoting revascularization of a heart, an organ or a tissue post-ischemically), comprising:

administering a APOA1BP-inhibiting formulation or an APOA1BP activity-inhibiting pharmaceutical composition of the invention, wherein optionally the APOA1BP-inhibiting compound or composition inhibits or decreases the expression of a APOA1BP nucleic acid, and optionally the nucleic acid inhibited is a APOA1BP gene or a APOA1BP message (mRNA), and optionally the APOA1BP-inhibiting nucleic acid is an APOA1BP antisense oligonucleotide, or a APOA1BP-inhibiting miRNA or siRNA, and optionally a APOA1BP-inhibiting compound or composition inhibits or decreases the activity of a APOA1BP promoter or transcriptional regulatory sequence or motif;

and optionally the APOA1BP-inhibiting compound or composition inhibits or decreases the expression of a APOA1BP polypeptide, and optionally the APOA1BP polypeptide-inhibiting compound is an anti-APOA1BP antibody or a APOA1BP-binding antibody or antibody-like fragment, a small molecule, a lipid or a carbohydrate.

In alternative embodiments, the invention provides kits comprising a formulation or a pharmaceutical composition of the invention, and optionally comprising instructions on practicing a method of the invention.

In alternative embodiments, the invention provides nanoparticles, nanolipoparticles, vesicles or liposomal membranes comprising a formulation or a pharmaceutical composition of the invention.

In alternative embodiments, the invention provides use of a formulation or a pharmaceutical of the invention, or a nanoparticle, nanolipoparticle, vesicle or liposomal membrane of the invention, or a combination thereof, in the manufacture of a medicament.

In alternative embodiments, the invention provides use of a formulation or a pharmaceutical of the invention, or a nanoparticle, nanolipoparticle, vesicle or liposomal membrane of the invention, in the manufacture of a medicament for interfering with vascular endothelial growth factor receptor 2 (VEGRF2 or KDR) dimerization or signaling.

In alternative embodiments, the invention provides use of a formulation or a pharmaceutical of the invention, or nanoparticle, nanolipoparticle, vesicle or liposomal membrane of the invention, in the manufacture of a medicament for promoting or accelerating revascularization, or promoting revascularization of the heart, or promoting revascularization of the heart following an ischemic event (promoting post-ischemic vascularization).

In alternative embodiments, the invention provides use of a formulation or a pharmaceutical of the invention, or nanoparticle, nanolipoparticle, vesicle or liposomal membrane of the invention, in the manufacture of a medicament for treating, preventing, ameliorating or reversing the effects of a dyslipidemia, hyperlipidemia, atherosclerosis or coronary artery disease.

In alternative embodiments, the invention provides use of a formulation or a pharmaceutical of the invention, or nanoparticle, nanolipoparticle, vesicle or liposomal membrane of the invention, in the manufacture of a medicament for inhibiting or slowing or reversing the growth of a vascularized tumor, dysplastic tissue, tissue or growth, or a cancer.

In alternative embodiments, the invention provides use of a formulation or a pharmaceutical of the invention, or nanoparticle, nanolipoparticle, vesicle or liposomal membrane of the invention, in the manufacture of a medicament for inhibiting or slowing vascular endothelial cell growth, or neovascularization, or angiogenesis.

In alternative embodiments, the invention provides use of a formulation or a pharmaceutical of the invention, or nanoparticle, nanolipoparticle, vesicle or liposomal membrane of the invention, in the manufacture of a medicament for inhibiting, reversing or reducing the rate of formation of lipid rafts or cholesterol-/sphingolipids membrane microdomains, or increasing levels of high density lipoprotein (HDL) and/or improving HDL function.

In alternative embodiments, the invention provides use of a formulation or a pharmaceutical of the invention, or nanoparticle, nanolipoparticle, vesicle or liposomal membrane of the invention, in the manufacture of a medicament for stimulating cholesterol efflux from a cell.

In alternative embodiments, the invention provides use of a formulation or a pharmaceutical of the invention, or nanoparticle, nanolipoparticle, vesicle or liposomal membrane of the invention, in the manufacture of a medicament for inhibiting, preventing or slowing or reversing: a nonalcoholic steatohepatitis (NASH), a diabetes, an acute respiratory distress syndrome, or a sepsis.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The drawings set forth herein are illustrative of embodiments of the invention and are not meant to limit the scope of the invention as encompassed by the claims.

FIG. 1A-G illustrate the role of AIBP in zebrafish angiogenesis:

FIG. 1(A) illustrates images of one-cell stage fli1:EGFP zebrafish embryos that were injected with 8 ng of either control morpholino oligonucleotide (MO) or AIBP2 antisense morpholino oligonucleotides (MO) targeting ATG translation site, and the images of segmental arteries (SeA) (images 1-2) and of subintestinal veins (SIV) (images 3-4) were captured 3 days after MO injection and arrows point to dysregulated sprouts;

FIG. 1(B) graphically illustrates the numbers of embryos with abnormal angiogenesis resulting from injection of control or AIBP2 MO;

FIG. 1(C) illustrates images of one-cell stage fli1:nEGFP embryos that were injected with 8 ng of either control MO or AIBP2 MO;

FIG. 1(D) graphically illustrates the quantification of endothelial cell (EC) nuclei in images of segmental arteries (SeA);

FIG. 1(E) illustrates the tissue distribution of AIBP2 mRNA in zebrafish embryos at the 20 minutes (min) post fertilization, the 12 hours post fertilization (hpt) and the 24 hours post fertilization (hpf) developmental stages;

FIG. 1(F) illustrates images of a mosaic expression analysis of endothelial cell (EC) branching in wild type (WT) and AIBP2 knockdown (KD) embryos, arrowheads indicate aberrant ectopic branches/sprouts in the AIBP2 KD recipients; and, FIG. 1(G) graphically illustrates the numbers of ectopic branches/filopodial projections per SeA;

Figure 10A:
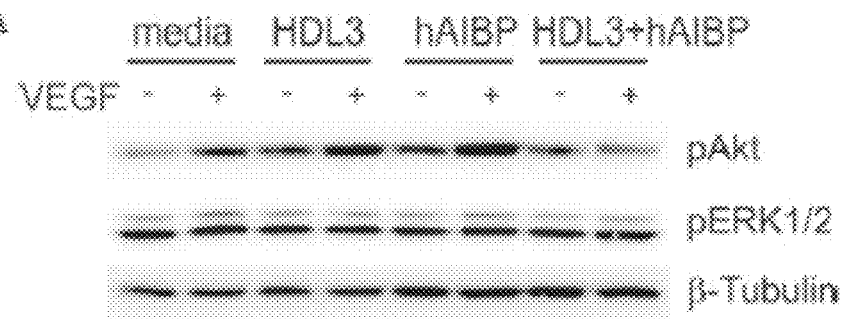

as described in detail in Example 1, below.

FIG. 2A-F illustrate images and data showing upregulated markers of endothelial cell (EC) proliferation and angiogenesis in AIBP2 morphants:

FIG. 2(A) graphically illustrates the expression of genes involved in angiogenesis, including endothelium-specific receptor tyrosine kinase 2 (Tie2), kinase insert domain receptor (KDR), Fetal Liver Kinase 1 (Flk1) and Friend leukemia integration 1 transcription factor (FLI1);

FIG. 2(B) illustrates whole embryo in situ hybridization (WISH) analysis of genes involved in angiogenesis, including endothelium-specific receptor tyrosine kinase 2 (Tie2), Fetal Liver Kinase 1 (Flk1), Fms-related tyrosine kinase 4 (Flt4), neurogenic locus notch homolog protein 3 (Notch3), and Delta like ligand 4 (Dll4);

FIG. 2(C) illustrates immunoblot images of Akt (also known as Protein Kinase B (PKB)) and extracellular-signal-regulated kinases (ERK) 1/2 phosphorylation;

FIG. 2(D), FIG. 2(E) and FIG. 2(F) illustrate free cholesterol levels in AIBP2 morphants, where FIG. 2(D) illustrates fluorescence images of 24 hours post fertilization (hpf) control and AIBP2 morphants stained with filipin to detect free cholesterol in embryos, and FIG. 2(E) graphically illustrates the intensities of filipin fluorescence images, and FIG. 2(F) graphically illustrates free cholesterol levels determined by gas chromatography (GC), in one-cell stage embryos injected with control or AIBP2 MO;

as described in detail in Example 1, below.

FIG. 3A-F illustrate images and data showing the effect of AIBP on cholesterol efflux:

FIG. 3(A) illustrates different fractions of lipoproteins run on SDS-PAGE and immunoblotted with indicated antibodies;

FIG. 3(B) illustrates immunoprecipitated and immunoblotted purified human ApoA-I mixed with His-tagged AIBP2 or hAIBP;

FIG. 3(C) graphically illustrates cholesterol efflux to HDL3, where human umbilical vein endothelial cells (HUVEC) cells were preloaded with 3H-cholesterol and then incubated with media, HDL3, HDL3+His-AIBP, or HDL3+His-DUB, and the media and cell lysates were collected and 3H counts measured;

FIG. 3(D) graphically illustrates the kinetics of cholesterol efflux from HUVEC to HDL3, with the experimental conditions as in FIG. 3C;

FIG. 3(E) illustrates images showing the effects of hAIBP and HDL3 on EC tube formation, where HUVEC were preincubated with HDL3, His-hAIBP, or HDL3+His-hAIBP, cells were then seeded on MATRIGEL™ (BD Biosciences) in the presence or absence of VEGF, and imaged following a 12 hour incubation;

FIG. 3(F) (upper graph) graphically illustrates data showing the effect of ATP-binding cassette sub-family G member 1 (ABCG1) knockdown on hAIBP mediated-cholesterol efflux, where HUVEC were transfected with control or ABCG1 siRNA, and (lower gel) illustrates by western blot ABCG1 knockdown;

as described in detail in Example 1, below.

FIG. 4A-I illustrate images and data showing the role of ABCA1/G1 in angiogenesis and in mediating effects of AIBP:

FIG. 4(A) and FIG. 4(D) illustrate images of segmental arteries (SeA) (A) and SIV (D), and FIG. 4(B), FIG. 4(C), FIG. 4(E) and FIG. 4(F) graphically illustrate: angiogenic defects in ABCA1/G1 morphants, where one-cell stage embryos were injected with a control MO, AIBP2 MO, or ABCA1 MO+ABCG1 MO, and 3 days later the morphants were analyzed by confocal microscopy; the graphs show number and length of segmental arteries (SeA) ectopic branches (FIG. 4B and FIG. 4C) and SIV ectopic sprouts (FIG. 4E and FIG. 4F) from 5 to 12 embryos;

FIG. 4(B) illustrates images of, and FIG. 4(H) graphically illustrates, the rescue of the effect of AIBP2 overexpression in ABCA1/G1 morphants, where FIG. 4(G) illustrates confocal microscope images of one cell stage embryos injected with myog-AIBP2-mCherry plasmid, myog-AIBP2-mcherry plasmid together with ABCA1/G1 MO, or myog-mCherry, and two days later, the embryos were analyzed by confocal microscope;

FIG. 4(I) schematically illustrates a diagram representing the hypothesis that somite expression of AIBP2 accelerates lateral cholesterol efflux from growing endothelial cell (EC) and thereby prevents its ectopic sprouting/branching;

as described in detail in Example 1, below.

Figure 5:
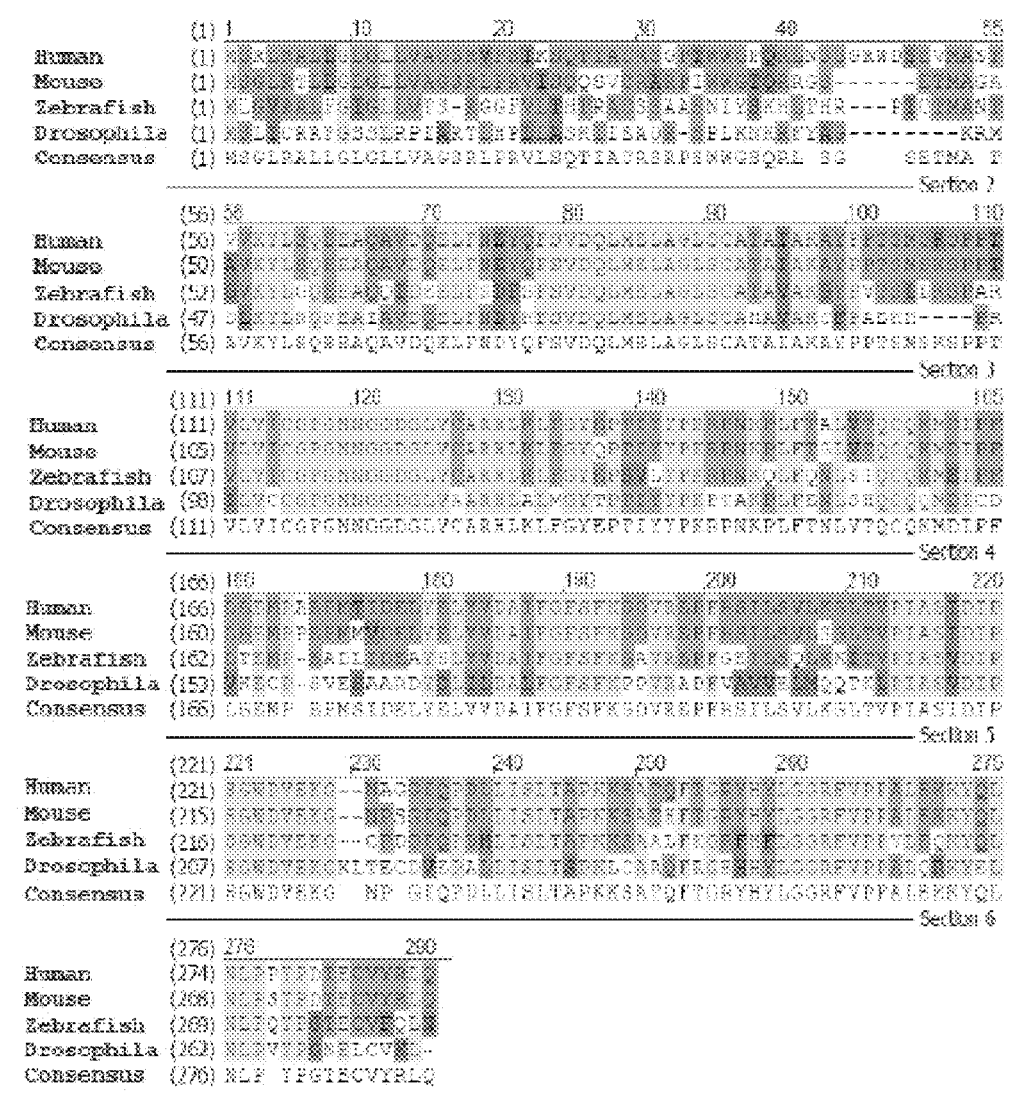

FIG. 5 illustrates images aligning and comparing AIBP protein amino acid sequences of human (SEQ ID NO:43), mouse (SEQ ID NO:44), zebrafish (SEQ ID NO:45), *Drosophila* (SEQ ID NO:46), and a consensus sequence (SEQ ID NO:47), showing a conservation of AIBP proteins across different species. AIBP protein sequences were retrieved from ENZEMBL™ (EMBL-EBI; Wellcome Trust Sanger Institute) and were compared using VECTOR NTI™ software (Invitrogen); as described in detail in Example 1, below.

Figure 6:
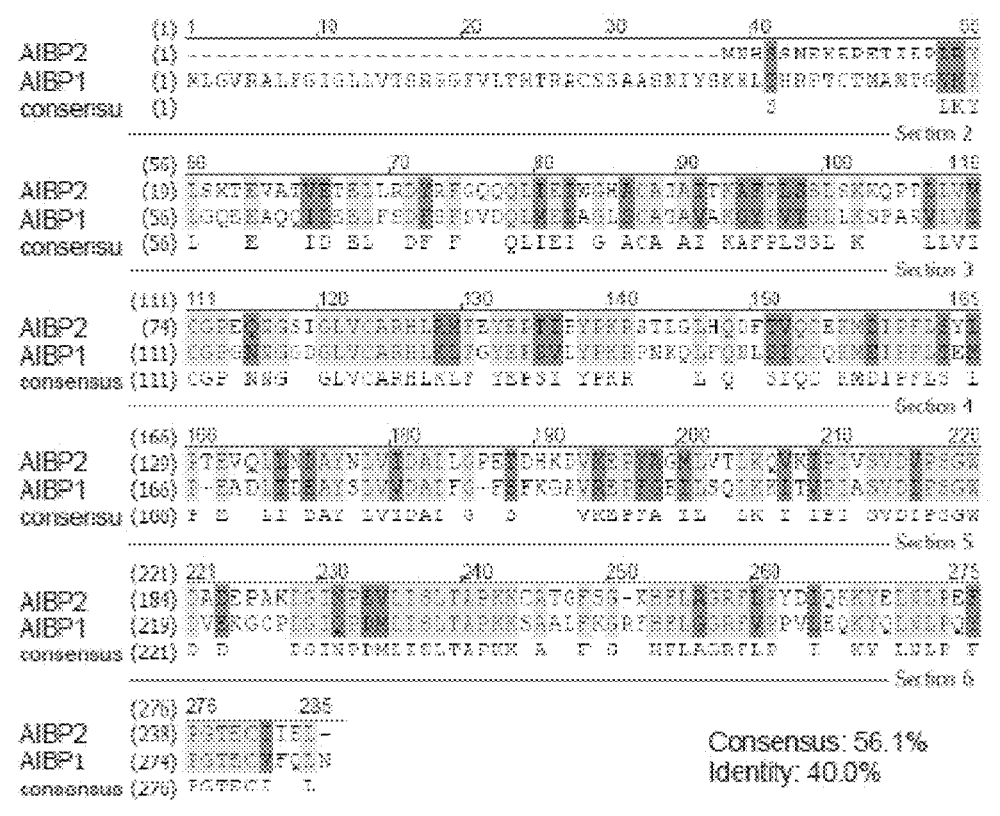

FIG. 6 illustrates images aligning and comparing the isoforms of zebrafish AIBP; comparisons were performed using VECTOR NTI™ software; as described in detail in Example 1, below.

FIG. 7A-D images showing dysregulated SeA and SIV angiogenesis in AIBP2 morphants (splicing site); Onecell stage fli1:EGFP zebrafish embryos were injected with 8 ng of either control MO or AIBP2 MO2 targeting a splicing site; the images of SeA (FIG. 7A and FIG. 7B) and SIV (FIG. 7C) were captured 3 days after MO injection; arrows point to dysregulated sprouts; scale: 50 m. FIG. 7D left schematic illustrates a diagram showing targeted splicing site and FIG. 7D right image illustrates a gel showing corresponding PCR products; PF and PR indicate the primers used for the amplification; as described in detail in Example 1, below.

FIG. 8 illustrates tables showing selected results from microarray analysis of 12 hours post fertilization (hpf) AIBP2 morphants; one cell stage embryos were injected with either control or AIBP2 MO; twelve hours later, total RNA of injected embryos were extracted and analyzed in a microarray; as described in detail in Example 1, below.

FIG. 9(A) illustrates an image of an SDS gel probed with antibodies showing the specificity of AIBP2 antibody; a polyclonal antibody against zebrafish AIBP2 (guinea pig post-immune serum) was used to probe zebrafish homogenates; fifteen, 10 and 5 µl of the homogenates were loaded on an SDS gel and probed with the antibody, preincubated with 10 µg of either ubiqitine (Ub) or AIBP2 (both recombinant proteins were produced from the same expression vector and under the same conditions); the blots were visualized with an anti-guinea pig IgG conjugated with HRP and a chemiluminescent substrate; as described in detail in Example 1, below.

FIG. 9(B) illustrates an image of an agarose gel electrophoresis of human lipoprotein fractions separated by ultracentrifugation; DUB, deubiquitinase; Sta, human standard plasma; LPDS, lipoprotein-deficient serum; as described in detail in Example 1, below.

FIG. 10(A) illustrates an image of an SDS gel probed with antibody probes showing the effect of AIBP on Akt and ERK1/2 phosphorylation in HUVEC; where HUVEC were preincubated with 50 µg/ml HDL3, or 50 µg/ml HDL3+0.2 µg/ml His-AIBP for 4 hours, followed by a 20 min stimulation with 50 ng/ml VEGF. Cells were lysed, and the lysates run on SDS-PAGE and probed as indicated; as described in detail in Example 1, below.

Figure 10B:
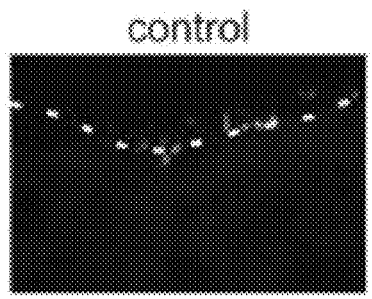
Figure 10C:
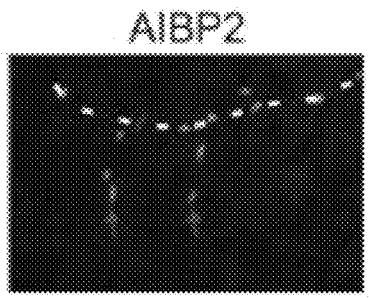
Figure 10D:
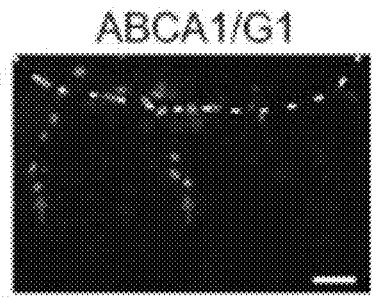
Figure 10E:
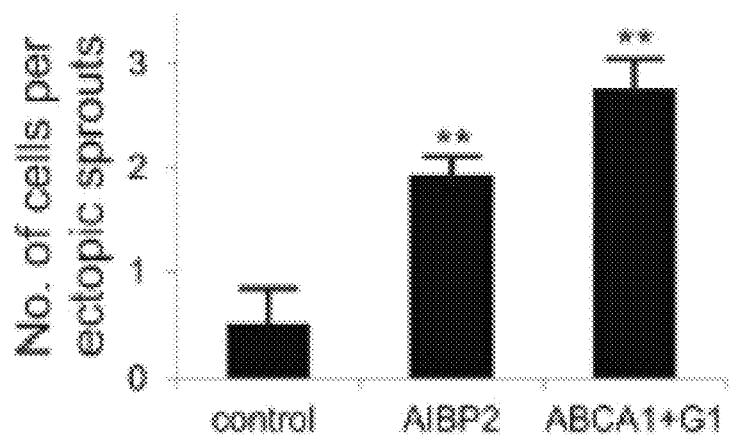

FIG. 10-A-E illustrate images of SIV sprouting in AIBP2 and ABCA1/G1 morphants; where FIG. 10B, FIG. 10C, and FIG. 10D, illustrate images of one-cell stage embryos of Tg(fli1:negfp)$_{y7}$ transgenic zebrafish in which EC nuclei are fluorescent green, were injected with 8 ng of control MO, 8 ng AIBP2 MO, or 4 ng ABCA1 MO+4 ng ABCG1 MO, and the embryos were analyzed at 3 dpf; red arrows indicate excessive cell proliferation in the ectopic sprouts; scale, 20 µm. FIG. 10E graphically illustrates the numbers of cells per SIV sprout were quantified in 6-15 embryos per group. **, p<0.01; as described in detail in Example 1, below.

Figure 11:
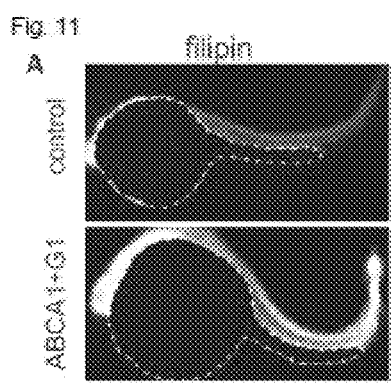
Figure 11:
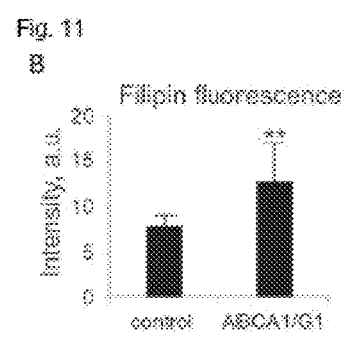
Figure 11:
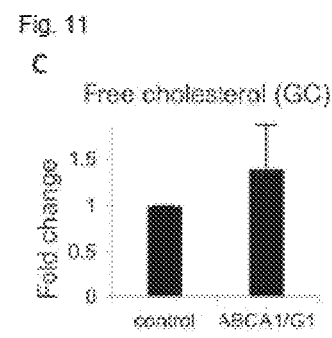

FIG. 11-A-C illustrate an image and graphs showing free cholesterol levels in ABCA1/G1 morphants: FIG. 11(A) illustrates representative images of 24 hpf control and ABCA1/G1 morphants stained with filipin to detect free cholesterol; note the yolks are artificially masked; FIG. 11(B) graphically illustrates data showing the intensity of filipin fluorescence in images shown in panel A (FIG. 11(A)) (without yolks) was quantified in 8-10 embryos per group. *, p<0.05; FIG. 11(C) graphically illustrates data showing free cholesterol levels of one-cell stage embryos which were injected with control or AIBP2 MO, and at 24 hpf, the trunk area (without yolk and head) was dissected and total lipid was extracted; free cholesterol levels were determined by GC; the cholesterol levels were normalized to the protein content and then to the values in control MO embryos; 50 to 70 embryos were pooled for each sample; the data are from 3-4 independent experiments; as described in detail in Example 1, below.

Figure 12:
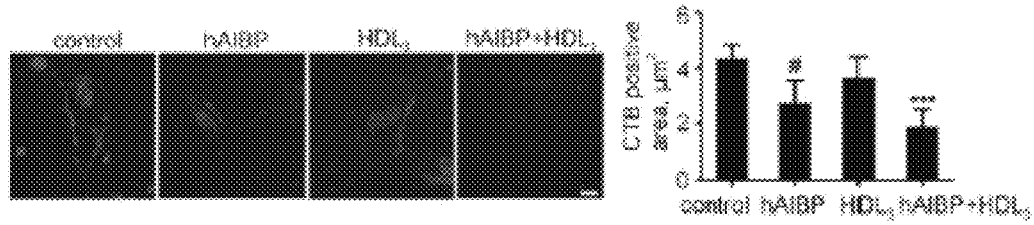
Figure 12:
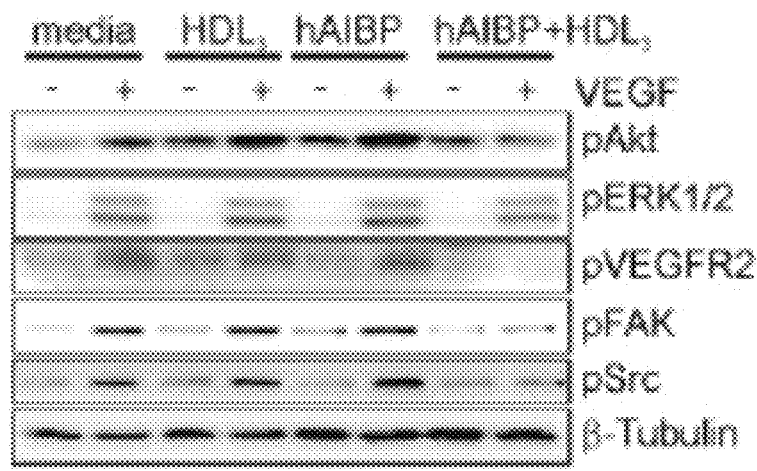
Figure 12F:
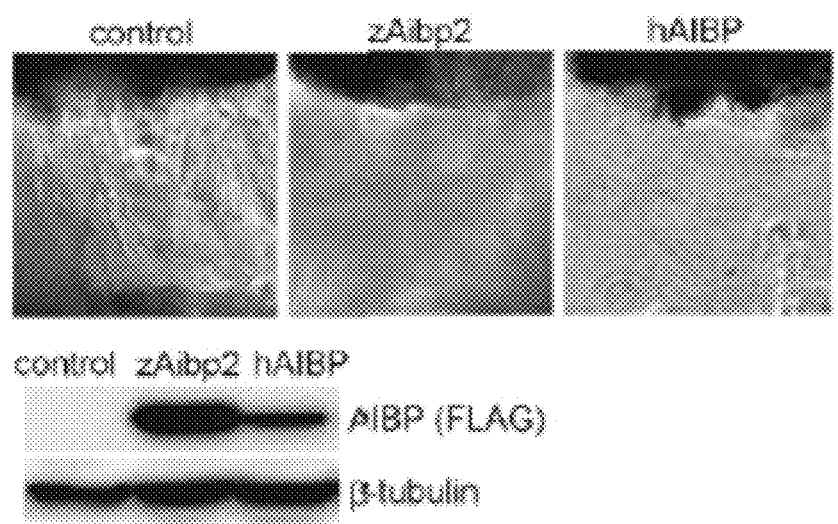

FIG. 12A-F in images and graphics shows the role of AIBP in cholesterol efflux from endothelial cell (EC) and in vitro angiogenesis:

FIG. 12a graphically illustrates data showing the effect of ATP-binding cassette sub-family G member 1 (ABCG1) knockdown on hAIBP mediated-cholesterol efflux;

FIG. 12b illustrates images showing the effect of hAIBP and HDL3 on EC tube formation where HUVEC were preincubated with HDL3, hAIBP, or HDL3+hAIBP for 4 hours;

FIG. 12c upper image illustrates images showing the requirement for ABCG1 in hAIBP inhibition of angiogenesis, where HUVEC were transfected with control or ABCG1 siRNA and used in an EC tube formation assay, and FIG. 12c lower graph illustrates this data;

FIG. 12d illustrates images and graphics showing the effect of hAIBP and HDL3 on lipid rafts, left image shows images of control, hAIBP, $HDL_3$ and hAIBP and $HDL_3$ samples, and the right image graphically depicts the CTB positive area, or amount of lipid rafts, as shown in the left images;

FIG. 12e illustrates images of probed SDS-PAGE showing the effect of hAIBP on VEGF signaling;

FIG. 12f upper illustrates images showing an aortic ring angiogenesis assay wherein the aorta was isolated from a C57BL6 mouse and sliced into 1 mm wide rings, and the aortic rings were embedded in MATRIGEL™, and HEK293 cells expressing zAibp2 or hAIBP were inserted approximately 0.5 mm away from the aortic ring, and the plates were incubated with 10 ng/ml VEGF for 7 days; FIG. 12f lower illustrates immunoblots showing expression of hAIBP and zAibp2 in HEK293 cells;

as described in detail in Example 2, below.

FIG. 13 in images and graphics shows the effect of AIBP deficiency on zebrafish cholesterol metabolism and angiogenesis:

FIG. 13a illustrates by image, and FIG. 13b and FIG. 13c graphically illustrate, free cholesterol levels in zaibp2 morphants:

FIG. 13a illustrates an image of one-cell stage AB zebrafish embryos injected with either control MO or zaibp2 MO targeting ATG translation site, and twenty four hpf control and zaibp2 morphants were fixed and stained with filipin to detect free cholesterol in embryos;

FIG. 13b graphically illustrates data where the intensities of filipin fluorescence in images shown in panel FIG. 13A were quantified in 12 to 15 embryos per group;

FIG. 13c graphically illustrates data of free cholesterol levels as determined by GC, where at 24 hpf, the trunk area was dissected and total lipids were extracted, and the cholesterol levels were normalized to the protein content and then to the values in control MO embryos;

FIG. 13d, FIG. 13e and FIG. 13f illustrate images showing the angiogenic defects in zaibp2 morphants, where one-cell stage Tg(fli1:egfp)y1 zebrafish embryos were injected with either control MO or zaibp2 MO targeting ATG translation site:

FIG. 13d illustrates low magnification bright field images showing the area of fluorescent imaging of SeA (right, or white box) and SIV (left, or red box), in a control (upper image) and a zaibp2 morphant (lower image);

FIG. 13e illustrates images of SeA in 30 hpf embryos (top row), and SeA (middle and panel images) and of SIV (lower panel images) in 3 dpf embryos, where the arrows point to dysregulated sprouts, for control and zaibp2 morphant;

FIG. 13f graphically illustrates a quantification of the number of embryos with normal and abnormal angiogenesis (SeA with ectopic branching) resulting from injection of control or zaibp2 MO;

as described in detail in Example 2, below.

FIG. 14 in images and graphics shows the effect of AIBP deficiency and ectopic overexpression on zebrafish angiogenesis and VEGF signaling:

FIG. 14a illustrates images of tissue distribution of zaibp2 mRNA in zebrafish embryo, where embryos at different developmental stages were fixed and whole mount in situ hybridization (WISH) was performed with an antisense zaibp2 probe;

FIG. 14b left panels illustrates images of a mosaic expression analysis of EC branching in WT and zaibp2 knockdown embryos; red arrowheads indicate aberrant ectopic branches/ sprouts; and FIG. 14b right graph shows data quantifying the number of ectopic sprouts per SecA;

FIG. 14c illustrates images showing that the ectopic expression of zAibp2 inhibits SeA growth: one-cell stage Tg(fli1:egfp)y1 embryos were injected with DNA constructs for myog:Gal4, DsRed: 10×UAS:zAibp2 or myog:Gal4, DsRed: 10×UAS expression; images were captured at 30 hpf; arrowheads point to aberrant SeA growth close to the sites of DsRed (and zAibp2) expression;

FIG. 14d graphically illustrates data showing the expression of genes involved in angiogenesis; total RNA was isolated from 24 hpf control and zaibp2 morphants and qRT-PCR was performed;

FIG. 14e illustrates images of SDSPAGE and immunoblots showing phosphorylation of signaling proteins: lysates of 24 hpf control and control MO, zaibp2 and abca1/g1 (abca1 MO+abcg1 MO); morphants were separated on SDSPAGE and immunoblotted as indicated;

as described in detail in Example 2, below.

FIG. 15 in images and graphics shows the role of Abca1 and Abcg1 in angiogenesis and in mediating effects of Aibp:

FIG. 15a left panel images illustrate images showing the angiogenic defects in abca1/g1 morphants; one-cell stage embryos were injected with control MO, zaibp2 MO, or abca1 MO+abcg1 MO; and images of SeA (30 hpf) and SIV (3 dpf) are shown; FIG. 15a right graphs show numbers and of SeA ectopic branches and numbers and length of SIV ectopic sprouts from 5 to 12 embryos;

FIG. 15b left panel images illustrate images showing rescue of the effect of zAibp2 overexpression in abca1/g1 morphants; one-cell stage embryos were injected with myog:zAibp2-mCherry plasmid, myog:zAibp2-mCherry plasmid together with abca1/g1 MO, or myog:mCherry plasmid; the arrow points to an aberrant SeA at the site of zAibp2-mCherry expression; FIG. 15b right graphs show data quantifying abnormal SeA formation in 8 to 16 embryos per group;

as described in detail in Example 2, below.

Figure 16A:
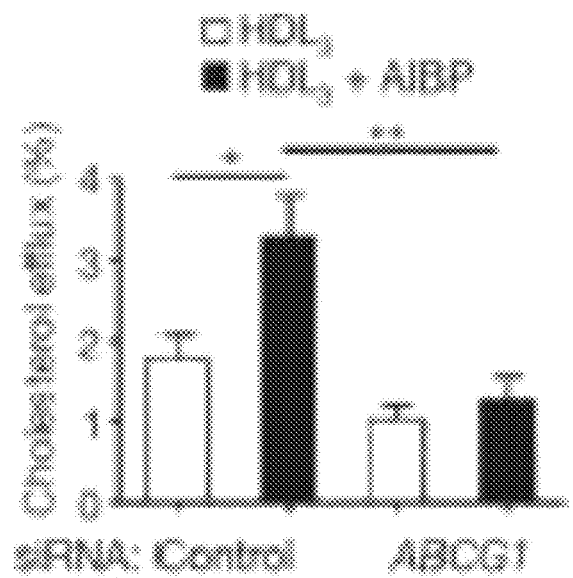
Figure 16B:
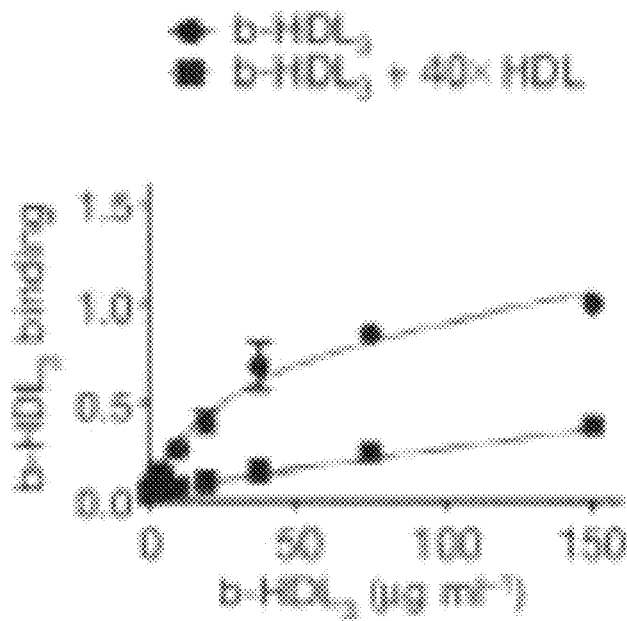
Figure 16C:
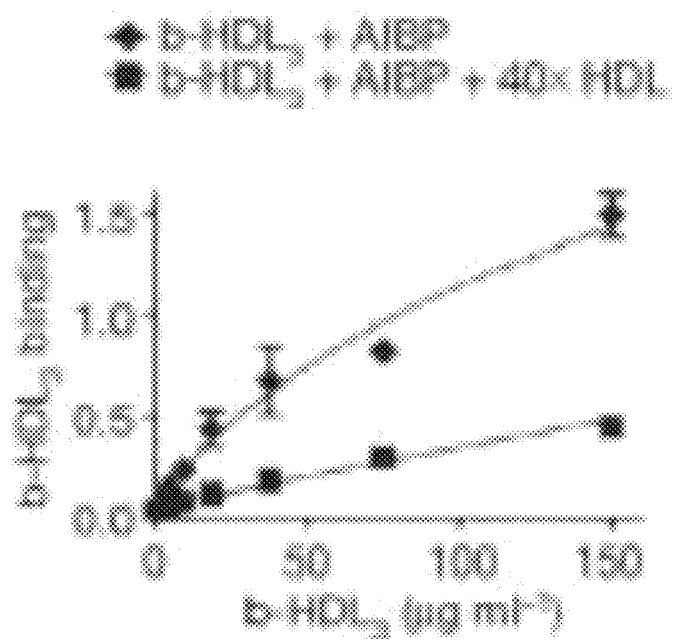
Figure 16D:
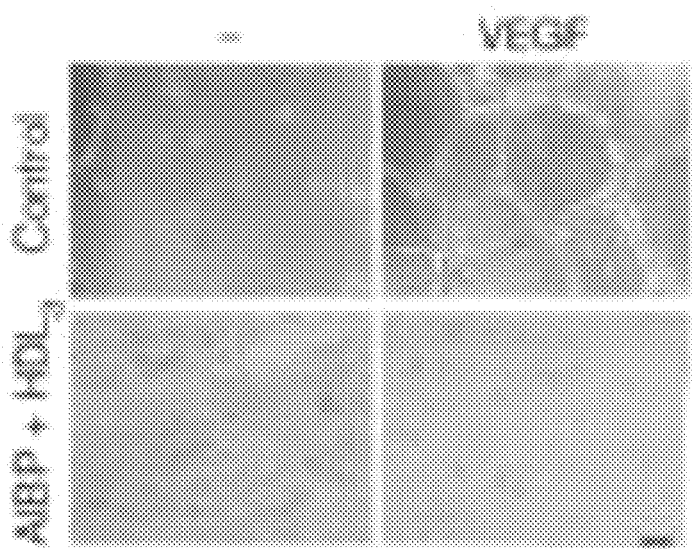
Figure 16E:
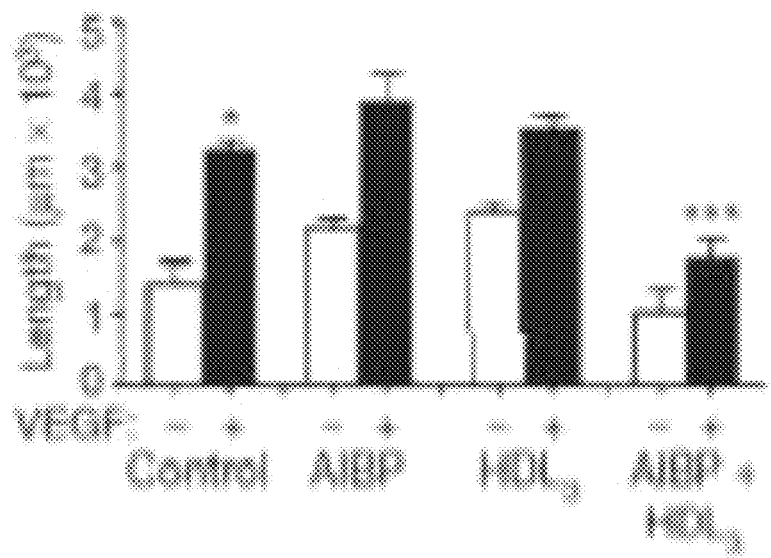
Figure 16F:
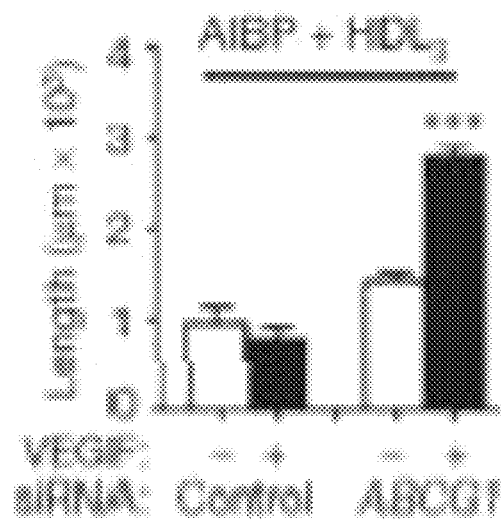
Figure 16G:
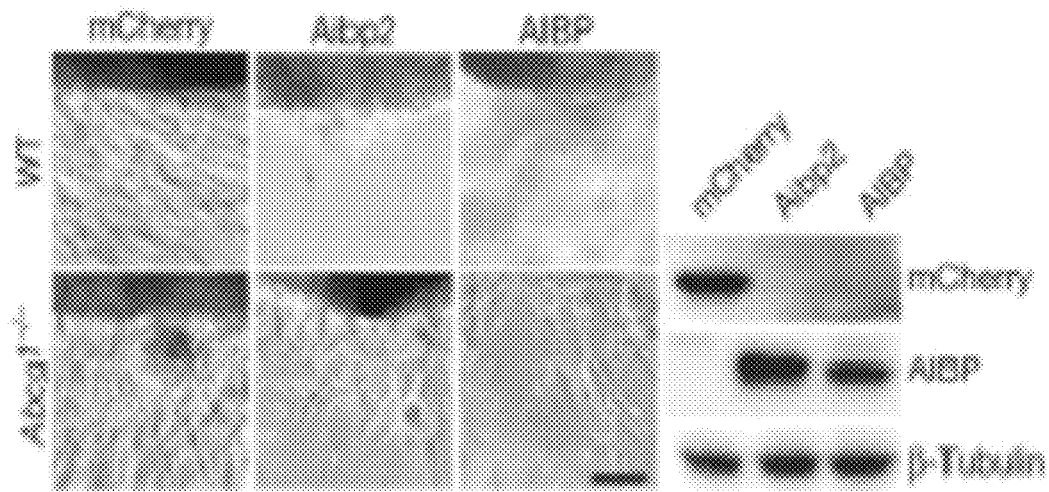
Figure 16H:
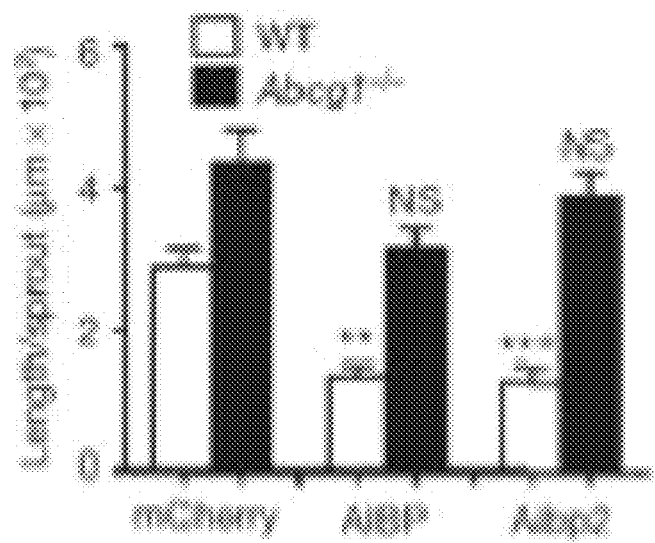

FIG. 16 in images and graphics shows the role of AIBP in cholesterol efflux from EC and in vitro angiogenesis:

FIG. 16a graphically illustrates hAIBP mediated-cholesterol efflux and effect of ABCG1 knockdown; HUVEC were transfected with control or ABCG1 siRNA, preloaded with $^3$H-cholesterol and incubated for 1 hour with 50 µg/ml $HDL_3$ in the presence or absence of 0.2 µg/ml hAIBP; and, efflux was measured as the $^3$H counts in the medium divided by the sum of $^3$H counts in the medium and the cell lysate;

FIG. 16b and FIG. 16c graphically illustrate the effect of hAIBP on $HDL_3$ binding to HUVEC: HUVEC were incubated on ice with the indicated concentration of biotinylated $HDL_3$ (b-$HDL_3$), in the presence or absence of hAIBP (at a 0.1:50 w/w hAIBP:$HDL_3$ ratio) and 40× excess of unlabeled HDL:

FIG. 16d illustrates images of the effect of hAIBP and $HDL_3$ on EC tube formation; HUVEC were preincubated with or without $HDL_3$+hAIBP for 4 hours; cells were then seeded on MATRIGEL™, in the presence or absence of VEGF, and imaged following a 12-hour incubation;

FIG. 16e graphically illustrates data from the experiment of FIG. 16d;

FIG. 16f graphically illustrates data showing the requirement for ABCG1 in hAIBP inhibition of angiogenesis; HUVEC were transfected with control or ABCG1 siRNA and assayed as in FIG. 16d;

FIG. 16g left images illustrates images a mouse aortic ring angiogenesis assay: aortic rings from C57BL6 and Abcg1$^{-/-}$ mice were embedded in MATRIGEL™; HEK293 cells transiently expressing mCherry, zAibp2 or hAIBP were inserted approximately 0.5 mm away from the aortic ring, and the plates were incubated with 10 ng/ml VEGF for 7 days, and the images show the edge of the aortic rings facing the HEK293 cell clusters, and FIG. 16g right images illustrate immunoblots showing expression of hAIBP and zAibp2, both detected with a Flag tag antibody, and mCherry in HEK293 cells;

FIG. 16h graphically illustrates data showing the length of aortic ring sprouts;

as described in detail in Example 3, below.

FIG. 17 in images and graphics show the effect of AIBP on HUVEC lipid rafts, VEGFR2 localization, dimerization and signaling:

FIG. 17a illustrates images of the effect of hAIBP and $HDL_3$ on lipid rafts; HUVEC were preincubated with $HDL_3$, hAIBP, or $HDL_3$+hAIBP for 4 hours, cells were stained for nuclei (blue, DAPI) and for lipid rafts (red, cholera toxin B (CTB) and anti-CTB antibody;

FIG. 17b graphically illustrates data from the experiment of FIG. 17a;

FIG. 17c graphically illustrates data showing the effect of hAIBP and $HDL_3$ on caveolin-1 and VEGFR2 surface localization: HUVEC were incubated with hAIBP and/or $HDL_3$ as in FIG. 17a, fixed and stained with antibodies to caveolin-1 and VEGFR2, and images were captured using TIRF microscopy and Pearson's coefficient was calculated to assess surface colocalization of VEGFR2 with caveolin-1;

FIG. 17d illustrates images of SDS-PAGE and Western blots showing VEGFR2 and caveolin-1 localization to lipid rafts: HUVEC were incubated with cholesterol-MβCD for six hours, followed by a 1 hour incubation with or without $HDL_3$+hAIBP, or a 30 min incubation with MβCD, and HUVEC lysates were separated into lipid rafts and non-lipid rafts fractions by ultracentrifugation, run on SDS-PAGE and blotted with VEGFR2 and caveolin-1 antibodies;

FIG. 17e illustrates images of SDS-PAGE and Western blots showing the effect of hAIBP and $HDL_3$ on VEGFR2 dimerization: HUVEC were preincubated with $HDL_3$ and/or hAIBP as in FIG. 16a, followed by a 20 min stimulation with VEGF, cells were treated with a crosslinking reagent, lysed and immunoprecipitated with a VEGFR2 antibody, and monomers and crosslinked dimers of VEGFR2 were visualized on Western blot;

FIG. 17f illustrates images showing the effect of hAIBP and $HDL_3$ on VEGFR2 endocytosis: HUVEC were preincubated with or without $HDL_3$+hAIBP for 4 hours, then stimulated with VEGF for 20 min, fixed and stained with antibodies to VEGFR2 (red) and the early endosome marker EEA-1 (green); yellow and white arrows point to the surface and endosomal localization of VEGFR2; and red dotted line traces cell contour;

FIG. 17g illustrates images of SDS-PAGE and Western blots showing the effect of hAIBP and $HDL_3$ on VEGFR2 signaling: HUVEC were preincubated with $HDL_3$ and/or hAIBP as in 2a, followed by a 20 min stimulation with VEGF, and total cell lysates were run on SDS-PAGE and probed as indicated;

as described in detail in Example 3, below.

FIG. 18 in images and graphics show the effect of Aibp deficiency on zebrafish cholesterol, membrane lipid order, Vegfr2 signaling and angiogenesis:

FIG. 18a illustrates images of zebrafish embryos showing the tissue distribution of zaibp2 mRNA in the embryos; embryos at 24 hpf were fixed and WISH was performed with antisense myod and zaibp2 probes;

FIG. 18b and FIG. 18c illustrates free cholesterol levels in zaibp2 morphants:

FIG. 18b illustrates images of zebrafish embryos injected with either control MO or zaibp2 MO; twenty four hpf control and zaibp2 morphants were stained with filipin to detect free cholesterol in embryos;

FIG. 18c graphically illustrates data of free cholesterol levels determined by gas chromatography (GC), where zebrafish embryos at 24 hpf, the trunk area (without yolk) was dissected, total lipids extracted, and free cholesterol levels determined;

FIG. 18d illustrates images showing the effect of zaibp2 MO on SeA membrane lipid order; Tg(flk1:ras-cherry)$^{s896}$ embryos were injected with control or zaibp2 MO as in 3b and at 24 hpf were stained with 5 μM Laurdan; in the same embryos, confocal images of mCherry fluorescence (bottom images) and the multiphoton images of Laurdan fluorescence were captured, and the multiphoton results (top row images) are displayed as pseudocolored GP (generalized polarization, a measure of the membrane lipid order) images, cropped to show only the vasculature, i.e. mCherry-positive areas;

FIG. 18e graphically illustrates data of GP values in the areas corresponding to tip and stalk cells of growing SeA and the dorsal aorta (DA) as indicated in FIG. 18d;

FIG. 18f illustrates images of SDS-PAGE and immunoblots showing phosphorylation of signaling proteins: lysates of 24 hpf control (8 ng control MO), zaibp2 (8 ng zaibp2 MO) and abca1/g1 (4 ng abca1 MO+4ng abcg1 MO) morphants were separated on SDS-PAGE and immunoblotted as indicated;

FIG. 18g illustrates images of zebrafish embryos showing angiogenic defects in zaibp2 morphants: one-cell stage Tg(fli1:egfp)$^{y1}$ zebrafish embryos were injected with 8 ng of either control or zaibp2 MO; the images are of SeA in 30 hpf embryos (top row), and SeA (middle row) and of SIV (bottom row) in 3 dpf embryos; arrows point to dysregulated sprouts;

FIG. 18h graphically illustrates data showing the quantification of the number of embryos with normal and abnormal angiogenesis (SeA with ectopic branching); The abnormal angiogenesis was partially rescued by co-injection of 40 pg of zaibp2 mRNA lacking the MO targeting site;

as described in detail in Example 3, below.

FIG. 19 in images and graphics show the effects of Aibp and Abca1/Abcg1 deficiency on zebrafish angiogenesis:

FIG. 19a illustrates images of zebrafish embryos using a mosaic expression analysis of EC branching in control, zaibp2 and abca1/abcg1 knockdown embryos; at 4 hpf, cells were isolated from donor embryos and transplanted into recipient embryos; recipient embryos were analyzed at 3 dpf; arrows point to aberrant ectopic branches/sprouts;

FIG. 19b graphically illustrates data showing numbers of ectopic branches/filopodial projections per SeA;

FIG. 19c illustrates images of angiogenic defects in abca1/abcg1 morphants: one-cell stage embryos were injected with 8 ng of control MO, 8 ng zaibp2 MO, or 4 ng abca1 MO+4 ng abcg1 MO; images of SeA (30 hpf) and SIV (3 dpf) are shown;

FIG. 19d illustrates images of zebrafish embryos where knockdown of abca1/g1 cancels the effect of zAibp2 overexpression: one-cell stage embryos were injected with 2 nl of 100 ng/μl myog:zaibp2-mCherry, myog:zaibp2-mCherry+abca1/g1 MO, or myog:mCherry; arrow points to an aberrant SeA at the site of zAibp2-mCherry expression;

FIG. 19e graphically illustrates data showing abnormal SeA formation (as a percent of SeA sprouting) as quantified in 8 to 16 embryos per group;

as described in detail in Example 3, below.

Figure 20:
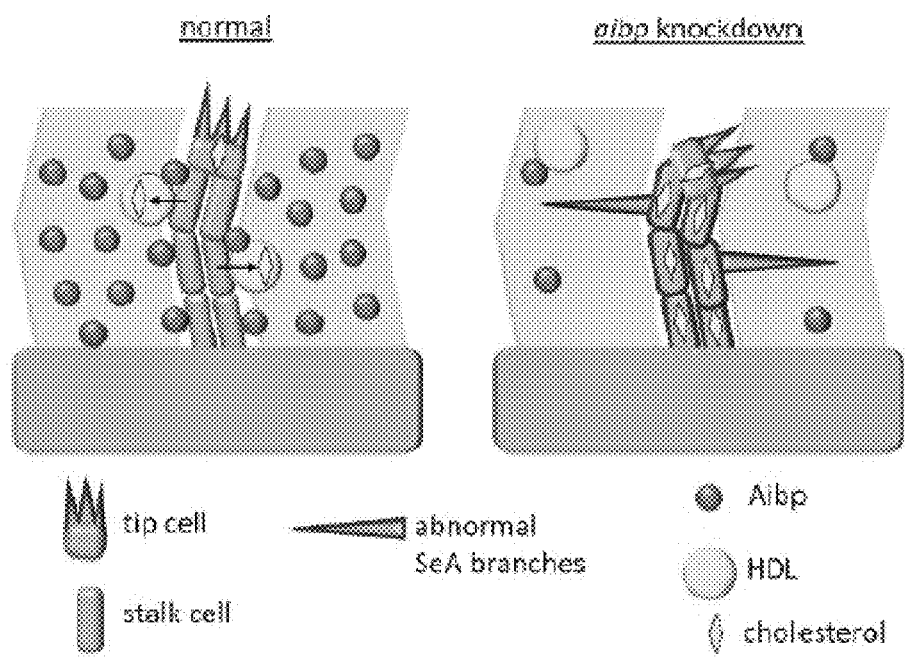

FIG. 20 schematically illustrates the hypothesis that expression of Aibp2 in somites (tan-shaded areas) but not in the inter-somitic space accelerates cholesterol efflux from EC to HDL; because cholesterol removal from the plasma membrane reduces lipid rafts and inhibits Vegfr2 signaling, the tip cell is guided in the direction where Aibp2 is least present; in aibp2 knockdown embryos (right image) defective cholesterol efflux leads to a higher abundance of lipid rafts (depicted as dark green boundaries of EC in right-hand panel) and enhanced Vegfr2 signaling, which result in misguided growth and ectopic branching of SeA, as further discussed in Example 3, below.

Figure 21A:
Figure 21B:
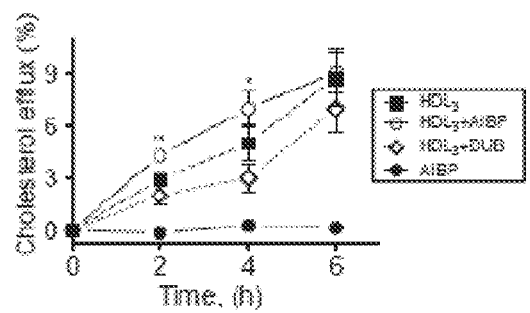
Figure 21C:
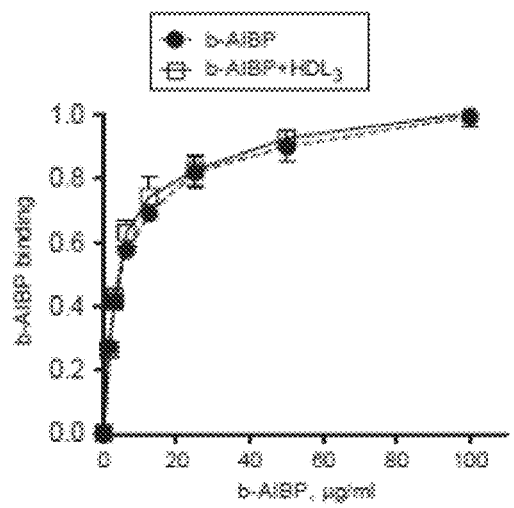

FIG. 21a and FIG. 21b:

FIG. 21a illustrates images of siRNA in ABCG1 knockdown in HUVEC: the blot confirms the ABCG1 knockdown in cells used in the experiments of FIG. 16a;

FIG. 21b graphically illustrates data showing the kinetics of cholesterol efflux from HUVEC to $HDL_3$: HUVEC were preloaded with $^3H$-cholesterol and then incubated for 2, 4 or 6 hours with 50 μg/ml $HDL_3$ in the presence or absence of 0.2 μg/ml human AIBP or 0.2 μg/ml deubiquitinase (DUB, a non-relevant protein of the same molecular weight as AIBP); The cholesterol efflux was measured as described Example 3, below; note that AIBP in absence of $HDL_3$ did not induce cholesterol efflux from HUVEC. Mean±SD; n=3. *, $p<0.05$; **, $p<0.01$;

FIG. 21c: graphically illustrates data of human AIBP binding to HUVEC: HUVEC were incubated on ice with the indicated concentrations of biotinylated AIBP (b-AIBP), in the presence or absence of $HDL_3$ (at a 2:1 w/w AIBP:$HDL_3$ ratio), and the b-AIBP binding was determined by a chemiluminescent assay; a non-linear regression fit of both binding curves yielded $K_d=(1.1±0.4)×10^{-7}$ M for AIBP/HUVEC binding.

Figure 22A:
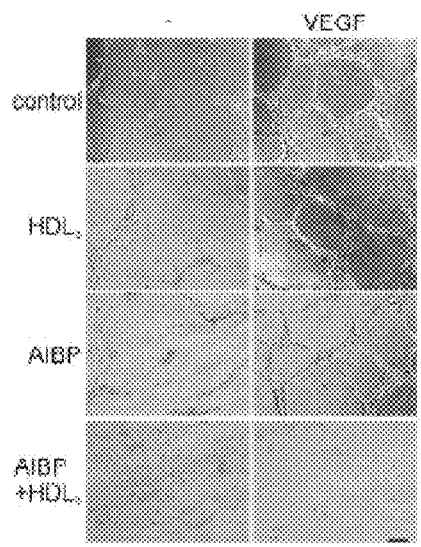

FIG. 22A: illustrates images showing the effect of human AIBP and $HDL_3$ on EC tube formation: this figure is an extension of FIG. 16d, to illustrate the results shown on the graph of FIG. 16e; for that reason, the top and bottom row images in this figure are identical to the images in FIG. 16d: HUVEC were preincubated with 50 μg/ml $HDL_3$, 0.1 μg/ml AIBP, or 50 μg/ml $HDL_3$+0.1 μg/ml AIBP, and cells were then seeded on MATRIGEL™, in the presence or absence of 20 ng/ml VEGF, and imaged following a 12 hour incubation.

Figure 22B:
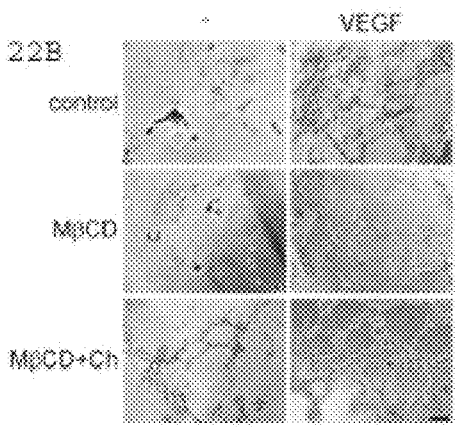
Figure 22C:
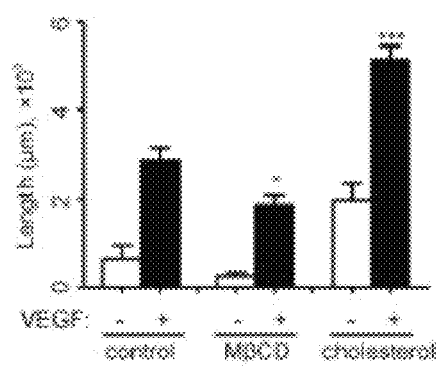

FIG. 22B and FIG. 22C: FIG. 22B illustrates images showing the effect of MβCD and cholesterol-MβCD on EC tube formation: HUVEC were preincubated with 10 mM MβCD for 30 min or 20 μg/ml cholesterol-MβCD for 4 hours; cells were then seeded on MATRIGEL™ in the presence or absence of 20 ng/ml VEGF, and imaged following a 6 hour incubation; scale, 100 μm. Mean±SD; n=3. *, $p<0.05$; ***, $p<0.001$ vs. VEGF/control; FIG. 22C graphically illustrates data of EC tube formation length in control, MβCD and cholesterol-MβCD samples;

FIG. 23a and FIG. 23b: illustrate total internal reflection fluorescence (TIRF) microscopy images of the effect of human AIBP and $HDL_3$ on caveolin-1 and VEGFR2 surface localization:

FIG. 23a illustrates the results shown on the graph of FIG. 17c: HUVEC were treated as in FIG. 17a, fixed and stained with antibodies to caveolin-1 (green) and VEGFR2 (red), and images were captured using TIRF microscopy; scale, 10 μm;

FIG. 23b illustrates the negative control, where HUVEC were stained with a mouse IgG1 isotype (replacing the mouse caveolin-1 antibody) and a rabbit anti-GFP antibody (replacing the VEGFR2 antibody), followed by secondary antibodies, as further discussed in Example 3, below.

Figure 23:
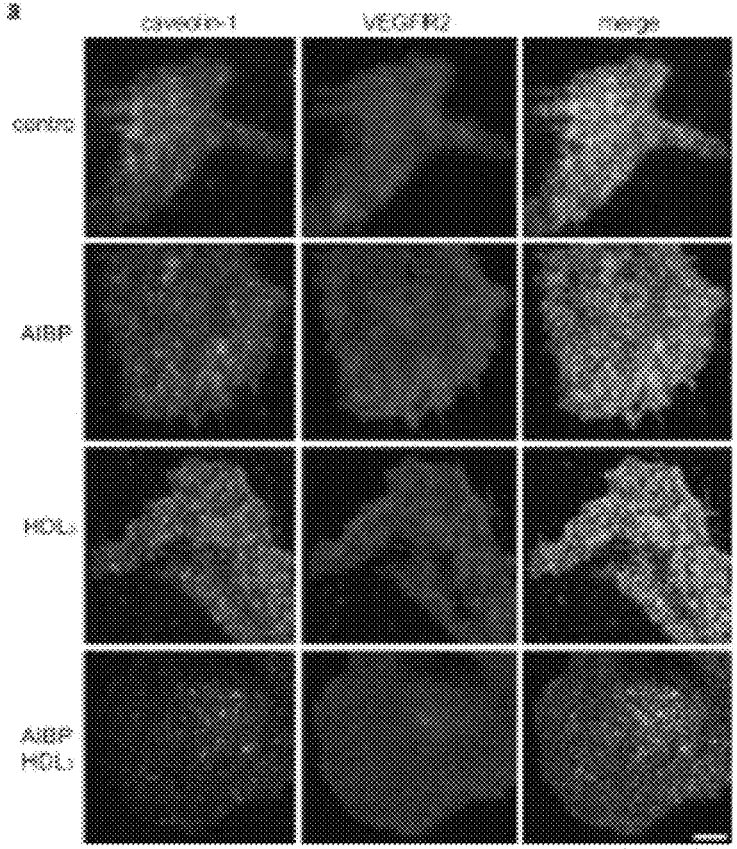
Figure 23:
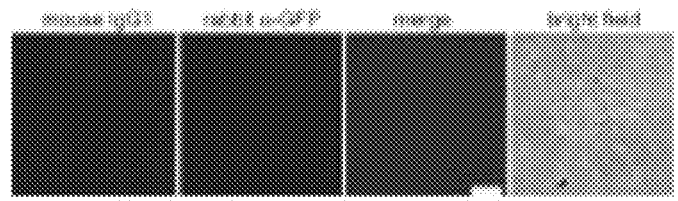
Figure 24A:
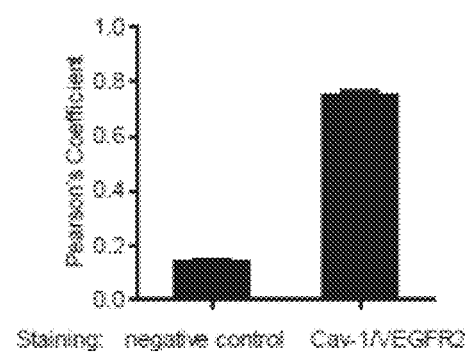

FIG. 24A: graphically illustrates the non-specific green and red signals of FIG. 23a and FIG. 23b, showing that there was no colocalization of non-specific green and red signals as shown with Pearson's coefficient calculations, as further discussed in Example 3, below.

Figure 24B:
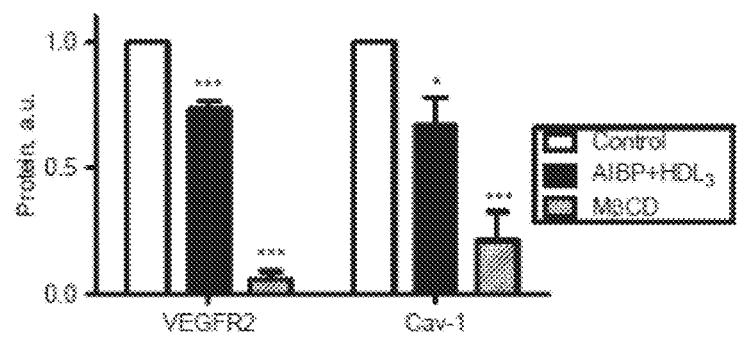

FIG. 24B: graphically illustrates the effect of human AIBP and $HDL_3$ on VEGFR2 and caveolin-1 localization to lipid rafts. This supplementary figure is the quantification of VEGFR2 and caveolin-1 in the lipid raft fraction (LR) shown in FIG. 2d. Equal protein amounts of each sample were loaded on gel. Mean±SD. The experiment was repeated 5 times for $HDL_3$+AIBP and 3 times for MβCD treatments; *, $p<0.05$; ***, $p<0.001$, as further discussed in Example 3, below.

Figure 25:
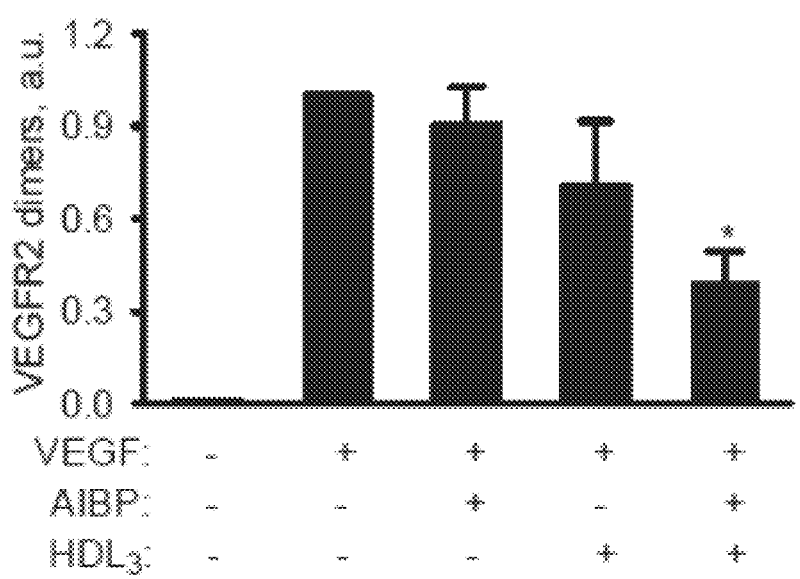

FIG. 25: graphically illustrates the effect of human AIBP and $HDL_3$ on VEGFR2 dimerization: this figure is the quantification of the VEGFR2 dimerization experiment shown in FIG. 17e, calculated as dimer/(monomer+dimer). Mean±SD (n=3); *, $p<0.05$, as further discussed in Example 3, below.

FIG. 26: graphically illustrates the effect of human AIBP and $HDL_3$ on VEGFR2 endocytosis: this figure is an extension of FIG. 17f, to show the results of additional treatment conditions, and for that reason, the top two and the bottom row images in this supplementary figure are identical to the images in FIG. 17f:

FIG. 26a illustrates images of HUVEC that were preincubated with 50 μg/ml $HDL_3$, 0.1 μg/ml AIBP, or 50 μg/ml/ml $HDL_3$+0.1 μg/ml AIBP for 4 hours, then stimulated with 50 ng/ml VEGF for 20 min, fixed and stained with antibodies to VEGFR2 (red) and the early endosome marker EEA-1 (green); yellow arrows point to the surface localization of VEGFR2 and white arrows point to the endosomal localization of VEGFR2; scale, 10 μm;

FIG. 26b graphically illustrates the quantification of VEGFR2 and EEA-1 colocalization from FIG. 26a; mean±SE (n=23 to 55); ****, $p<0.0001$;

as further discussed in Example 3, below.

Figure 27:
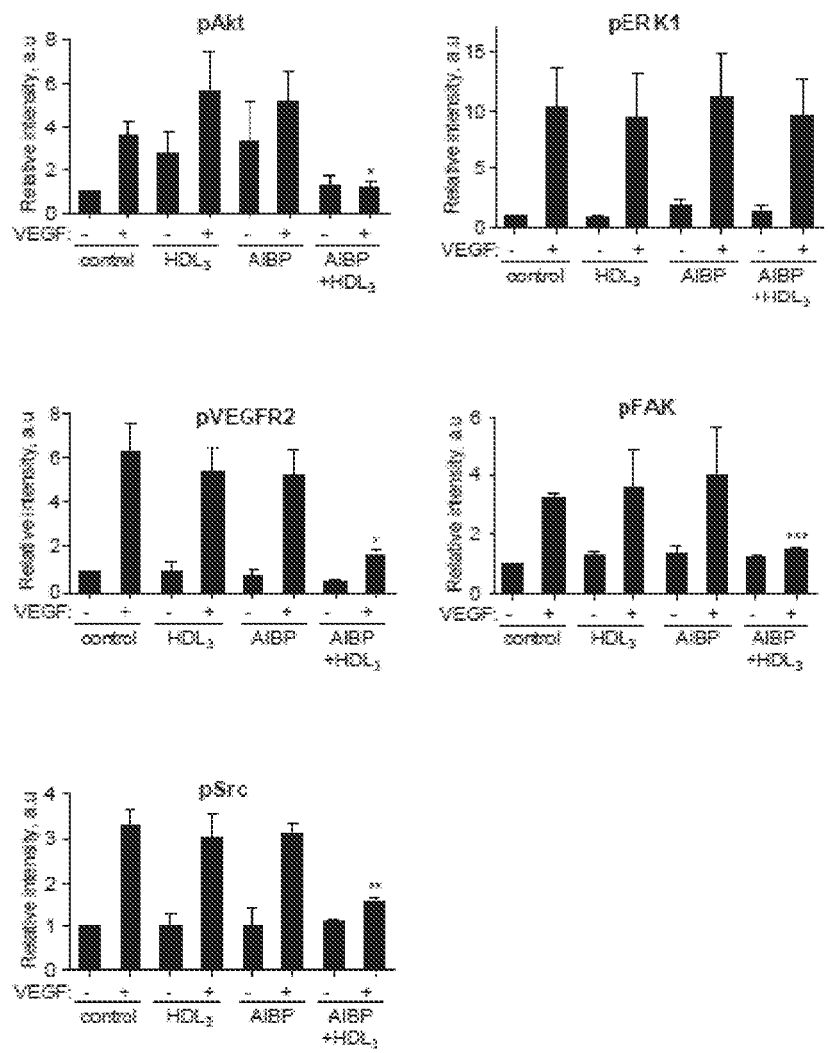

FIG. 27: graphically illustrates the effect of human AIBP and $HDL_3$ on VEGF-induced signaling in HUVEC: this figure is the quantification of the signaling experiment shown in FIG. 17g; normalized to β-tubulin and then to control (without VEGF); mean±SD (n=3); *, $p<0.05$; , $p<0.01$; *, $p<0.001$, as further discussed in Example 3, below.

FIG. 28 in images and graphically illustrate that the addition of cholesterol reduces the effect of human AIBP and HDL$_3$ on VEGF-induced signaling in HUVEC:

FIG. 28a illustrates HUVEC preincubated with AIBP and HDL$_3$ as in FIG. 17g, followed by a one hour incubation with or without 20 μg/ml cholesterol-MβCD; the cells were then stimulated for 20 min with 50 ng/ml VEGF, and cell lysates were run on SDS-PAGE, blotted and probed as indicated;

FIG. 28b graphically illustrates the quantification of blot results; normalized to GAPDH and then to control, mean±SE (n=5); *, p<0.05;

as further discussed in Example 3, below.

Figure 29A:
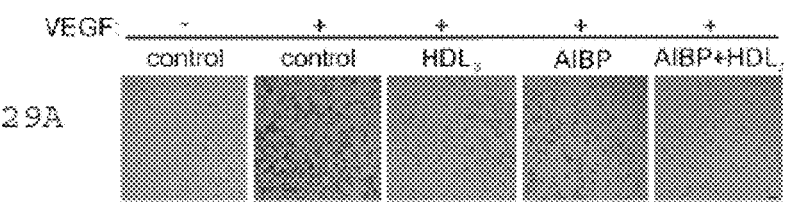
Figure 29B:
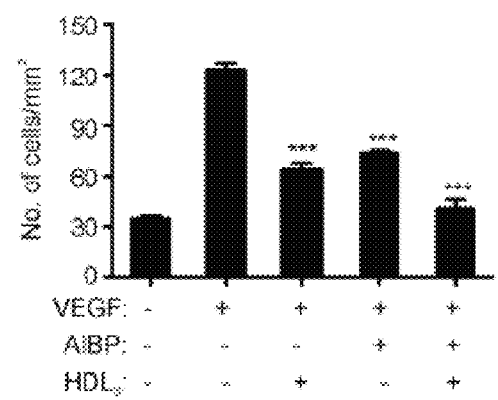

FIG. 29 in images and graphically illustrate the effect of human AIBP on VEGF-induced HUVEC migration:

FIG. 29A illustrates images of HUVEC preincubated with 50 μg/ml HDL$_3$, 0.1 μg/ml AIBP, or 50 μg/ml HDL$_3$+0.1 μg/ml AIBP for 4 hours, subjected to a migration assay as described in methods, Example 3, below; mean±SE (n=5). ***, p<0.001;

FIG. 29B graphically illustrates the data imaged in FIG. 29A, as further discussed in Example 3, below.

Figure 30:
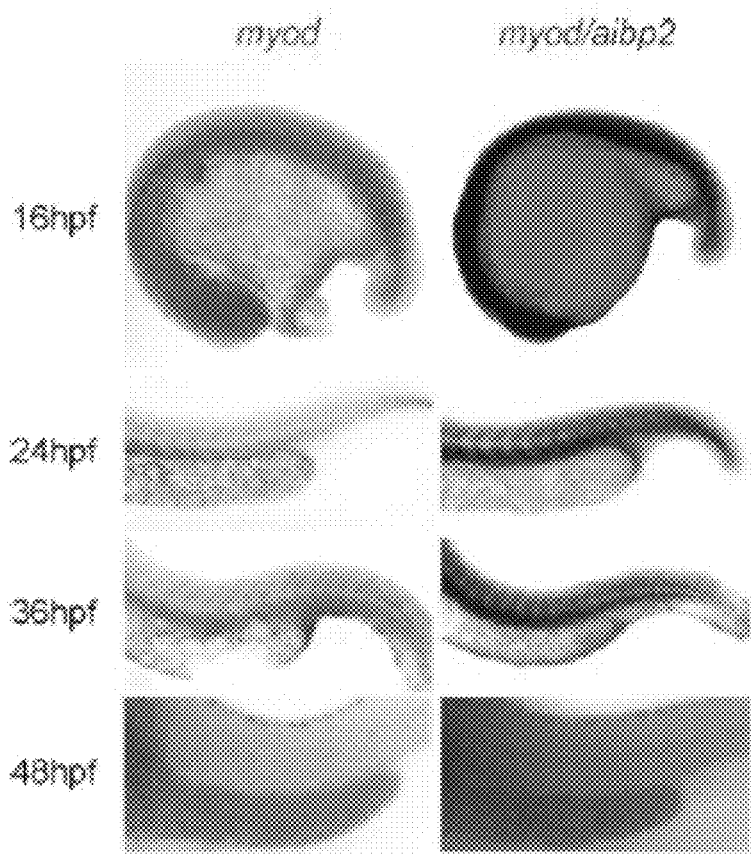

FIG. 30 illustrates images showing the expression of aibp2 mRNA in zebrafish embryos at 16 to 48 hpf; the images in this figure are to supplement FIG. 18a, which shows only a 24 hpf time point, as further discussed in Example 3, below.

Figure 31:
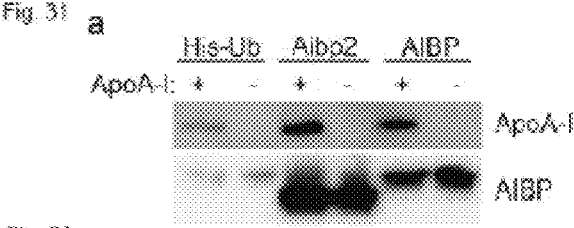
Figure 31:
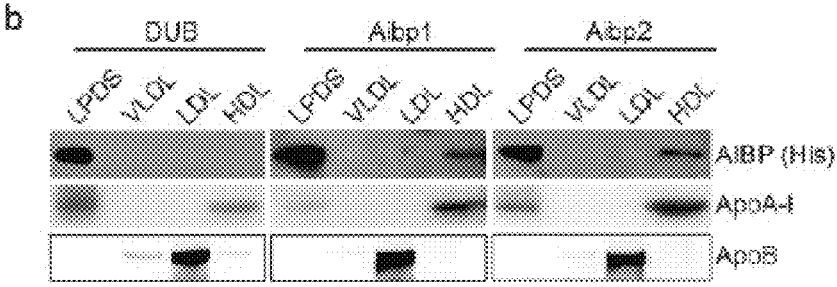
Figure 31:
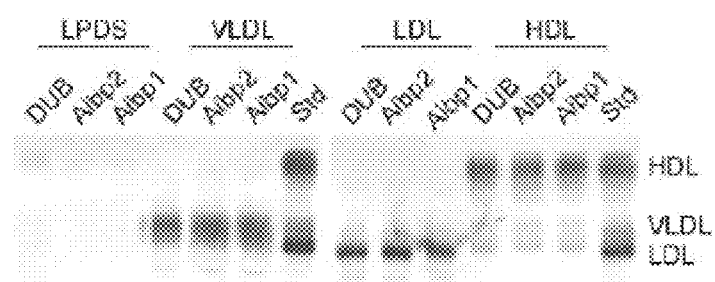

FIG. 31 illustrates images of Zebrafish Aibp binding to human ApoA-I:

FIG. 31a illustrates an SDS-PAGE and immunoblot where three pg of purified human ApoA-I were mixed with 3 μg of His-tagged zebrafish Aibp2 or human AIBP and then immunoprecipitated with an anti-His antibody; His-tagged ubiquitin was used as a negative control, the blots were probed as indicated;

FIG. 31b illustrates an SDS-PAGE and immunoblot showing Zebrafish Aibp binding to human HDL, where five μg of purified His-tagged DUB, Aibp1 or Aibp2 were incubated with 1 ml of human plasma overnight at 4° C.; ultracentrifugation was performed to separate lipoprotein fractions; and different fractions of lipoproteins were run on SDS-PAGE and immunoblotted with indicated antibodies;

FIG. 31c illustrates an agarose gel electrophoresis of human lipoprotein fractions separated by ultracentrifugation, stained with FatRed; DUB, deubiquitinase; Std, human standard plasma; LPDS, lipoprotein-deficient serum, as further discussed in Example 3, below.

Figure 32A:
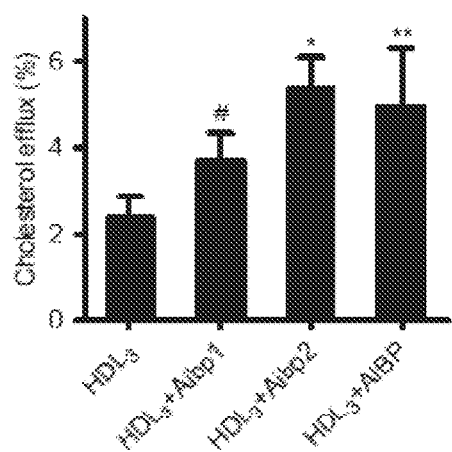
Figure 32B:
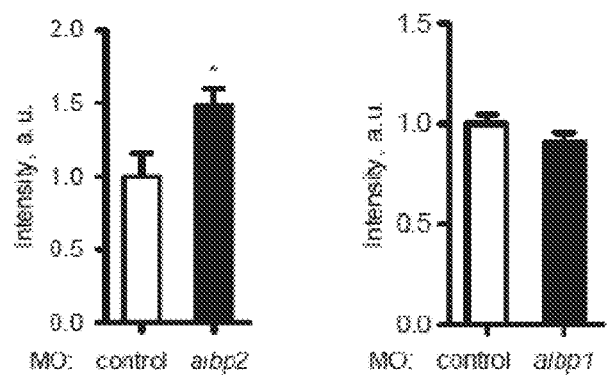

FIG. 32A and FIG. 32B:

FIG. 32A graphically illustrates the effect of zebrafish Aibp on cholesterol efflux from HUVEC to HDL$_3$: HUVEC were preloaded with $^3$H-cholesterol and then incubated for 1 hour with 50 μg/ml HDL$_3$ in the presence or absence of 0.2 μg/ml human AIBP, zebrafish Aibp1 or zebrafish Aibp2; the media and cell lysates were collected and $^3$H counts were measured; efflux was measured as the $^3$H counts in the media divided by the sum of $^3$H counts in the media and the cell lysates; mean±SD; n=3. **, p<0.01; *, p<0.05; #, p=0.08;

FIG. 32B graphically illustrates free cholesterol levels in aibp1 morphants: one-cell stage AB zebrafish embryos were injected with 8 ng of either control MO, aibp1 MO or aibp2 MO targeting ATG translation site; twenty four hpf embryos were fixed and stained with filipin to detect free cholesterol in embryos; intensities of filipin fluorescence in embryos (without yolks) were quantified. n=12-18. *, p<0.05;

as further discussed in Example 3, below.

Figure 33:
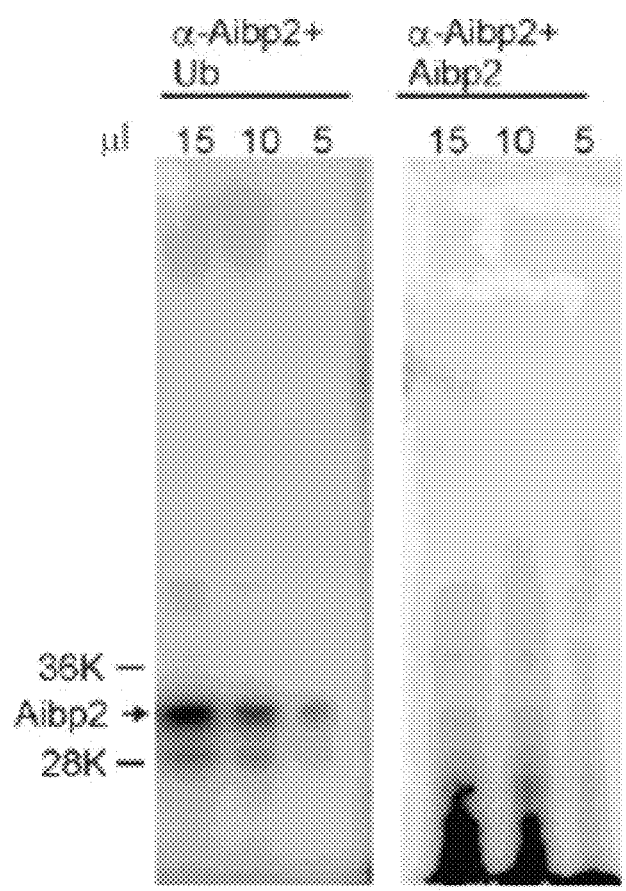

FIG. 33 illustrates an SDS-PAGE and immunoblot showing the specificity of a zebrafish Aibp2 antibody: a polyclonal antibody against Aibp2 (guinea pig post-immune serum) was used to probe zebrafish homogenates; fifteen, 10 and 5 μl of the homogenates were loaded on an SDS gel, blotted and probed with the antibody, preincubated with 10 μg of either ubiquitine (Ub) or with Aibp2 (both recombinant proteins were produced from the same expression vector and under the same conditions); the blots were visualized with an anti-guinea pig IgG conjugated with HRP and a chemiluminescent substrate; as further discussed in Example 3, below.

Figure 34A:
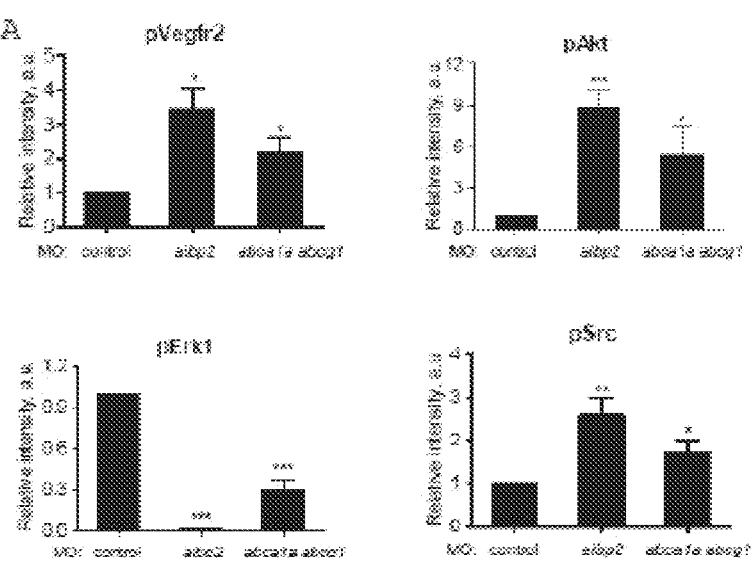
Figure 34B:
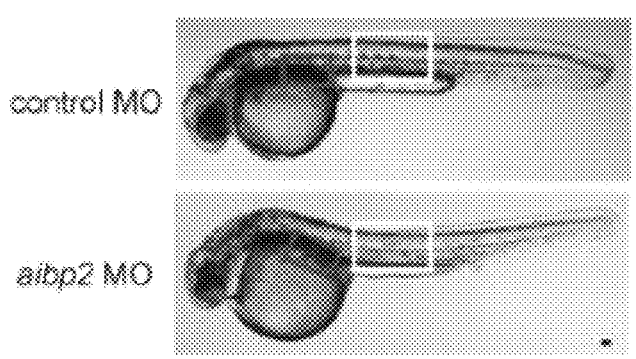

FIG. 34A and FIG. 34B:

FIG. 34A graphically illustrates the quantification of the immunoblot experiment shown in FIG. 18f, showing the phosphorylation of signaling proteins in zebrafish lysates; Erk1 is the p44 MAPK; there were no statistically significant differences in the pErk2 (p42) values; normalized to β-tubulin and then to control; mean±SD (n=3 to 7). *, p<0.05; , p<0.01; *, p<0.001;

FIG. 34B illustrates low magnification, bright field images showing the area of fluorescent imaging of SeA (white box) and SIV (red box), which are displayed in FIG. 18g; scale, 25 μm, as further discussed in Example 3, below.

FIG. 35 illustrates dysregulated SeA and SIV angiogenesis in aibp2 morphants (splicing site):

FIG. 35a, FIG. 35b, and FIG. 35c illustrate where one-cell stage Tg(fli1:EGFP) zebrafish embryos were injected with 8 ng of either control MO or aibp2 MO2, targeting a splicing site; and the images of SeA (FIG. 35a, FIG. 35b) and SIV (FIG. 35c) were captured 3 days after MO injection; arrows point to dysregulated sprouts; scale, 50 μm;

FIG. 35d illustrate upper diagram schematically shows the targeted splicing site and gel (lower image) showing corresponding PCR products; PF and PR indicate the primers used for the amplification;

as further discussed in Example 3, below.

Figure 36:
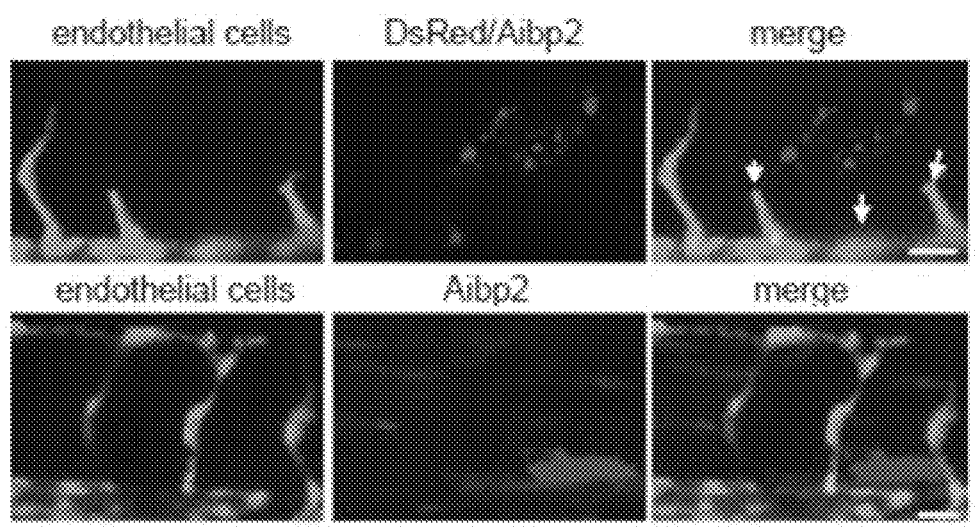

FIG. 36 illustrates the ectopic expression of Aibp2 inhibits SeA growth: one-cell stage Tg(fli1:egfp)$^{y1}$ embryos were injected with 2 nl of 100 ng/μl DNA constructs for myog:Gal4, DsRed:10×UAS:Aibp2 or myog:Gal4, DsRed:10× UAS expression; images were captured at 30 hpf; arrows point to aberrant SeA growth, close to the sites of DsRed (and Aibp2) expression; scale, 25 μm; as further discussed in Example 3, below.

Figure 37A:
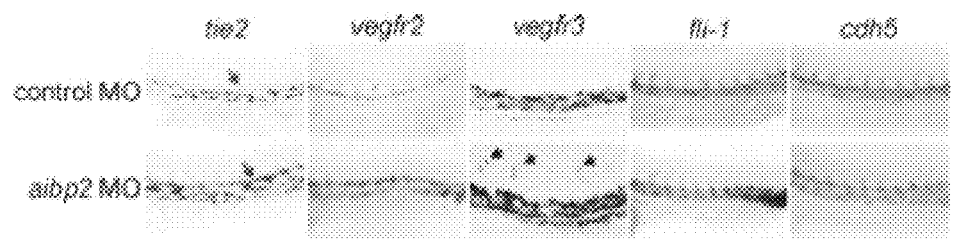
Figure 37B:
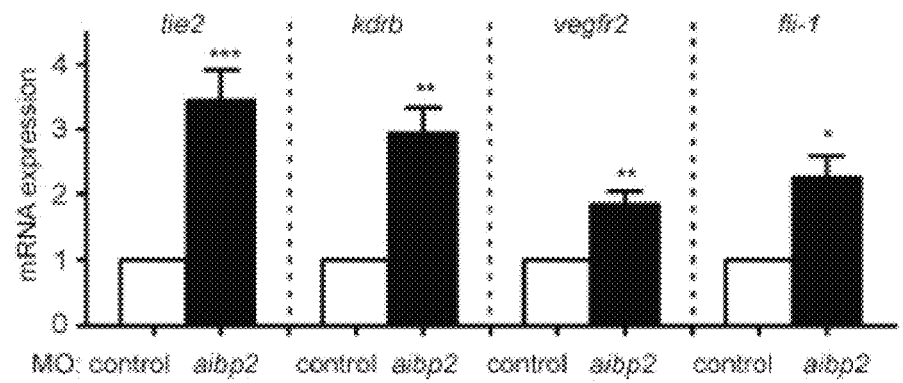

FIG. 37A and FIG. 37B:

FIG. 37A illustrates a WISH analysis of genes involved in angiogenesis: twenty four hpf control and aibp2 morphants were fixed and hybridized with probes to tie2 (GeneID: 30747), vegfr2/kdrl (GeneID:796537), and fli1 (GeneID: 30619); a 28 hpf time point was used for vegfr3/flt4 (GeneID:30121). cdh5 (Gene ID: 445471) at 24 hpf was used as an internal control; red arrows point to tie2 expression in the dorsal aorta, and orange brackets show the posterior cardinal vein; black arrows show increased expression of vegfr3 in the SeA of a aibp2 morphant;

FIG. 37B graphically illustrates the expression of genes involved in angiogenesis: total RNA was isolated from 24 hpf control and aibp2 morphants and qRT-PCR was performed with primers for tie2 (GeneID:30747), kdrb: (GeneID:554230), vegfr2/kdrl (GeneID:796537), and fli1 (GeneID:30619); the mRNA levels were normalized to β-actin (Gene ID: 57934) mRNA and then to the values in control embryos; the results are from a pool of 50 embryos per group, 3 to 4 replicates.*, p<0.001; , p<0.01; *, p<0.05;

as further discussed in Example 3, below.

Figure 38C:
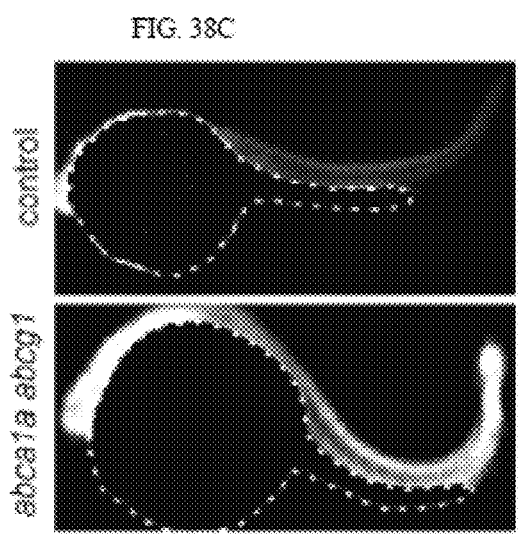
Figure 38D:
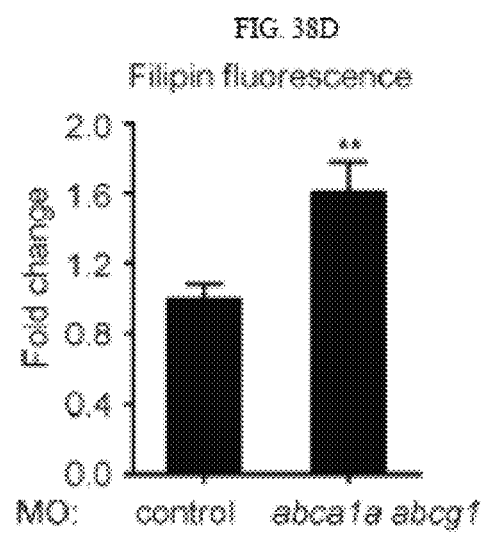

FIG. 38A and FIG. 38B:

FIG. 38A-D illustrate images and a graphic showing the specificity of abcg1 and abca1a MOs:

FIG. 38A illustrates images of one-cell stage embryos injected with mRNA encoding mCherry-tagged N-terminus of Abcg1, with control or abcg1 MO; images were captured at 12 hpf;

FIG. 38B illustrates images showing one-cell stage embryos injected with mRNA encoding mCherry-tagged N-terminus of Abca1a, with control or abca1a MO. Images were captured at 4 hpf; scale, 100 μm;

FIG. 38C-D illustrate images and graphs showing free cholesterol levels in abca1a/abcg1 morphants:

FIG. 38C illustrates representative images of 24 hpf control and abca1a/abcg1 morphants stained with filipin to detect free cholesterol; note the yolks are artificially masked;

FIG. 38D graphically illustrates data showing the intensity of filipin fluorescence in images shown in panel FIG. 38B-a (without yolks) as quantified in 8 to 10 embryos per group; **, p<0.01;

as further discussed in Example 3, below.

Figure 39A:
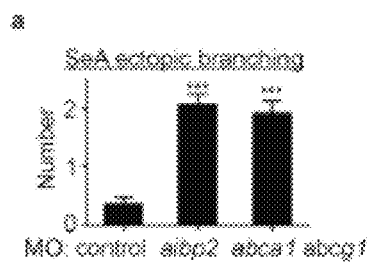
Figure 39B:
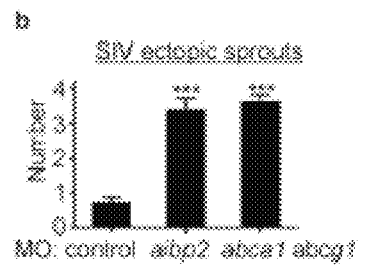
Figure 39C:
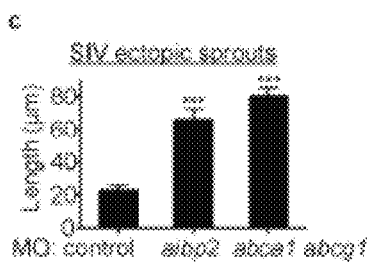
Figure 39D:
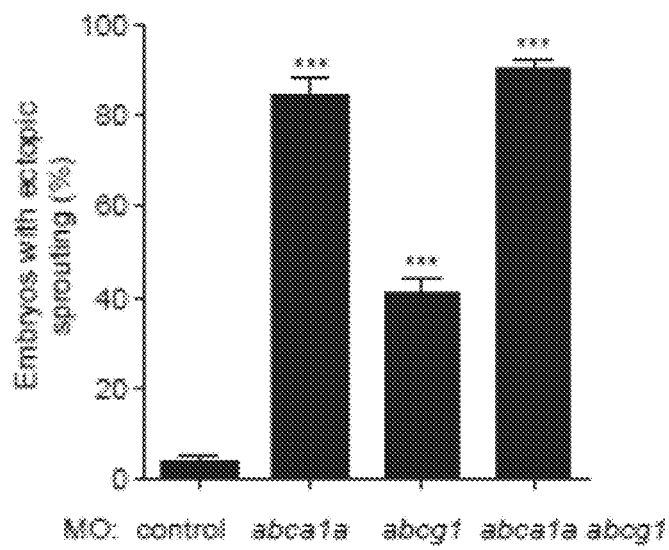

FIG. 39A-D illustrate:

FIG. 39A, 39B, 39C graphically illustrate quantitative data for FIG. 19c; the graphs show numbers of SeA ectopic branches and numbers and length of SIV ectopic sprouts from 5-12 embryos; ***, p<0.001;

FIG. 39D graphically illustrates quantification of the number of embryos with normal and abnormal angiogenesis (SeA with ectopic branching) resulting from injection of 8 ng control, abca1a or abcg1 MO, or 4 ng abca1a MO+4 ng abcg1 MO. 79-178 embryos per group; ***, p<0.001, as further discussed in Example 3, below.

Figure 40A:
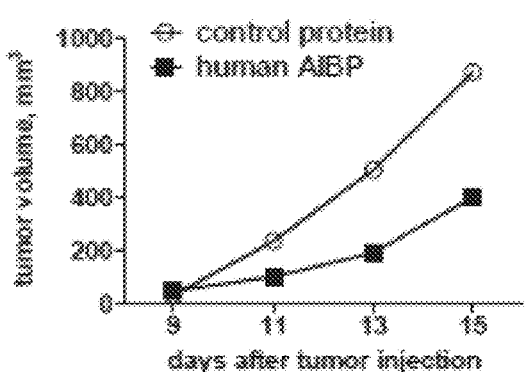
Figure 40B:
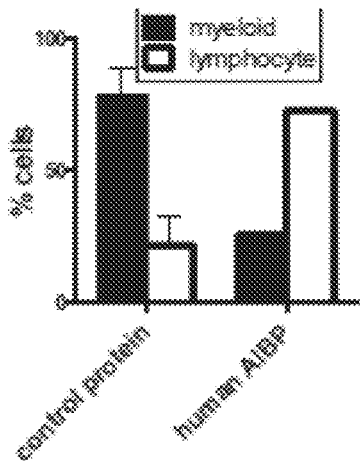

FIG. 40A and FIG. 40B: FIG. 40A graphically illustrates tumor growth in mice as inhibited by injections of human AIBP; FIG. 40B graphically illustrates data showing that injections of AIBP inhibit proliferation of myeloid cells and boost proliferation of lymphocytes; as further discussed in Example 4, below.

Figure 41:
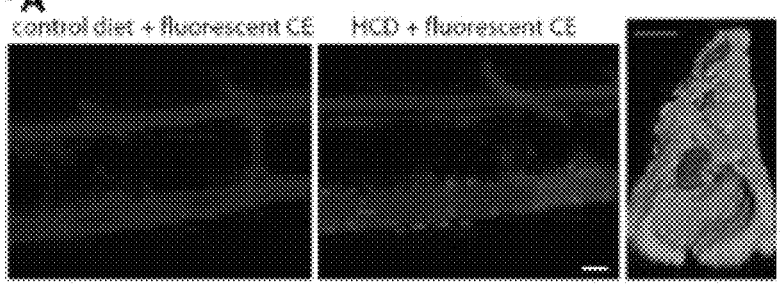
Figure 41:
Figure 41:
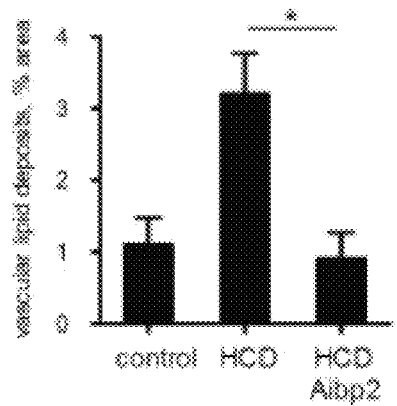

FIG. 41 illustrates data showing that the conditional expression of Aibp in transgenic zebrafish abolishes high cholesterol diet (HCD)-induced vascular lipid accumulation:

FIG. 41A illustrates images of HCD-induced vascular lipid accumulation in control versus HCD conditions: red, fluorescent lipid tracer; green, GFP expressed in endothelial cells;

FIG. 41B schematically illustrates an exemplary DNA construct used to generate a transgenic zebrafish: gene expression is induced by heat shock, i.e., placing a zebrafish in a 37° C. water for 1 hour (normal maintenance temperature is 28° C.);

FIG. 41C graphically illustrates data showing that vascular lipid accumulation (as vascular lipid deposits as a percent of area) as induced in zebrafish by HCD feeding was abolished in animals with forced Aibp expression.

Figure 42:
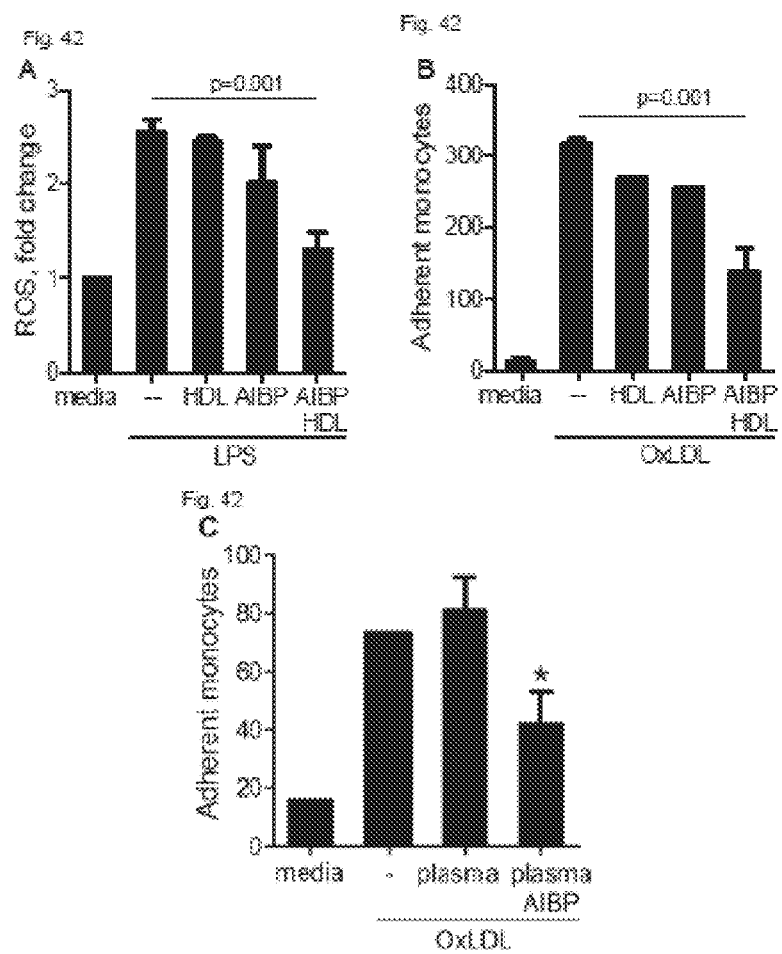

FIG. 42 graphically illustrates AIBP+HDL inhibit ROS generation and monocyte adhesion to endothelial cells:

FIG. 42A and FIG. 42 B: graphically illustrate data showing human aortic endothelial cells (HAEC) stimulated with LPS (FIG. 42A) or OxLDL (FIG. 42B), then treated with HDL, AIBP or their combination, and used in ROS generation (FIG. 42A) and THP-1 monocyte adhesion (FIG. 42B) assays;

FIG. 42C graphically illustrates data from ten plasma samples from patients with cardiovascular disease were tested in a monocyte adhesion assay; adding recombinant AIBP to plasma samples significantly reduced monocyte adhesion.

Figure 43:
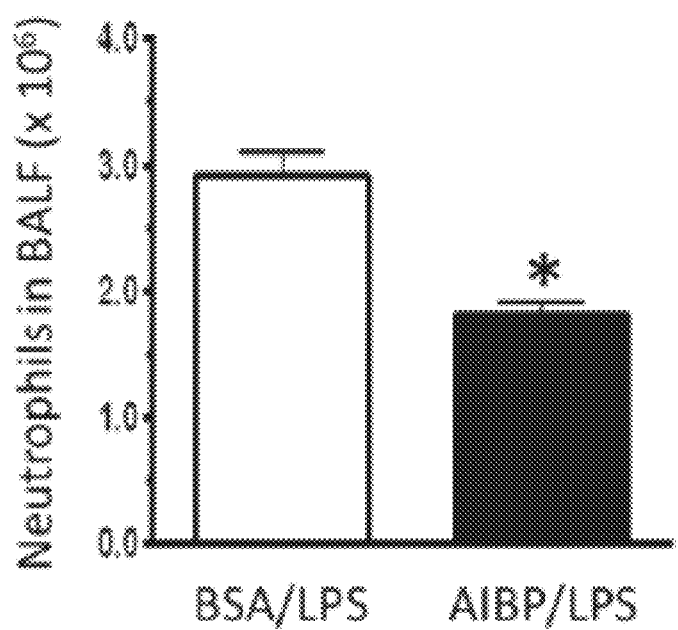

FIG. 43 graphically illustrates data showing that AIBP reduces lung inflammation in a mouse model of acute respiratory distress syndrome: all components were administered via nebulizer; neutrophils were counted in bronchoalveolar lavage fluid (BALF) 24 hors post LPS administration.

Like reference symbols in the various drawings indicate like elements.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

In alternative embodiments, the invention provides pharmaceutical compounds and formulations comprising nucleic acids and polypeptides for regulating or manipulating (including enhancing expression, upregulating or inhibiting) the expression of ApoA-I Binding Protein (APOA1BP, AIBP, or AI-BP), and methods for making and using them.

Cholesterol is essential for cellular function and its levels are tightly regulated by several mechanisms, including cholesterol efflux to HDL and apoA-I. We found that proper removal of cholesterol from endothelial cells (EC) is required for normal embryonic angiogenesis and that apoA-I binding protein (AIBP) plays a critical role in this process. AIBP knockdown resulted in dysregulated sprouting angiogenesis, while ectopic AIBP expression inhibited angiogenesis during zebrafish development. A non-cell autonomous character of the AIBP effect suggested its role similar to that of a repellent molecule guiding angiogenesis. Importantly, dysregulated angiogenesis was phenocopied in embryos deficient in cholesterol transporters ABCA1 and ABCG1. Cholesterol levels were increased in AIBP- and ABCA1/G1-deficient embryos. Our findings demonstrate that AIBP accelerates cholesterol efflux from EC and that this mechanism is involved in regulation of angiogenesis.

The invention also demonstrates that ApoA-I binding protein (AIBP) accelerates ABCG1-dependent cholesterol efflux from endothelial cells (EC) and that AIBP expression is critical for proper angiogenesis. Thus, in alternative embodiments, the invention provides compositions and methods using ApoA-I binding protein (AIBP) to accelerate ABCG1-dependent cholesterol efflux from endothelial cells (EC) and to control AIBP expression and regulate or modify angiogenesis.

In the presence of HDL, AIBP reduces lipid rafts and inhibits vascular endothelial growth factor (VEGF)-induced EC tube formation in vitro and aortic ring neovascularization ex vivo. Thus, in alternative embodiments, the invention provides compositions and methods using ApoA-I binding protein (AIBP) to reduce lipid rafts and inhibits vascular endothelial growth factor (VEGF)-induced EC tube formation in vivo and in vitro.

The invention demonstrates that AIBP functions as a non-cell autonomous regulator of angiogenesis in embryonic zebrafish. AIBP knockdown results in dysregulated sprouting/branching angiogenesis, while ectopic Aibp expression inhibits angiogenesis. Dysregulated angiogenesis is phenocopied in Abca1/Abcg1-deficient embryos, and cholesterol levels are increased in Aibp-deficient and Abca1/Abcg1-deficient embryos. Our findings demonstrate that secreted AIBP positively regulates cholesterol efflux from EC and that effective cholesterol efflux is critical for proper angiogenesis.

Products of Manufacture, Kits

The invention also provides products of manufacture, kits and pharmaceuticals for practicing the methods of this invention. In alternative embodiments, the invention provides products of manufacture, kits and/or pharmaceuticals comprising all the components needed to practice a method of the invention.

Antisense Inhibitory Nucleic Acid Molecules

In alternative embodiments, the invention provides compositions and methods for reducing the amount of or reducing the activity of APOA1BP by administering APOA1BP-inhibiting nucleic acids, e.g., an antisense morpholino oligonucleotide (MO), an miRNA, an siRNA and the like. In alternative embodiments, APOA1BP-inhibiting pharmaceutical compositions and formulations of the invention are administered to an individual in need thereof in an amount sufficient to stimulate tissue revascularization, e.g., supporting or stimulating revascularization of heart tissue, e.g., after a cardiac ischemia.

In alternative embodiments, compositions and methods of the invention comprise use of an inhibitory nucleic acid molecule or an antisense oligonucleotide inhibitory to expression of an APOA1BP gene transcript. In alternative embodiments, compositions and methods of the invention comprise use of an inhibitory nucleic acid molecule or antisense oligonucleotide inhibitory to expression of the APOA1BP gene, e.g., an APOA1BP1 or APOA1BP2 gene transcript comprises: an RNAi inhibitory nucleic acid molecule, a double-stranded RNA (dsRNA) molecule, a small interfering RNA (siRNA), a microRNA (miRNA) and/or a short hairpin RNA (shRNA), or a ribozyme.

Naturally occurring or synthetic nucleic acids can be used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) Toxicol. Appl. Pharmacol. 144:189-197; Antisense Therapeutics, ed. Agrawal (Humana Press, Totowa, N.J., 1996). Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene(methylimino), 3'-N-carbamate, and morpholino carbamate nucleic acids.

RNA Interference (RNAi)

In one aspect, the invention provides RNAi inhibitory nucleic acid molecules capable of decreasing or inhibiting expression of one or a set of APOA1BP transcripts or proteins, e.g., the transcript (mRNA, message) or isoform or isoforms thereof. In one aspect, the RNAi molecule comprises a double-stranded RNA (dsRNA) molecule. The RNAi molecule can comprise a double-stranded RNA (dsRNA) molecule, e.g., siRNA, miRNA (microRNA) and/or short hairpin RNA (shRNA) molecules.

In alternative aspects, the RNAi is about 11, 12, 13, 14, 15, 16, 17, 18, 19, 20, 21, 22, 23, 24, 25 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi, e.g., siRNA for inhibiting transcription and/or miRNA to inhibit translation, is the breaking of a double-stranded RNA (dsRNA) matching a specific gene sequence into short pieces called short interfering RNA, which trigger the degradation of mRNA that matches its sequence.

In one aspect, intracellular introduction of the RNAi (e.g., miRNA or siRNA) is by internalization of a target cell specific ligand bonded to an RNA binding protein comprising an RNAi (e.g., microRNA) is adsorbed. The ligand can be specific to a unique target cell surface antigen. The ligand can be spontaneously internalized after binding to the cell surface antigen. If the unique cell surface antigen is not naturally internalized after binding to its ligand, internalization can be promoted by the incorporation of an arginine-rich peptide, or other membrane permeable peptide, into the structure of the ligand or RNA binding protein or attachment of such a peptide to the ligand or RNA binding protein. See, e.g., U.S. Patent App. Pub. Nos. 20060030003; 20060025361; 20060019286; 20060019258. In one aspect, the invention provides lipid-based formulations for delivering, e.g., introducing nucleic acids of the invention as nucleic acid-lipid particles comprising an RNAi molecule to a cell, see e.g., U.S. Patent App. Pub. No. 20060008910.

Methods for making and using RNAi molecules, e.g., siRNA and/or miRNA, for selectively degrade RNA are well known in the art, see, e.g., U.S. Pat. Nos. 6,506,559; 6,511,824; 6,515,109; 6,489,127.

Methods for making expression constructs, e.g., vectors or plasmids, from which an inhibitory polynucleotide (e.g., a duplex siRNA of the invention) is transcribed are well known and routine. A regulatory region (e.g., promoter, enhancer, silencer, splice donor, acceptor, etc.) can be used to transcribe an RNA strand or RNA strands of an inhibitory polynucleotide from an expression construct. When making a duplex siRNA inhibitory molecule, the sense and antisense strands of the targeted portion of the targeted IRES can be transcribed as two separate RNA strands that will anneal together, or as a single RNA strand that will form a hairpin loop and anneal with itself. For example, a construct targeting a portion of a gene, e.g., a APOA1BP coding sequence or transcriptional activation sequence, is inserted between two promoters (e.g., mammalian, viral, human, tissue specific, constitutive or other type of promoter) such that transcription occurs bidirectionally and will result in complementary RNA strands that may subsequently anneal to form an inhibitory siRNA of the invention.

Alternatively, a targeted portion of a gene, coding sequence, promoter or transcript can be designed as a first and second antisense binding region together on a single expression vector; for example, comprising a first coding region of a targeted gene in sense orientation relative to its controlling promoter, and wherein the second coding region of the gene is in antisense orientation relative to its controlling promoter. If transcription of the sense and antisense coding regions of the targeted portion of the targeted gene occurs from two separate promoters, the result may be two separate RNA strands that may subsequently anneal to form a gene-inhibitory siRNA used to practice this invention.

In another aspect, transcription of the sense and antisense targeted portion of the targeted gene is controlled by a single promoter, and the resulting transcript will be a single hairpin RNA strand that is self-complementary, i.e., forms a duplex by folding back on itself to create a gene-inhibitory siRNA molecule. In this configuration, a spacer, e.g., of nucleotides, between the sense and antisense coding regions of the targeted portion of the targeted gene can improve the ability of the single strand RNA to form a hairpin loop, wherein the hairpin loop comprises the spacer. In one embodiment, the spacer comprises a length of nucleotides of between about 5 to 50 nucleotides. In one aspect, the sense and antisense coding regions of the siRNA can each be on a separate expression vector and under the control of its own promoter.

Inhibitory Ribozymes

In alternative embodiment, compositions and methods of the invention comprise use of ribozymes capable of binding and inhibiting, e.g., decreasing or inhibiting, expression of one or a set of APOA1BP transcripts or proteins, or isoform or isoforms thereof.

These ribozymes can inhibit a gene's activity by, e.g., targeting a genomic DNA or an mRNA (a message, a transcript). Strategies for designing ribozymes and selecting a gene-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it can be released from that RNA to bind and cleave new targets repeatedly.

Formulations and Pharmaceutical Compositions

In alternative embodiments, the invention provides pharmaceutical formulations or compositions comprising nucleic acids and polypeptides for regulating (including upregulating or inhibiting) the expression of ApoA-I Binding Protein (APOA1BP, AIBP, or AI-BP). In alternative embodiments, the invention provides pharmaceutical formulations or compositions for use in in vivo, in vitro or ex vivo methods to treat, prevent, reverse and/or ameliorate neovascularization of a growth, cancer or tumor whose growth or survival depends on neovascularization. In alternative embodiments, pharmaceutical compositions and formulations of the invention that comprise APOA1BP nucleic acids and polypeptides or result in an increase in expression or activity of APOA1BP nucleic acids and polypeptides are administered to an individual in need thereof in an amount sufficient to treat, prevent, reverse and/or ameliorate a dyslipidemia, e.g., to treat, prevent, reverse and/or ameliorate conditions responsive to increasing cholesterol efflux from cells, including cardiovascular disease and atherosclerosis. In alternative embodiments, pharmaceutical compositions and formulations of the invention that comprise APOA1BP nucleic acids and polypeptides or result in an increase in expression or activity of APOA1BP nucleic acids and polypeptides are administered to an individual in need thereof in an amount sufficient to stimulate tissue revascularization, e.g., supporting or stimulating revascularization of heart tissue, e.g., after a cardiac ischemia.

In alternative embodiments, the pharmaceutical compositions of the invention can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of *Remington's Pharmaceutical Sciences*, Maack Publishing Co., Easton Pa. ("Remington's"). For example, in alternative embodiments, these compositions of the invention are formulated in a buffer, in a saline solution, in a powder, an emulsion, in a vesicle, in a liposome, in a nanoparticle, in a nanolipoparticle and the like. In alternative embodiments, the compositions can be formulated in any way and can be applied in a variety of concentrations and forms depending on the desired in vivo, in vitro or ex vivo conditions, a desired in vivo, in vitro or ex vivo method of administration and the like. Details on techniques for in vivo, in vitro or ex vivo formulations and administrations are well described in the scientific and patent literature. Formulations and/or carriers used to practice this invention can be in forms such as tablets, pills, powders, capsules, liquids, gels, syrups, slurries, suspensions, etc., suitable for in vivo, in vitro or ex vivo applications.

In practicing this invention, the compounds (e.g., formulations) of the invention can comprise a solution of compositions (which include peptidomimetics, racemic mixtures or racemates, isomers, stereoisomers, derivatives and/or analogs of compounds of the invention) disposed in or dissolved in a pharmaceutically acceptable carrier, e.g., acceptable vehicles and solvents that can be employed include water and Ringer's solution, an isotonic sodium chloride. In addition, sterile fixed oils can be employed as a solvent or suspending medium. For this purpose any fixed oil can be employed including synthetic mono- or diglycerides, or fatty acids such as oleic acid. In one embodiment, solutions and formulations used to practice the invention are sterile and can be manufactured to be generally free of undesirable matter. In one embodiment, these solutions and formulations are sterilized by conventional, well known sterilization techniques.

The solutions and formulations used to practice the invention can comprise auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and can be selected primarily based on fluid volumes, viscosities and the like, in accordance with the particular mode of in vivo, in vitro or ex vivo administration selected and the desired results.

The compositions and formulations of the invention can be delivered by the use of liposomes. By using liposomes, particularly where the liposome surface carries ligands specific for target cells (e.g., an injured or diseased neuronal cell or CNS tissue), or are otherwise preferentially directed to a specific tissue or organ type, one can focus the delivery of the active agent into a target cells in an in vivo, in vitro or ex vivo application.

Nanoparticles, Nanolipoparticles and Liposomes

The invention also provides nanoparticles, nanolipoparticles, vesicles and liposomal membranes comprising compounds used to practice the methods of this invention, e.g., to deliver compositions of the invention (which include APOA1BP nucleic acids and polypeptides of the invention) to mammalian cells in vivo, in vitro or ex vivo. In alternative embodiments, these compositions are designed to target specific molecules, including biologic molecules, such as polypeptides, including cell surface polypeptides, e.g., for targeting a desired cell type, e.g., a myocyte or heart cell, and endothelial cell, and the like.

The invention provides multilayered liposomes comprising compounds used to practice this invention, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition used to practice this invention.

Liposomes can be made using any method, e.g., as described in Park, et al., U.S. Pat. Pub. No. 20070042031, including method of producing a liposome by encapsulating an active agent (e.g., APOA1BP nucleic acids and polypeptides), the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions used to practice this invention comprise a substituted ammonium and/or polyanions, e.g., for targeting delivery of a compound (e.g., a APOA1BP nucleic acid and polypeptide of the invention) used to practice this invention to a desired cell type (e.g., an endothelial cell, a cancer cell, or any tissue in need thereof), as described e.g., in U.S. Pat. Pub. No. 20070110798.

The invention also provides nanoparticles comprising compounds (e.g., APOA1BP nucleic acids and polypeptides of the invention) used to practice this invention in the form of active agent-containing nanoparticles (e.g., a secondary nanoparticle), as described, e.g., in U.S. Pat. Pub. No. 20070077286. In one embodiment, the invention provides nanoparticles comprising a fat-soluble active agent of this invention or a fat-solubilized water-soluble active agent to act with a bivalent or trivalent metal salt.

In one embodiment, solid lipid suspensions can be used to formulate and to deliver compositions used to practice this invention to mammalian cells in vivo, in vitro or ex vivo, as described, e.g., in U.S. Pat. Pub. No. 20050136121.

Delivery Vehicles

In alternative embodiments, any delivery vehicle can be used to practice the methods or used to practice this invention, e.g., to deliver compositions of the invention (e.g., APOA1BP nucleic acids and polypeptides) to mammalian cells in vivo, in vitro or ex vivo. For example, delivery vehicles comprising polycations, cationic polymers and/or cationic peptides, such as polyethyleneimine derivatives, can be used e.g. as described, e.g., in U.S. Pat. Pub. No. 20060083737.

In one embodiment, a dried polypeptide-surfactant complex is used to formulate a composition used to practice this invention, e.g. as described, e.g., in U.S. Pat. Pub. No. 20040151766.

In one embodiment, a composition used to practice this invention can be applied to cells using vehicles with cell membrane-permeant peptide conjugates, e.g., as described in U.S. Pat. Nos. 7,306,783; 6,589,503. In one aspect, the composition to be delivered is conjugated to a cell membrane-permeant peptide. In one embodiment, the composition to be delivered and/or the delivery vehicle are conjugated to a transport-mediating peptide, e.g., as described in U.S. Pat. No. 5,846,743, describing transport-mediating peptides that are highly basic and bind to poly-phosphoinositides.

In one embodiment, electro-permeabilization is used as a primary or adjunctive means to deliver the composition to a cell, e.g., using any electroporation system as described e.g. in U.S. Pat. Nos. 7,109,034; 6,261,815; 5,874,268.

Dosaging

The pharmaceutical compositions and formulations of the invention can be administered for prophylactic and/or therapeutic treatments. In therapeutic applications, compositions are administered to a subject already suffering from a disease, condition, infection or defect in an amount sufficient to cure, alleviate or partially arrest the clinical manifestations of the disease, condition, infection or disease and its complications (a "therapeutically effective amount"). For example, in alternative embodiments, APOA1BP nucleic acid- or polypeptide-comprising pharmaceutical compositions and formulations of the invention are administered to an individual in need thereof in an amount sufficient to treat, prevent, reverse and/or ameliorate a dyslipidemia, unwanted angiogenesis, e.g., cancer or tumor angiogenesis, or to stimulate wanted angiogenesis, e.g., to stimulate revascularization of heart tissue, e.g., after a cardiac ischemia.

The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. For example, alternative exemplary pharmaceutical formulations for oral administration of compositions used to practice the invention are in a daily amount of between about 0.1 to 0.5 to about 20, 50, 100 or 1000 or more ug per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The methods of the invention can further comprise co-administration with other drugs or pharmaceuticals, e.g., compositions for treating any neurological or neuromuscular disease, condition, infection or injury, including related inflammatory and autoimmune diseases and conditions, and the like. For example, the methods and/or compositions and formulations of the invention can be co-formulated with and/or co-administered with, fluids, antibiotics, cytokines, immunoregulatory agents, anti-inflammatory agents, pain alleviating compounds, complement activating agents, such as peptides or proteins comprising collagen-like domains or fibrinogen-like domains (e.g., a ficolin), carbohydrate-binding domains, and the like and combinations thereof.

Bioisosteres of Compounds of the Invention

In alternative embodiment, the invention also provides and uses bioisosteres of compounds of the invention, e.g., polypeptides having a APOA1BP activity. Bioisosteres of the invention are compounds of the invention, e.g., APOA1BP nucleic acids and polypeptides, comprising one or more substituent and/or group replacements with a substituent and/or group having substantially similar physical or chemical properties which produce substantially similar biological properties to compounds of the invention. In one embodiment, the purpose of exchanging one bioisostere for another is to enhance the desired biological or physical properties of a compound without making significant changes in chemical structures.

For example, in one embodiment, one or more hydrogen atom(s) is replaced with one or more fluorine atom(s), e.g., at a site of metabolic oxidation; this may prevent metabolism (catabolism) from taking place. Because the fluorine atom is similar in size to the hydrogen atom the overall topology of the molecule is not significantly affected, leaving the desired biological activity unaffected. However, with a blocked pathway for metabolism, the molecule may have a longer half-life or be less toxic, and the like.

Kits and Instructions

The invention provides kits comprising compositions and/or instructions for practicing methods of the invention. As such, kits, cells, vectors and the like can also be provided. In alternative embodiments, the invention provides kits comprising: a composition used to practice a method of any of the invention, or a composition, a pharmaceutical composition or a formulation of the invention, and optionally comprising instructions for use thereof.

The invention will be further described with reference to the examples described herein; however, it is to be understood that the invention is not limited to such examples.

EXAMPLES

Example 1: Exemplary Compounds and Methods of the Invention Regulate Cholesterol Transport and Angiogenesis: ApoA-I Binding Protein-Mediated Cholesterol Efflux Controls Angiogenesis This example describes and demonstrates exemplary activities, and the efficacy, of compounds and methods of the invention. While the invention is not limited by any particular mechanism of action, in one embodiment, methods of the invention use APOA1BP to accelerate cholesterol efflux from cells, e.g., endothelial cells (EC), and that this mechanism is involved in regulation of angiogenesis, and secreted AIBP functions as a local regulator of reverse cholesterol transport and as such, controls endothelial cell (EC) proliferation and angiogenesis.

AIBP is differentially expressed in many angiogenic tumors, making to a top 1% of differentially regulated genes in invasive breast carcinoma (11, 12). Thus, in this work, we tested the hypothesis that secreted AIBP functions as a local regulator of reverse cholesterol transport and as such, controls endothelial cell (EC) proliferation and angiogenesis.

AIBP is evolutionary conserved from Drosophila to zebrafish to mouse and human (Fig. S1A). Zebrafish AIBP (gene name apoa1bp) has two isoforms, AIBP1 and AIBP2 (Fig. S1B). To identify the role that AIBP plays in embryonic angiogenesis, we injected antisense morpholino oligonucleotides (MO) targeting AIBP1 and AIBP2 translation sites into one-cell stage embryos of Tg(fli1-egfp)$^{y1}$ zebrafish, which express EGFP in EC (13). No obvious abnormalities were observed in AIBP1 morphants (data not shown), whereas ectopic branching of segmental arteries (SeA) and pathologic sprouting of subintestinal veins (SIV) were found in AIBP2 morphants (FIG. 1A-B).

These results were confirmed with a morpholino oligonucleotide (MO) targeting AIBP2 gene splicing (Fig. S2). The AIBP2 knockdown in morphant embryos was validated in western blot (FIG. 2C). The unregulated sprouting of SeAs in AIBP2 morphants was partially rescued by ectopic expression of AIBP2 delivered by an mRNA lacking the binding site targeted by the MO (FIG. 1B). The results of these loss of function and rescue experiments demonstrated a role for AIBP2 in angiogenesis.

To test whether AIBP2 deficiency affected EC proliferation, we injected control and AIBP2 MO into Tg(fli1:negfp)$^{y7}$ one-cell stage embryos. Numbers of fluorescent EC nuclei in SeAs and DLAV of AIBP2 morphants were increased (FIG. 1C-D), suggesting that AIBP2 regulates EC proliferation.

Next, the tissue distribution of AIBP2 in embryos at different developmental stages was examined by whole embryo in situ hybridization (WISH) (FIG. 1E). AIBP2 expression was detected as early as 20 min post fertilization and was clearly evident in somites at 12 hours post fertilization (hpf). Notably, the AIBP2 signal at 24 hpf showed an interval somite distribution in the medial and posterior trunk of the embryo, the distribution resembling that of type 3 semaphorins, non-cell autonomous repellent cues that guide the patterning of developing SeAs via PlexinD1 receptors (14-16).

To determine the cell autonomy of AIBP2 effect on angiogenesis, we performed cell transplantation experiments. Fluorescent EC from wild type Tg(fli1:egfp)$^{y1}$ donors found in nonfluorescent AIBP2 morphants displayed excessive sprouting, branching and filopodial projections (FIG. 1F-G).

In a reverse experiment, transplantation of cells from Tg(fli1:egfp)$^{y1}$ AIBP2 morphants into wild type embryos with unaffected AIBP2 expression did not disturb normal morphology of fluorescent EC. These results demonstrate the role of AIBP2 as a repellent molecule whose function depends on the milieu surrounding EC but not on AIBP2 expression in the EC themselves.

Notch, VEGF and other signaling pathways are finely tuned during the process of angiogenesis (17-21). The impact of the loss of AIBP2 on molecular pathways involved in angiogenesis was examined in control and AIBP2 morphants in a microarray experiment. Genes indicative of enhanced cell proliferation and genes involved in angiogenesis, such as Tie2, VEGFR2, VEGFR3 and fli1, were upregulated in AIBP2 morphants (Fig. S3). The increased expression of genes involved in angiogenesis was confirmed by both qRT-PCR and WISH (FIGS. 2A and 2B). Further, in agreement with the excessive SeA branching/sprouting phenotype (FIGS. 1A and D), Dll4 was markedly down-regulated in AIBP2 morphants (FIG. 2B). Taken together, these data demonstrate that the molecular pathways that orchestrate angiogenesis are dramatically affected by the AIBP2 knockdown.

The interplay between activation and inhibition of ERK and Akt directs angiogenesis, and upregulated Akt activity rescues the angiogenesis defects caused by VEGFR inhibitors (22-24). Lysates of AIBP2 morphant embryos displayed robust activation of Akt and mild inhibition of ERK (FIG. 2C), supporting the AIBP2 role in angiogenesis. The AIBP2 knockdown in morphants was confirmed with a guinea pig antibody generated against recombinant zebrafish AIBP2 (FIGS. 2C and S4).

Because binding of human AIBP to apoA-I (8) suggests a role for AIBP in cholesterol metabolism, we tested whether AIBP2 knockdown affects cholesterol levels in embryonic zebrafish. The 24 hpf embryos were stained with filipin, a fluorescent dye specifically binding to free (unesterified) cholesterol (25). The filipin fluorescence was increased in AIBP2 morphant embryos (excluding the yolk) compared to controls (FIGS. 2D and E). These results were confirmed with direct gas chromatography measurements of free cholesterol in lipid extracts from pooled embryos from which the yolk was removed (FIG. 3F). Increased levels of free cholesterol measured by two independent techniques suggest that AIBP2 is required for normal cholesterol metabolism.

Next, we sought to connect a putative role of AIBP in cholesterol metabolism with its role in angiogenesis discovered in this study. First, we tested if zebrafish AIBP2 binds with HDL and apoA-I. AIBP2 was added to human plasma and lipoprotein fractions were separated by density ultracentrifugation (Fig. S5). AIBP2 was detected in the HDL fraction but not in LDL or VLDL fractions (FIG. 3A). A pull down assay was used to confirm binding of human AIBP and zebrafish AIBP2 with human apoA-I (FIG. 3B). ApoA-I and HDL remove cholesterol from the cells.

We asked whether AIBP binding to HDL and apoA-I would have any effect on cholesterol efflux from EC. Within 1 hour, human AIBP and zebrafish AIBP2 significantly increased cholesterol efflux to HDL from human umbilical vein endothelial cells (HUVEC), while zebrafish AIBP1 had a smaller effect (FIG. 3C). Accelerated cholesterol efflux in the presence of human AIBP was observed within first 4 hours (FIG. 3D), and the enhancement of cholesterol removal in the presence of AIBP was diminished at later time points. These results demonstrate that AIBP promotes cholesterol efflux from EC.

Because cholesterol levels in the plasma membrane microdomains may drastically affect cell signaling (26, 27), we tested whether enhanced cholesterol efflux in cells pre-incubated with hAIBP/HDL would affect subsequent HUVEC responses to VEGF. The VEGF-stimulated activation of Akt was decreased in HUVEC preincubated with hAIBP/HDL, but not with AIBP or HDL alone (Fig. S6). Likewise, hAIBP/HDL completely abrogated VEGF-induced HUVEC angiogenesis in an in vitro assay (FIG. 3E). These HUVEC results agree with the increased Akt phosphorylation (FIG. 2C) and increased EC branching (FIG. 1A) observed in AIBP2 zebrafish morphants.

In HUVEC, ATP-binding cassette sub-family G member 1 (ABCG1) is a major transporter responsible for cholesterol efflux (28). Remarkably, knockdown of ABCG1 in HUVEC resulted in complete loss of the AIBP effect (FIG. 3F), suggesting that AIBP indeed accelerates cholesterol efflux from HUVEC via the HDL/ABCG1 pathway.

To further test the hypothesis that effective cholesterol efflux is required for normal angiogenesis, we knocked down zebrafish ABCA1 and ABCG1. These cellular cholesterol transporters are essential for cholesterol efflux in mammals (1-3). Expression of ABCA1 and ABCG1 has been found in zebrafish and, as in mammals, it is induced by liver X receptor agonists (29, 30). We found that the loss of ABCA1 and ABCG1 in zebrafish closely reproduced the vascular developmental defects of AIBP2 morphants, in both SeA and, markedly, in SIV vascular beds (FIG. 4A-F). The latter finding was confirmed with Tg(fli1:negfp)y7 AIBP2 and ABCA1/G1 morphants in which we observed increased numbers of EC nuclei in SIV sprouts (Fig. S7). As expected, ABCA1/G1 morphants had higher levels of free cholesterol than control embryos (Fig. S8). Similarly to AIBP2 morphants, phosphorylation of Akt was increased in ABCA1/G1 morphants as well (FIG. 2C).

In agreement with the AIBP2 knockdown results, overexpression of AIBP2-mCherry in somites driven by the myog promoter resulted in inhibition of SeA growth and incomplete SeA angiogenesis (FIG. 4G-H). Remarkably, the inhibition of SeA formation induced by ectopic AIBP2-mCherry expression was rescued by knocking down ABCA1/G1. These results provide an additional evidence that AIBP2 is a repellent guiding blood vessel growth and also suggest that ABCA1/G1 are required for AIBP2 function in reverse cholesterol transport. The latter is supported by the results of HUVEC experiments (FIG. 3F).

Our findings demonstrating the role of ABCA1/G1 in regulation of EC branching/sprouting in zebrafish embryo agree with the recent reports suggesting the role of reverse cholesterol transport in proliferation of other cell types in adult organisms (4-6, 31, 32). In mice, deficiency in ABCA1 and/or ABCG1 results in elevated cellular cholesterol levels and enhanced proliferation of monocytes, smooth muscle cells and T cells as well as dysregulated cell migration (4-6, 31, 32). Importantly, crossing ABCA1/G1 double knockout mice with ApoA-I transgenic mice rescued the myeloproliferative disorder of monocytes in ABCA1/G1-deficient mice, indicating that HDL inhibits abnormal monocyte proliferation by reducing cholesterol content in the cells (4).

High levels of cholesterol in apoE null mice have been reported to facilitate endothelial progenitor cell-mediated repair after incurred carotid artery injury (31). Cholesterol has been shown to play a critical role in lipid rafts formation (33). Increased signaling of IL3fÀ receptor in myeloid cells from ABCA1/G1 double knockout mice and enhanced TLR4 signaling in macrophages from ABCA1 knockout mice are likely the result of cholesterol-induced enrichment in lipid rafts leading to receptor dimerization (4, 34). In agreement, cholesterol depletion inhibits T cell activation (33).

Our results demonstrate, for the first time, the importance of cholesterol efflux in regulation of embryonic angiogenesis. In addition, a novel finding of this study is that AIBP plays a previously unrecognized role in accelerated cholesterol efflux from EC and in angiogenesis. Increased cholesterol efflux, promoted by AIBP, likely disrupts organization of plasma membrane microdomains and thereby compromises function of membrane receptors, such as VEGFR and Tie2. This may explain the connection between intracellular levels of free cholesterol and EC branching/sprouting. As illustrated in FIG. 4I, our findings imply that in embryonic zebrafish angiogenesis, AIBP2 expression in somites likely recruits HDL to sites around growing SeA.

Increased cholesterol efflux at these sites, together with other inhibitory mechanisms (14, 15), arrests aberrant intrasomitic growth of EC, thereby guiding angiogenesis along the path between somites. The invention provides compositions and methods to manipulate AIBP function in angiogenesis and in a variety of pathologic and regenerative processes, from cancer to cardiovascular disease.

REFERENCES EXAMPLE 1

1. J. Klucken et al., ABCG1 (ABC8), the human homolog of the *Drosophila* white gene, is a regulator of macrophage cholesterol and phospholipid transport. Proc Natl Acad Sci USA 97, 817 (Jan. 18, 2000).
2. E. Orso et al., Transport of lipids from Golgi to plasma membrane is defective in tangier disease patients and Abc1-deficient mice. Nat Genet 24, 192 (February, 2000).
3. S. Rust et al., Tangier disease is caused by mutations in the gene encoding ATP-binding cassette transporter 1. Nat Genet 22, 352 (August, 1999).
4. L. Yvan-Charvet et al., ATP-Binding Cassette Transporters and HDL Suppress Hematopoietic Stem Cell Proliferation. Science 328, 1689 (2010).
5. A. J. Armstrong, A. K. Gebre, J. S. Parks, C. C. Hedrick, ATP-Binding Cassette Transporter G1 Negatively Regulates Thymocyte and Peripheral Lymphocyte Proliferation. J. of Immunology 184, 173 (2009).
6. S. J. Bensinger et al., LXR Signaling Couples Sterol Metabolism to Proliferation in the Acquired Immune Response. Cell 134, 97 (2008).
7. N. Terasaka et al., ABCG1 and HDL protect against endothelial dysfunction in mice fed a high-cholesterol diet. Journal of Clinical Investigation 118, 3701 (2008).
8. M. Ritter et al., Cloning and characterization of a novel apolipoprotein A-I binding protein, AI-BP, secreted by cells of the kidney proximal tubules in response to HDL or ApoA-I. Genomics 79, 693 (May, 2002).
9. J. S. Bodnar et al., Positional cloning of the combined hyperlipidemia gene Hyplip1. Nat. Genet 30, 110 (January, 2002).
10. K. N. Jha et al., Biochemical and structural characterization of apolipoprotein A-I binding protein, a novel phosphoprotein with a potential role in sperm capacitation. Endocrinology 149, 2108 (May, 2008).
11. B. Skawran et al., Gene expression profiling in hepatocellular carcinoma: upregulation of genes in amplified chromosome regions. Mod Pathol 21, 505 (May, 2008).
12. Data mining for the term ☐gAPOA1BP☐h in www.oncomine.org and www.ebi.ac.uk.
13. N. D. Lawson, B. M. Weinstein, In vivo imaging of embryonic vascular development using transgenic zebrafish. Dev Biol 248, 307 (Aug. 15, 2002).
14. J. Torres-Vazquez et al., Semaphorin-Plexin Signaling Guides Patterning of the Developing Vasculature. Developmental Cell 7, 117 (2004).
15. C. Guet et al., Semaphorin 3E and Plexin-D1 Control Vascular Pattern 30 Independently of Neuropilins. Science 307, 265 (2005).
16. T. Zygmunt et al., Semaphorin-PlexinD1 Signaling Limits Angiogenic Potential via the VEGF Decoy Receptor sFlt1. Dev Cell 21, 301 (Aug. 16, 2011).
17. A. F. Siekmann, L. Covassin, N. D. Lawson, Modulation of VEGF signalling output by the Notch pathway. Bioessays 30, 303 (April, 2008).
18. R. H. Adams, K. Alitalo, Molecular regulation of angiogenesis and lymphangiogenesis. Nat Rev Mol Cell Biol 8, 464 (June, 2007).
19. Y. Wang et al., Ephrin-B2 controls VEGF-induced angiogenesis and lymphangiogenesis. Nature 465, 483 (2010).
20. B. M. Hogan et al., Vegfc/Flt4 signalling is suppressed by Dll4 in developing zebrafish intersegmental arteries. Development 136, 4001 (December, 2009).
21. S. P. Herbert, D. Y. Stainier, Molecular control of endothelial cell behaviour during blood vessel morphogenesis. Nat Rev Mol Cell Biol 12, 551 (2011).
22. C. C. Hong, Q. P. Peterson, J.-Y. Hong, R. T. Peterson, Artery/Vein Specification Is Governed by Opposing Phosphatidylinositol-3 Kinase and MAP Kinase/ERK Signaling. Current Biology 16, 1366 (2006).
23. B. Ren et al., ERK1/2-Akt1 crosstalk regulates arteriogenesis in mice and zebrafish. Journal of Clinical Investigation 120, 1217 (2010).
24. J. Chan, P. E. Bayliss, J. M. Wood, T. M. Roberts, Dissection of angiogenic signaling in zebrafish using a chemical genetic approach. Cancer Cell 1, 257 (April, 2002).
25. H. S. Kruth, M. Vaughan, Quantification of low density lipoprotein binding and cholesterol accumulation by single human fibroblasts using fluorescence microscopy. J Lipid Res 21, 123 (January, 1980).
26. K. Simons, E. Ikonen, Functional rafts in cell membranes. Nature 387, 569 (Jun. 5, 1997).
27. Y. D. Paila, A. Chattopadhyay, Membrane cholesterol in the function and organization of G-protein coupled receptors. Subcell Biochem 51, 439 (2010).
28. B. J. O'Connell, Cellular Physiology of Cholesterol Efflux in Vascular Endothelial Cells. Circulation 110, 2881 (2004).
29. M. Futter et al., Wild-type but not mutant huntingtin modulates the transcriptional activity of liver X receptors. J Med Genet 46, 438 (July, 2009).
30. B. Thisse, Pfumio, S., Furthauer, M., Loppin B., Heyer, V., Degrave, A., Woehl, R., Lux, A., Steffan, T., Charbonnier, X. Q. and Thisse, C., Expression of the zebrafish genome during embryogenesis (NIH R01 RR15402). ZFIN Direct Data Submission (http://zfin.org), (2001).
31. M. Ii et al., Notch Signaling Regulates Endothelial Progenitor Cell Activity During Recovery From Arterial Injury in Hypercholesterolemic Mice. Circulation 121, 1104(2010).
32. F. Blaschke et al., Liver X receptor agonists suppress vascular smooth muscle cell proliferation and inhibit neointima formation in balloon-injured rat carotid arteries. Circ Res 95, e110 (Dec. 10, 2004).
33. K. Simons, M. J. Gerl, Revitalizing membrane rafts: new tools and insights. Nature Reviews Molecular Cell Biology 11, 688 (2010).
34. X. Zhu et al., Macrophage ABCA1 reduces MyD88-dependent Toll-like receptor trafficking to lipid rafts by reduction of lipid raft cholesterol. J Lipid Res 51, 3196 (November, 2010).
35. B. L. Roman et al., Disruption of acvrl1 increases endothelial cell number in zebrafish cranial vessels. Development 129, 3009 (June, 2002).

36. M. Westerfield, The Zebrafish Book. (University of Oregon Press, Eugene, Oreg., ed. 5th, 2007).
37. K. Stoletov et al., Vascular lipid accumulation, lipoprotein oxidation, and macrophage lipid uptake in hypercholesterolemic zebrafish. Circ Res 104, 952 (Apr. 24, 2009).
38. C. Thisse, B. Thisse, High-resolution in situ hybridization to whole-mount zebrafish embryos. Nat Protoc 3, 59 (2008).
39. A. F. Siekmann, N. D. Lawson, Notch signaling limits angiogenic cell behaviour in developing zebrafish arteries. Nature 445, 781 (2007).
40. N. D. Lawson et al., Notch signaling is required for arterial-venous differentiation during embryonic vascular development. Development 128, 3675 (October, 2001).
41. A. M. Catanzariti, T. A. Soboleva, D. A. Jans, P. G. Board, R. T. Baker, An efficient system for high-level expression and easy purification of authentic recombinant proteins. Protein Sci 13, 1331 (May, 2004).
42. L. Fang et al., Oxidized cholesteryl esters and phospholipids in zebrafish larvae fed a high cholesterol diet: macrophage binding and activation. J Biol Chem 285, 32343 (Oct. 15, 2010).
43. A. M. Whetzel et al., ABCG1 Deficiency in Mice Promotes Endothelial Activation and Monocyte-Endothelial Interactions. Arteriosclerosis, Thrombosis, and Vascular Biology 30, 809 (2010).
44. F. Gao et al., L-5F, an apolipoprotein A-I mimetic, inhibits tumor angiogenesis by suppressing VEGF/basic FGF signaling pathways. Integr Biol (Camb) 3, 479 (April, 2011).

Figure Legends

FIG. 1. Role of AIBP in zebrafish angiogenesis.
(A) One-cell stage fli1:EGFP zebrafish embryos were injected with 8 ng of either control MO or AIBP2 MO targeting ATG translation site. The images of SeA (images 1-2) and of SIV (3-4) were captured 3 days after MO injection. Arrows point to dysregulated sprouts. Scale, 50 m.
(B) Numbers of embryos with abnormal angiogenesis resulting from injection of control or AIBP2 MO. The abnormal angiogenesis was partially rescued by co-injection of 40 pg of AIBP2 RNA lacking the MO targeting site. 100-149 embryos per group. ***, $p<0.001$.
(C) One-cell stage fli1:nEGFP embryos were injected with 8 ng of either control MO or AIBP2 MO, and images were captured at 3 dpf. EC nuclei in each SeA were numerated. Scale, 50 µm.
(D) Quantification of EC nuclei in SeAs, n=8-9.
(E) Tissue distribution of AIBP2 mRNA in zebrafish embryo. Embryos at different developmental stages were fixed and WISH was performed with an antisense AIBP2 probe. Scale, 100 µm.
(F) Mosaic expression analysis of EC branching in WT and AIBP2 knockdown (KD) embryos. Four hours post fertilization; cells were isolated from donor embryos and were transplanted into recipient embryos (details of donor and recipient embryos are depicted above images). Three days after transplantation, the recipient embryos were analyzed. Red arrowheads indicate aberrant ectopic branches/sprouts in the AIBP2 KD recipients. Scale, 20 µm.
(G) Numbers of ectopic branches/filopodial projections per SeA. 8-16 embryos per group. ***, $p<0.001$.

FIG. 2. Upregulated markers of EC proliferation and angiogenesis in AIBP2 morphants.
(A) Expression of genes involved in angiogenesis. Total RNA was isolated from 24 hpf control and AIBP2 morphants and qRT-PCR was performed. The results are normalized to actin. The results are of 50 embryos per group, 3 to 4 replicates.*, $p<0.001$; , $p<0.01$; *, $p<0.05$.
(B) WISH analysis of genes involved in angiogenesis. Twenty four hpf control and AIBP2 morphants were fixed and hybridized with indicated probes. Scale, 100 µm.
(C) Akt and ERK1/2 phosphorylation. Twenty four hpf control and AIBP2 morphants were lysed and the lysates separated on SDS-PAGE and immunoblotted as indicated.
(D-F) Free cholesterol levels in AIBP2 morphants. (D) Twenty four hpf control and AIBP2 morphants were fixed and stained with filipin to detect free cholesterol in embryos. Note the yolks are artificially masked on the images. (E) Intensities of filipin fluorescence in mages shown in panel F (without yolks) were quantified in 12-15 embryos per group. *, $p<0.05$.
(F) One-cell stage embryos were injected with control or AIBP2 MO. At 24 hpf, the trunk area (without yolk and head) was dissected and total lipid was extracted. Free cholesterol levels were determined by GC. The cholesterol levels were normalized to the protein content and then to the values in control MO embryos. 50-70 embryos were pooled for each sample. The data are from 3-4 independent experiments.

FIG. 3. Effect of AIBP on cholesterol efflux.
(A) Five µg of purified His-tagged deubiquitinase (DUB, a non-relevant protein of the same molecular weight as AIBP), AIBP 1 or AIBP2 were incubated with 1 ml of human plasma overnight at 4° C. Ultracentrifugation was performed to separate lipoprotein fractions. Different fractions of lipoproteins were run on SDS-PAGE and immunoblotted with indicated antibodies.
(B) Three µg of purified human ApoA-I were mixed with 3 µg His-tagged AIBP2 or hAIBP and then immunoprecipitated with an á-His antibody. The blots were probed as indicated.
(C) Cholesterol efflux to HDL3. HUVEC were preloaded with 3H-cholesterol and then incubated for 1 hour with media, 50 µg/ml HDL3, 50 µg/ml HDL3+0.2 µg/ml His-AIBP, or 50 µg/ml HDL3+0.2 µg/ml His-DUB. The media and cell lysates were collected and 3H counts were measured. Efflux was measured as the 3H counts in the medium divided by the sum of 3H counts in the medium and the cell lysates. Mean±SD; n=3. **, $p<0.01$; *, $p<0.05$; #, $p=0.08$.
(D) Kinetics of cholesterol efflux from HUVEC to HDL3. Experimental conditions as in C.
(E) Effect of hAIBP and HDL3 on EC tube formation. HUVEC were preincubated with 50 µg/ml HDL3, 0.1 µg/ml His-hAIBP, or 50 µg/ml/ml HDL3+0.1 µg/ml His-hAIBP for 4 hours. Cells were then seeded on MATRIGEL™, in the presence or absence of 20 ng/ml VEGF, and imaged following a 12 hour incubation. Scale, 100 µm.
(F) Effect of ABCG1 knockdown on hAIBP mediated-cholesterol efflux. HUVEC were transfected with control or ABCG1 siRNA. The ABCG1 knockdown was confirmed in western blot. Control and ABCG1 deficient HUVEC were used in cholesterol efflux experiments as in panel C. n=6; *, $p<0.05$; **, $p<0.01$.

FIG. 4. Role of ABCA1/G1 in angiogenesis and in mediating effects of AIBP.

(A-F) Angiogenic defects in ABCA1/G1 morphants. One-cell stage embryos were injected with 8 ng of control MO, 8 ng AIBP2 MO, or 4 ng ABCA1 MO+4ng ABCG1 MO. Three days later, the morphants were analyzed by confocal microscopy. Images of SeA (A) and SIV (D) are shown. Scale, 50 μm. Graphs show number and length of SeA ectopic branches (B and C) and SIV ectopic sprouts (E and F) from 5-12 embryos.***, p<0.001.

(G-H) Rescue of the effect of AIBP2 overexpression in ABCA1/G1 morphants. (G) One cell stage embryos were injected with 2 nl of 100 ng/ml myog-AIBP2-mCherry plasmid, myog-AIBP2-mcherry plasmid together with ABCA1/G1 MO, or myog-mCherry. Two days later, the embryos were analyzed by confocal microscope. The arrow points to impaired migration of an SeA at the site of AIBP2-mCherry expression. Scale, 20 m. Abnormal SeA formation was quantified in 8-16 embryos per group (H). **, p<0.001.

(I) Diagram representing the hypothesis that somite expression of AIBP2 accelerates lateral cholesterol efflux from growing EC and thereby prevents its ectopic sprouting/branching.

Materials and Methods

Zebrafish: Wild type AB and transgenic Tg(fli1:egfp)y1 and (fli1:negfp)y7 zebrafish lines (13, 35) were kindly provided by Dr. David Traver. Zebrafish were maintained as previously described (36) and all experimental procedures were approved by the UCSD IACUC.

Confocal microscopy: Confocal imaging was carried out as previously described (37). Briefly, anaesthetized zebrafish embryos (treated at 24 hpf with 0.003% PTU) were housed in a sealed chamber (Invitrogen) in a small drop of 0.02% tricaine (Sigma) containing E3 medium. A Nikon C1-si™ confocal microscope was used in a one- or two-cannel mode to detect fluorescence of one or two fluorophores in the same embryo. In the green channel, excitation was 488 nm for EGFP, and in the red channel, 561 nm for mCherry. Z-stacks were acquired with a 1-3 μm step, and images were 3D rendered and analyzed using IMARIS® software (Bitplane). All 3D reconstructions were performed with the same threshold settings.

Quantitative analysis of cell sprouts in segmental arteries (SeA) and subintestinal veins (SIV): To determine changes in segmental artery cell sprouts in embryos injected with MOs targeting AIBP2 and ABCA1/G1, we counted abnormal projections in 4 to 6 pairs of segmental arteries in adjacent somite boundaries in each zebrafish. For each set of injections, 15 embryos (i.e. 60-90 sprouts) were examined. Values were expressed as a number of ectopic sprouts per SeA. To examine sprouts in SIV, only the sprouts moving in the ventral direction out of the SIV were counted. Values were expressed as a number of sprouts per zebrafish.

Quantification of cell numbers in segmental artery sprouts: To measure cell proliferation, we counted number of cells (nuclei) in four SeAs in adjacent somite boundaries of Tg(fli1:negfp)y7 zebrafish in which EGFP is expressed only in the nuclei of endothelial cells (35, 39). For each set of injection, 8-9 embryos were examined. Values were then calculated as percentages of the total number of sprouts having a certain number of segmental artery cells.

Morpholino oligonucleotide injections: To knock down gene expression, 8 ng of morpholino oligonucleotides (MO; synthesized by GeneTools) were injected into one-cell stage embryos. A control MO was derived from the AIBP2 sequence, with 5 mismatched oligonucleotides.

```
Control MO:
                                  (SEQ ID NO: 1)
TGAGCTTCATGTTCATTTATTCCGC;

AIBP2 MO:
                                  (SEQ ID NO: 2)
TGTGGTTCATCTTGATTTATTCGGC;

AIBP2 splicing MO:
                                  (SEQ ID NO: 3)
TGTTGAGTGTCAGACAAACCTTGGT;

AIBP1 MO:
                                  (SEQ ID NO: 4)
TCTGTATTCAAATCAGACGCTCAGT;

ABCA1 MO:
                                  (SEQ ID NO: 5)
AACCCAACTGAGTGGAGACAGCCAT;

ABCG1 MO:
                                  (SEQ ID NO: 6)
AAAAGGCTGCCATGAGACATGCCAT.
```

Whole mount in situ hybridization: WISH was carried out as described (38). All WISH probes (39, 40), except AIBP2, were kindly provide by Dr. David Traver (UCSD). Briefly, WT embryos or morphants at indicated developmental stages were fixed with 4% paraformaldehyde and permeabilized with 10 μg/ml protease K (Roche). Subsequently, the embryos were pre-hybridized at 70° C. for 4-6 hours, and then hybridized with a digoxigenin-labeled AIBP2 antisense probe at 65° C. overnight. Both the control sense and probe anti-sense RNA were directly synthesized from AIBP2 full length gene using a Roche T7, T3 or SP6 RNA synthesis kit. After extensive wash, hybridized RNA was detected by immunohistochemistry using an alkaline phosphatase-conjugated antibody against digoxigenin (Roche) and a chromogenic substrate Nitro Blue Tetrazolium (NBT) and 5-Bromo 4-Chloro3Indolyl Phosphate BCIP (38).

Cloning of zebrafish and human AIBP, recombinant protein expression and purification, and antibody production: Zebrafish AIBP2 and AIBP1 were cloned from zebrafish brain cDNA using primers:

```
                                  (SEQ ID NO: 7)
CCGGAATTCCATGTTGGGGGTTCGAGCTCTG(5')
and
                                  (SEQ ID NO: 8)
CGCGGATCCTCAGTTGAGCTGAAACACACTC(3')
for AIBP 1; and (SEQ ID NO: 9)
CCGGAATTCCGCCACCATGAACCACAGCTCCAACG(5')
and
                                  (SEQ ID NO: 10)
CGCGGATCCCGCAGTTCTATAATACATTCTGTGC(3').
for AIBP2
```

The fragments were cloned in frame into pFLAG-CMV (Sigma). Human AIBP was cloned from 293 cell cDNA using primers:

```
                                  (SEQ ID NO: 11)
CGGAATTCCATGTCCAGGCTGCGGGCGCTGCTGGGCCTCG(5'), (SEQ ID NO: 12)
CGGGGTACCTCACTGCAGACGATAGACACACTC(3').
```

For expression of AIBP proteins, the genes were cloned in frame into pHUE vector (41) (kindly provided by Tracy Handel), and expressed in BL21 DE3 competent cells (Invitrogen) and purified with an Ni-NTA agarose resin column (Qiagen). Deubiquitinase (DUB) expressed in pHUE was used as a negative control in experiments with recombinant AIBP. To produce an AIBP2 antibody, 500 µl of 200 µg of recombinant AIBP2 was mixed with 500 µl complete Freund's adjuvant (Sigma) and injected subcutaneously into a guinea pig. The guinea pig was boosted one month later with a subcutaneous injection of 500 µl antigen mixed with incomplete Freund's adjuvant (Sigma), followed by 2 more boosts (intramuscular injections of 200 µg antigen in 1 ml PBS, 2 weeks apart). Post-immune plasma was compared with pre-immune plasma from the same animal and used in western blot to detect AIBP2 in a zebrafish lysate. The specificity of the antibody was confirmed by adding excess of recombinant AIBP2 to the antibody, which prevented its binding to a specific band on western blot.

Transplantation experiments: Cell transplantation was performed as described (39), with different combinations of donors and recipients as indicated in FIG. 1. Donor embryos were of the Tg(fli1:egfp)$^{y1}$ origin, and recipient embryos were of the wild type origin. At the one-cell stage, donor Tg(fli1:egfp)$^{y1}$ embryos were injected with rhodamine-labeled dextran (Mini-Ruby, Invitrogen) as a lineage tracer. At the sphere stage (about 4 hpf), embryos were dechorionated by 0.4 mg/ml pronase (Sigma) and transferred to agarose wells (Adaptive Science Tools, Worcester, Mass.). Approximately 20-40 cells from the margin of a donor embryo were transferred to the margin of a recipient embryo. The recipient embryos were subsequently grown at 28° C. and imaged at 72 hpf. Endothelial cells in chimeric zebrafish originating from donor embryos were visualized by their green fluorescence using a Leica M165FC™ fluorescent stereoscope. For detailed analysis images were captured using a Nikon C1-si™ confocal microscope. Numbers of ectopic branches in each fluorescent SeA were counted.

Microarray: Fifty control MO or AIBP2 MO embryos at 12 and 24 hpf were dechorionated, and total RNA was extracted with a Qiagen's RNEASY KIT™ (RNeasy Kit), with modifications. In brief, dechorionated embryos were immediately placed in RNALATER™ (RNAlater) (Qiagen), and incubated for 10 min at room temperature. The embryos were then homogenized in TRIZOL™ (Invitrogen) for 30 to 60 seconds on ice, chloroform was added and the sample was vortexed for 30 sec, incubated for 5 min at room temperature and centrifuged for 30 min at 13,000 rpm at 4° C. The upper layer was transferred to a new tube, supplemented with 70% ethanol and mixed thoroughly. The sample was then processed according to the RNEASY KIT™ manual. The microarray analysis was performed in UCSD's Biogem Core facility using a Zebrafish (V3) Gene Expression Microarray, 4×44 k™, Cat# G2519F-026437 from Agilent.

Real time PCR: Real time PCR was performed using a ROTOR GENE Q™ qPCR machine (Qiagen). Real time PCR master mix PLATINUMR™ (PlatinumR™) SYBRR Green qPCR SUPERMIX™ was from Invitrogen. The primers were synthesized by IDT. The PCR program was: 50° C. for 2 minutes (UDG incubation), 95° C. for 2 minutes, 40 cycles of: 95° C. for 15 seconds, 60° C. for 1 minute.

Primer Sequences:

```
Fli1a (F):
                                  (SEQ ID NO: 13)
CTTGGCACGTTGCCTTGATAAG,

Fli1 (R):
                                  (SEQ ID NO: 14)
CCTTCATATCTGAGAGTGATCCC;

Flk1 (F):
                                  (SEQ ID NO: 15)
TCCACGAGGGTGGGCAGTCA,

Flk1(R):
                                  (SEQ ID NO: 16)
AGACGGGTGGTGTGGAGTAACGA.

Tie2 (F):
                                  (SEQ ID NO: 17)
GCGATGGATGGCAATAGAGT,

Tie2 (R):
                                  (SEQ ID NO: 18)
CGACAGCAGGATCTGAGAGA;

Kdr (F):
                                  (SEQ ID NO: 19)
TGCCCACATGGAGCTGCTAGCA,

Kdr (R):
                                  (SEQ ID NO: 20)
TGTGGCACATTCAACCACATGAGC.
```

Immunoblot: Zebrafish were lysed on ice with a lysis buffer (50 mM Tris-HCl, pH 7.5, 4 mM sodium deoxycholate, 1% Triton X 100, 150 mM NaCl, 1 mM EDTA, and protease inhibitor cocktail from Sigma). Protein content was determined with a DC protein assay kit (BioRad) and equal protein amounts of the cell lysates were run on a 4-12% Bis-Tris SDS-PAGE with MOPS buffer (Invitrogen) and then transferred to a PVDF membrane (Invitrogen). The blots were probed with appropriate antibodies against specific phosphorylated and non-phosphorylated proteins (Cell Signaling Technology), secondary antibodies conjugated with HRP and developed using a Super Signal West Dura™ substrate (Pierce).

Filipin staining: Zebrafish were fixed with 4% paraformaldehyde overnight at 4° C. The fixed fish were incubated overnight with 0.05% filipin (Sigma) in PBS with 1% sheep serum, washed 3 times with PBS and mounted in glycerol. Images were captured and quantified with a Leica M165FC™ fluorescent stereoscope.

Total lipid extraction and free cholesterol measurements: Total lipid was extracted from zebrafish embryos as we previously described (42). In brief, trunk/tail segments were dissected from fifty 24 hpf embryos and pooled together. The tissue was homogenized and supplemented with 50 µg stigmasterol, an internal standard to control for recovery of extracted sterols. Total lipid extraction was performed with 1:2 methanol/dichloromethane. No saponification of cholesteryl esters was performed because the goal of this study was to measure free cholesterol, the form of cholesterol transferred from the cells via ABC transporters to ApoA-I/HDL. Cholesterol and stigmasterol were measured with a Shimadzu GC-2014™ gas chromatograph using a 30 m×0.25 mm (i.d.) ZB-5HT™ inferno capillary column, film thickness 0.2 µm (Phenomenex). Cholesterol levels were normalized to protein and then to the levels in embryos injected with control MO.

Cholesterol efflux: A cholesterol efflux assay was performed as described (28, 43), with modifications. In brief, human umbilical vein endothelial cells (HUVEC; from ATCC) were loaded with 2 µCi/ml 3H-cholesterol in 5% fetal bovine serum-supplemented EBM media (Lonza). Twenty-four hours later, cells were washed and equilibrated for 1 hour with DMEM containing 0.2% bovine serum albumin (BSA). The cells were washed with PBS and cholesterol efflux was initiated by the addition of 0.2% BSA/DMEM with 50 µg/ml HDL3 (isolated from normolipidemic human plasma by ultracentrifugation), in the presence or absence of 0.2 µg/ml AIBP2, AIBP1, or hAIBP. Replacing AIBP with deubiquitinase (DUB) was used as a negative control. Background, non-specific release of 3H-cholesterol was measured in 0.2% BSA/DMEM, in the absence of HDL or any other protein. After 1 to 6 hours of incubation, the medium was collected and counted in a multipurpose liquid scintillation counter LS 6500™ (Beckman Coulter). The cells were extracted with 2-propanol, the lipid extract evaporated under argon gas, resuspended in 2-propanol and then added to SCINTIVERSE BD COCKTAIL™ (Fisher), and counted. Cholesterol efflux was expressed as a percentage of 3H counts in the medium compared to total 3H counts in the cells and the medium. Background, non-specific release of 3H from the cells was subtracted.

ABCG1 knockdown: Both negative control and ABCG1 siRNA oligonucleotides were from Ambion. HUVEC were plated in 24-well plates at $1\square \times 10^5$ cells/well and transfected with 20 nM siRNA using SUPERFECT TRANSFECTION REAGENT™ (Qiagen) as described in the manufacturer's protocol. Two days after transfection, cells were washed and used in an efflux assay. Two additional wells of transfected cells were used to confirm ABCG1 knockdown in western blot using an antibody from Novus Biologicals.

In vitro angiogenesis assay: The angiogenesis assay was carried out as described in (44). Growth factor reduced MATRIGEL™ (BD Biosciences) was thawed at 4<C overnight and diluted with an equal volume of serum-free EBM medium (Lonza). Each well of pre-chilled 96-well plates was coated with 50 µl diluted Matrigel and incubated at 37<C for 1 hour. HUVECs were serum-starved for 2 days and then pre-incubated for 4 hours with 50 µg/ml HLD3, 0.1 µg/ml hAIBP, or 50 µg/ml HLD3+0.1 µg/ml hAIBP. Cells were harvested and added to Matrigel-coated plates at $1 \times 10^4$ cells per well in EBM supplemented with 2% LPDS, in the presence or absence of 20 ng/ml VEGF. Tubular structures were imaged following a 12 hour incubation with a phase contrast microscope.

Example 2: Exemplary Compounds and Methods of the Invention Regulate Cholesterol Transport and Angiogenesis: Control of Angiogenesis by AIBP-Mediated Cholesterol Efflux This example describes and demonstrates exemplary activities, and the efficacy, of compounds and methods of the invention. We investigated whether human AIBP (hAIBP) would have any effect on cholesterol efflux from EC to HDL.

In human umbilical vein endothelial cells (HUVEC), ABCG1 is a major cellular transporter responsible for cholesterol efflux to HDL (10, 11). In the presence of hAIBP, cholesterol efflux from HUVEC to HDL3 was increased 2-fold, and the ABCG1 deficiency completely abrogated this effect (FIG. 12a). Increased cholesterol efflux in the presence of hAIBP was observed within first 4 hours of incubation and then, at 6 hours, leveled off with the cholesterol efflux to HDL3 in the absence of hAIBP.

To investigate the role of AIBP/HDL-mediated cholesterol efflux in angiogenesis, we added hAIBP, in the presence or absence of HDL3, to HUVEC and stimulated cells with VEGF. hAIBP and HDL3 added separately did not affect EC tube formation, but together they completely blocked angiogenesis (FIG. 12b). If the hAIBP/HDL inhibition of angiogenesis is the consequence of accelerated cholesterol efflux, then this effect should depend on the presence of the cholesterol transporter ABCG1. Indeed, knockdown of ABCG1 in HUVEC rescued VEGF-induced angiogenesis from the hAIBP inhibition (FIG. 12c). ABCG1-mediated depletion of cholesterol from plasma membrane disrupts cholesterol- and sphingolipid-rich membrane microdomains 12, often designated as lipid rafts, and affects surface receptor signalling (13,14). Adding hAIBP/HDL3 significantly reduced lipid raft content in HUVEC (FIG. 12d). Accordingly, VEGF-induced phosphorylation of VEGFR2, Akt, FAK, Src and to a lesser degree of ERK1/2 were reduced in HUVEC pretreated with hAIBP/HDL3, but not with hAIBP or HDL3 alone (FIG. 12e). Consistent with the effect on VEGF signalling, HUVEC migration toward the VEGF cue was significantly reduced in hAIBP/HDL3-treated cells. These results demonstrate that hAIBP/ABCG1-mediated cholesterol efflux to HDL disrupts lipid rafts and VEGF signalling in HUVEC and thereby inhibits VEGF-induced angiogenesis.

AIBP is evolutionary conserved from *Drosophila* to zebrafish to mouse and human. Zebrafish have two AIBP genes, apoa1bp1 and apoa1bp2. Both proteins bound to human ApoA-I and to the HDL in human plasma. In a HUVEC cholesterol efflux assay, zAibp2 was as effective in promoting cholesterol efflux to HDL3 as hAIBP, with zAibp1 having a lesser effect.

To demonstrate that the AIBP effect on angiogenesis is not restricted to HUVEC, we tested both hAIBP and zAibp2 in an ex vivo aortic ring angiogenesis assay. A cluster of HEK293 cells producing either hAIBP or zAibp2 was placed in close proximity to a mouse aortic ring, and then angiogenesis was stimulated with addition of VEGF. Both hAIBP and zAibp2 completely abrogated aortic ring neovascularization (FIG. 12f).

To investigate whether zAibp2 plays any role in zebrafish cholesterol metabolism, we injected one-cell stage embryos of wild type zebrafish with antisense morpholino oligonucleotides (MO) targeting zaibp2 translation sites or with scrambled control MO. At 24 hours post fertilization (hpf) the embryos were stained with filipin, a fluorescent dye that specifically binds to free (unesterified) cholesterol. The filipin fluorescence was increased in the body of zaibp2 morphants (excluding the yolk) compared to controls (FIG. 13a, 13b). These results were confirmed with direct gas chromatography measurements of free cholesterol in lipid extracts from pooled de-yolked embryos (FIG. 13c). Increased levels of free cholesterol measured by two independent techniques suggest that zAibp2 regulates cholesterol metabolism and, thus, based on the in vitro results shown in FIG. 12, may control angiogenesis. Indeed, injection of MO targeting translation sites of zaibp2 into one-cell stage embryos of Tg(fli1-egfp)y1 zebrafish, which express EGFP in EC15, resulted in remarkable dysregulation of angiogenesis.

Profound ectopic branching of both segmental arteries (SeA) and subintestinal veins (SIV) were found in zaibp2 morphants (FIG. 13d, 13e), whereas no obvious abnormalities were observed in zaibp1 morphants (data not shown). Similar results were observed with the MO targeting a zaibp2 splicing site. The zaibp2 knockdown was validated in western blot (see FIG. 14D, 14E). The ectopic branching of SeAs in zaibp2 morphants was partially rescued by forced expression of zaibp2 mRNA lacking the MO target site (FIG. 13f).

Next, the tissue distribution of zaibp2 in embryos at different developmental stages was examined by whole embryo in situ hybridization (WISH). zaibp2 expression was detected as early as 20 min post fertilization and, notably, zaibp2 mRNA at 24 hpf was expressed within the somites (FIG. 14a). The zaibp2 expression pattern resembles that of type 3 semaphorins, non-cell autonomous repellent cues that guide the patterning of developing SeAs via endothelial-specific PlexinD1 receptors (16,17). To determine the cell autonomy of zAibp2 effect on angiogenesis, we performed cell transplantation experiments, using Tg(fli1:egfp)$^{y1}$ donors and non-transgenic recipients. Fluorescent EC from wild type donors found in non-fluorescent zaibp2 morphants displayed excessive branching and filopodial projections (FIG. 14b).

In contrast, fluorescent EC from zaibp2 morphant donors found in wild type recipients had normal morphology. In a gain-of-function experiment, ectopic expression of zAibp2 (and DsRed as a fluorescent tracer) in somites, driven by myog:Gal4 and bi-directional 10×UAS promoters, inhibited SeA sprouting from the dorsal aorta and normal growth of sprouted SeA (FIG. 14c). These results demonstrate a role for zAibp2 as a repellent molecule whose function depends on the milieu surrounding EC but not on zAibp2 expression in the EC themselves.

The impact of the loss of zAibp2 on molecular pathways involved in angiogenesis was examined in control and zaibp2 morphants using microarrays. Genes indicative of enhanced cell proliferation and genes involved in angiogenesis, such as tie2, vegfr2, vegfr3 and fli1, were upregulated in zaibp2 morphants. Increased expression of genes involved in angiogenesis was confirmed by both qRT-PCR and WISH (FIG. 14d). Lysates of zaibp2 knockdown embryos displayed robust phosphorylation of Akt, VEGFR2 and Src, but not of ERK1/2 (FIG. 14e). These results demonstrate that the molecular pathways that orchestrate angiogenesis are dramatically affected by zaibp2 knockdown.

To further test the hypothesis that effective cholesterol efflux is required for normal angiogenesis, we knocked down zebrafish abca1 and abcg1. Expression of abca1 and abcg1 has been found in zebrafish and, as in mammals, it is induced by liver X receptor agonists (18,19). As in zaibp2 morphants, lysates of zebrafish injected with abca1+abcg1 MO displayed increased levels of phosphorylated Akt, VEGFR2 and Src (FIG. 14e). The abcg1 knockdown was confirmed as shown in Supplementary FIG. 11.

Further, we found that the loss of Abca1 and Abcg1 in zebrafish closely reproduced the vascular developmental defects of zaibp2 morphants, in both SeA and, markedly, in SIV vascular beds (FIG. 15a). As expected, abca1/abcg1 morphants had higher levels of free cholesterol than control larvae.

In agreement with the zaibp2 knockdown results, overexpression of zAibp2-mCherry in somites resulted in inhibition of SeA growth and incomplete SeA angiogenesis (FIG. 15b). Remarkably, the inhibition of SeA formation induced by ectopic zAibp2-mCherry expression was rescued by knocking down abca1/abcg1. These results provide additional evidence that expression of zAibp2 limits blood vessel growth and also suggest that Abcg1 and/or Abca1 are required for zAibp2 function in cholesterol efflux. The latter conclusion agrees with the results that ABCG1 is required for hAIBP inhibition of HUVEC tube formation (FIG. 12a). The findings of this work demonstrate that effective cholesterol efflux is necessary for proper sprouting, branching and growth of blood vessels in vivo.

Furthermore, we identified Aibp as a novel factor controlling zebrafish angiogenesis and suggested the mechanism in which Aibp functions as a non-cell autonomous positive regulator of cholesterol efflux from EC. Because in 24 hpf zebrafish Aibp is highly expressed in somites (FIG. 14a), it is likely that it promotes lateral cholesterol efflux from EC of growing SeA, reduces lipid rafts and inhibits local VEGF signaling, thus preventing ectopic SeA growth through the somites. Because VEGFR signaling requires receptor dimerization (20), which occurs in lipid raft microdomains (13), AIBP-mediated cholesterol efflux and associated reduction of lipid rafts provide a new level of paracrine regulation for the VEGFR pathway.

In addition, a role for AIBP in facilitating Notch and/or PlxnD1 signaling, key negative regulators of angiogenesis (21-23), cannot be excluded. The role of cholesterol efflux mechanisms in protecting against endothelial dysfunction, in particular in hypercholesterolemic animals prone to development of atherosclerosis, has been reported (11, 24). However, our study is the first to demonstrate the importance of cholesterol efflux in regulation of angiogenesis.

The reports showing modulation of angiogenesis by statins, inhibitors of HMG-CoA reductase, demonstrate that the statins' effects are due to changes in prenylation of signaling proteins, not in cholesterol levels (25, 26). Furthermore, our study for the first time demonstrates the role of AIBP in cholesterol efflux from EC and in vivo angiogenesis. In vitro and ex vivo experiments with hAIBP, HUVEC and mouse aortic tissue imply that the importance of AIBP extends beyond regulation of zebrafish angiogenesis and that AIBP may play a role in mammalian angiogenesis as well.

Interestingly, treatment of rat aortic rings with VEGF significantly reduces Aibp mRNA expression (27), implying that downregulation of AIBP is required for neovascularization. It is noteworthy that the human APOA1BP gene is located at the chromosome 1 locus for familial combined hyperlipidemia and that APOA1BP is differentially expressed in many angiogenic tumors (28, 29).

This invention demonstrates that AIBP functions in embryonic angiogenesis and the results of our ex vivo and in vitro experiments demonstrate the role of AIBP in a variety of pathologic and regenerative processes in humans, from cancer to cardiovascular disease.

Methods—Example 2

Human and zebrafish AIBP were cloned, expressed and purified using standard techniques, and used in in vitro cholesterol efflux and angiogenesis assays as described (11, 24, 30). In vivo angiogenesis was monitored in Tg(fli1:egfp) y1 zebrafish in which zaibp2 was ectopically expressed or zaibp2 and/or abca1 and abcg1 were knocked down by antisense MO. VEGFR expression and signaling were detected by qPCR and immunoblot.

See also methods as set forth in Example 1.

Figure Legends—Example 2

FIG. 12. Role of AIBP in cholesterol efflux from EC and in vitro angiogenesis:
FIG. 12a, Effect of ABCG1 knockdown on hAIBP mediated-cholesterol efflux. HUVEC were transfected with control or ABCG1 siRNA. The ABCG1 knockdown was confirmed in western blot. HUVEC were preloaded with 3H-cholesterol and then incubated for 1 hour with 50 µg/ml HDL3 in the presence or absence of 0.2 µg/ml hAIBP. The media and cell lysates were collected and 3H counts were measured. Efflux was measured as the 3H counts in the medium divided by the sum of 3H counts in the medium and the cell lysates. Mean±SE; n=6; *, p<0.05; **, p<0.01.

FIG. 12b, Effect of hAIBP and HDL3 on EC tube formation. HUVEC were preincubated with 50 µg/ml HDL3, 0.1 µg/ml hAIBP, or 50 µg/ml/ml HDL3+0.1 µg/ml hAIBP for 4 hours. Cells were then seeded on Matrigel, in the presence or absence of 20 ng/ml VEGF, and imaged following a 12 hour incubation. Scale, 100 µm. The length of EC tubes was measured. Mean±SE; n=5. *, p<0.05; ***, p<0.001.

FIG. 12c, Requirement for ABCG1 in hAIBP inhibition of angiogenesis. HUVEC were transfected with control or ABCG1 siRNA and used in a EC tube formation assay as in panel C. Mean±SE; n=6. ***, p<0.001.

FIG. 12d, Effect of hAIBP and HDL3 on lipid rafts. HUVEC were preincubated with 50 µg/ml HDL3, 0.1 µg/ml hAIBP, or 50 µg/ml/ml HDL3+0.1 µg/ml hAIBP for 4 hours. Cells were stained for nuclei (blue, DAPI) and for lipid rafts (red, cholera toxin B (CTB) and anti-CTB antibody), and the area of lipid rafts per cell were measured. Mean±SE; n=10. **, p<0.01; #, p=0.08.

FIG. 12e, Effect of hAIBP on VEGF signaling. HUVEC were preincubated with 50 µg/ml HDL3, 0.2 µg/ml hAIBP, or 50 µg/ml HDL3+0.2 µg/ml hAIBP for 4 hours, followed by a 20 min stimulation with 50 ng/ml VEGF. Cells were lysed, and the lysates run on SDS-PAGE and probed as indicated.

FIG. 12f, Aortic ring angiogenesis assay. Aorta was isolated from a C57BL6 mouse and sliced into 1 mm wide rings. The aortic rings were embedded in Matrigel. HEK293 cells expressing zAibp2 or hAIBP were inserted approximately 0.5 mm away from the aortic ring, and the plates were incubated with 10 ng/ml VEGF for 7 days. Images show the edge of the aortic rings facing the HEK293 cell plaques. Immunoblots show expression of hAIBP and zAibp2 in HEK293 cells.

FIG. 13 effect of AIBP deficiency on zebrafish cholesterol metabolism and angiogenesis:

FIG. 13a-c. Free cholesterol levels in zaibp2 morphants. a, One-cell stage AB zebrafish embryos were injected with 8 ng of either control MO or zaibp2 MO targeting ATG translation site. Twenty four hpf control and zaibp2 morphants were fixed and stained with filipin to detect free cholesterol in embryos. Note the yolks are artificially masked on the images.

FIG. 13b. Intensities of filipin fluorescence in images shown in panel A (without yolks) were quantified in 12-15 embryos per group. *, p<0.05.

FIG. 13c. At 24 hpf, the trunk area (without yolk and head) was dissected and total lipids were extracted. Free cholesterol levels were determined by GC. The cholesterol levels were normalized to the protein content and then to the values in control MO embryos. 50-70 embryos were pooled for each sample. The data are from 3-4 independent experiments. *, p<0.05.

FIG. 13d-f. Angiogenic defects in zaibp2 morphants. One-cell stage Tg(fli1:egfp)y1 zebrafish embryos were injected with 8 ng of either control MO or zaibp2 MO targeting ATG translation site.

FIG. 13d. Low magnification, bright field images showing the area of fluorescent imaging of SeA (white box) and SIV (red box).

FIG. 13e. The images of SeA in 30 hpf embryos (top row), and SeA (images 1-2) and of SIV (3-4) in 3 dpf embryos. Arrows point to dysregulated sprouts. Scale in all images, 25 m.

FIG. 13f. Quantification of the number of embryos with normal and abnormal angiogenesis (SeA with ectopic branching) resulting from injection of control or zaibp2 MO. The abnormal angiogenesis was partially rescued by co-injection of 40 pg of zaibp2 mRNA lacking the MO targeting site. 100-149 embryos per group. ***, p<0.001.

FIG. 14. Effect of AIBP deficiency and ectopic overexpression on zebrafish angiogenesis and VEGF signaling.

FIG. 14a, Tissue distribution of zaibp2 mRNA in zebrafish embryo. Embryos at different developmental stages were fixed and WISH was performed with an antisense zaibp2 probe. Scale, 100 µm.

FIG. 14b, Mosaic expression analysis of EC branching in WT and zaibp2 knockdown embryos. At 4 hpf, cells were isolated from donor embryos and transplanted into recipient embryos (details of donor and recipient embryos are depicted above images). Three days after transplantation, the recipient embryos were analyzed. Red arrowheads indicate aberrant ectopic branches/sprouts. Scale, 20 µm. The graph quantifies numbers of ectopic branches/filopodial projections per SeA. 8-16 embryos per group. ***, p<0.001.

FIG. 14c, Ectopic expression of zAibp2 inhibits SeA growth. One-cell stage Tg(fli1:egfp)y1 embryos were injected with 2 nl of 100 ng/µl DNA constructs for myog:Gal4, DsRed: 10×UAS:zAibp2 or myog:Gal4, DsRed:10×UAS expression. Images were captured at 30 hpf. Arrowheads point to aberrant SeA growth, close to the sites of DsRed (and zAibp2) expression.

FIG. 14d, Expression of genes involved in angiogenesis. Total RNA was isolated from 24 hpf control and zaibp2 morphants and qRT-PCR was performed. The results are normalized to actin. The results are from a pool of 50 embryos per group, 3-4 replicates.*, p<0.001; , p<0.01; *, p<0.05.

FIG. 14e, Phosphorylation of signaling proteins. Lysates of 24 hpf control (8 ng control MO), zaibp2 (8 ng zaibp2 MO) and abca1/g1 (4 ng abca1 MO+4ng abcg1 MO) morphants were separated on SDSPAGE and immunoblotted as indicated.

FIG. 15 Role of Abca1 and Abcg1 in angiogenesis and in mediating effects of Aibp.

FIG. 15a, Angiogenic defects in abca1/g1 morphants. One-cell stage embryos were injected with 8 ng of control MO, 8 ng zaibp2 MO, or 4 ng abca1 MO+4 ng abcg1 MO. Images of SeA (30 hpf) and SIV (3 dpf) are shown. Scale, 50 µm. Graphs show numbers and of SeA ectopic branches and numbers and length of SIV ectopic sprouts from 5-12 embryos.***, p<0.001.

FIG. 15b, Rescue of the effect of zAibp2 overexpression in abca1/g1 morphants. One-cell stage embryos were injected with 2 nl of 100 ng/µl myog:zAibp2-mCherry plasmid, myog:zAibp2-mCherry plasmid together with abca1/g1 MO, or myog:mCherry plasmid. The arrow points to an aberrant SeA at the site of zAibp2-mCherry expression. Scale, 20 m. Abnormal SeA formation was quantified in 8-16 embryos per group. **, p<0.01.

Example 3: Exemplary Compounds and Methods of the Invention Regulate Cholesterol Transport and Angiogenesis: Control of Angiogenesis by AIBP-Mediated Cholesterol Efflux This example describes and demonstrates exemplary activities, and the efficacy, of compounds and methods of the invention. This example demonstrates that ApoA-I binding protein (AIBP) accelerates cholesterol efflux from endothelial cells (EC) to HDL and thereby regulates angiogenesis. AIBP/HDL-mediated cholesterol depletion reduces lipid rafts, interferes with VEGFR2 dimerization and signaling, and inhibits VEGF-induced angiogenesis in vitro and mouse aortic neovascularization ex vivo. Aibp regulates the membrane lipid order in embryonic zebrafish vasculature and functions as a non-cell autonomous regulator of zebrafish angiogenesis. Aibp knockdown results in dysregulated sprouting/branching angiogenesis, while forced Aibp expression inhibits angiogenesis. Dysregulated angiogenesis is phenocopied in Abca1/Abcg1-deficient embryos, and cholesterol levels are increased in Aibp-deficient and Abca1/Abcg1-deficient embryos. Our findings demonstrate that secreted AIBP positively regulates cholesterol efflux from EC and that effective cholesterol efflux is critical for proper angiogenesis.

First, we investigated whether human AIBP (hAIBP) had any effect on cholesterol removal from human umbilical vein endothelial cells (HUVEC) in which ABCG1 is a major transporter responsible for cholesterol efflux to HDL[9,10]. In the presence of hAIBP, cholesterol efflux from HUVEC to $HDL_3$ was increased 2-fold, and the ABCG1 deficiency completely abrogated this effect (FIG. 16a, FIG. 21). hAIBP did not promote cholesterol efflux in absence of $HDL_3$ (FIG. 21b), but the hAIBP binding to HUVEC (FIG. 22) increased the overall HUVEC capacity to bind $HDL_3$ ($B_{max}$=1.5 vs. 0.8) and the constant of $HDL_3$ dissociation from HUVEC ($Kd=1.0\times10^{-6}$ M vs. $0.33\times10^{-6}$ M; FIGS. 1b, c), thereby creating conditions that would facilitate $HDL_3$-mediated cholesterol efflux.

To investigate the role of AIBP/HDL-mediated cholesterol efflux in angiogenesis, we incubated HUVEC with hAIBP and/or $HDL_3$ and then stimulated cells with VEGF. hAIBP and $HDL_3$ added separately did not affect EC tube formation, but together they significantly reduced angiogenesis (FIG. 16d, e and Supplementary FIG. 4). Cholesterol depletion by methyl-β-cyclodextrin (MβCD)[11] also inhibited angiogenesis, whereas cholesterol-loaded MβCD, which delivers cholesterol to the cell, promoted angiogenesis (FIG. 23). If the hAIBP/$HDL_3$ inhibition of angiogenesis is the consequence of accelerated cholesterol efflux, then this effect should depend on the presence of the cholesterol transporter ABCG1. Indeed, knockdown of ABCG1 in HUVEC rescued VEGF-induced angiogenesis from the hAIBP/$HDL_3$ inhibition (FIG. 16f). Further, we tested both hAIBP and zAibp2 (a zebrafish protein, which will be discussed later) in an ex vivo aortic ring angiogenesis assay. A cluster of HEK293 cells producing either hAIBP, zAibp2 or mCherry (negative control) was placed 0.5 mm from the edge of a mouse aortic ring, and VEGF was added to stimulate angiogenesis. Both hAIBP and zAibp2, but not mCherry, significantly reduced neovascularization of aortic rings isolated from a wild type mouse (FIGS. 1g, h). Aortic rings from an $Abcg1^{-/-}$ mouse responded to VEGF with a more vigorous angiogenesis, which was not significantly reduced by hAIBP or zAibp2. These results support the hypothesis that cholesterol efflux is necessary for the AIBP-mediated inhibition of angiogenesis.

HDL-mediated depletion of cholesterol from plasma membrane disrupts cholesterol- and sphingomyelin-rich membrane microdomains[12,13], often designated as lipid rafts, and affects membrane receptor signaling[11]. We found that hAIBP/$HDL_3$ reduced the lipid raft content in HUVEC and disrupted cell-surface colocalization of caveolin-1 and VEGFR2 (FIGS. 17a-c and FIG. 24). The hAIBP/$HDL_3$ treatment, similarly to the treatment with MβCD, decreased VEGFR2 and caveolin-1 localization to the lipid raft fraction isolated from cell lysates (FIG. 17d and FIG. 25). Many studies suggest that VEGFR2 localization to lipid rafts facilitates VEGFR2 dimerization and endocytosis[14-17], the steps required for VEGF-mediated signaling[18]. In our experiments, the hAIBP/$HDL_3$ treatment reduced VEGF-induced VEGFR2 dimerization and endocytosis as well as phosphorylation of VEGFR2, Akt, FAK, Src and to a lesser degree of ERK1/2 (FIGS. 17e-g and FIG. 25, FIG. 26, FIG. 27). Importantly, subsequent addition of cholesterol partially reversed inhibition of VEGFR2, FAK and Akt phosphorylation in hAIBP/$HDL_3$-treated cells (FIG. 28). Consistent with the effect on VEGF signaling, HUVEC migration toward a VEGF cue was significantly reduced in hAIBP/$HDL_3$-treated cells (FIG. 29). These results demonstrate that hAIBP facilitates cholesterol efflux from HUVEC to HDL and that cholesterol depletion of the plasma membrane disrupts lipid rafts and VEGF signaling and inhibits VEGF-induced angiogenesis.

AIBP is evolutionary conserved from *Drosophila* to zebrafish to mouse and human. Zebrafish have two genes, apoa1bp1 and apoa1bp2, encoding zAibp1 and zAibp2 proteins, respectively. The zaibp2 expression in 24-36 hours post-fertilization (hpf) zebrafish embryos shows a clear segmental pattern, colocalizing with the somite marker myod (FIG. 18a and FIG. 30). By 48 hpf, when segmental angiogenesis is completed, zaibp2 is no longer expressed in somites.

Both zAibp2 and zAibp1 bound to human ApoA-I and to the HDL in human plasma, but only zAibp2 was effective in promoting cholesterol efflux from HUVEC to $HDL_3$ (FIG. 31, FIG. 32). Zebrafish embryos injected with antisense morpholino oligonucleotides (MO) targeting zaibp2 translation sites had increased levels of free (unesterified) cholesterol, whereas injections of zaibp1 or scrambled control MO did not result in any changes (FIGS. 18b, c and FIG. 32). Thus, we focused on zaibp2. Using the polarity-sensitive fluorescent probe Laurdan, we observed a higher membrane lipid order in the areas of growing segmental arteries (SeA) corresponding to tip cells compared to stalk cells (FIG. 18d, e), suggesting a higher content of lipid rafts in tip cells, which may positively regulate Vegfr2 signaling. The membrane lipid order was increased in the SeA of zaibp2 morphants compared to controls, and the difference between tip and stalk cells was lost. To test the hypothesis that zAibp2-mediated cholesterol efflux regulates membrane order in growing SeA, we injected zaibp2 morphants with human $HDL_3$ or with BSA. Adding an excess of $HDL_3$—to promote cholesterol efflux and to override the zAibp2 deficiency—annulled the increase in membrane order in SeA of zaibp2 morphants, and a spatially indiscriminate $HDL_3$ excess equalized the membrane order in tip and stalk cells. Adding an excess of BSA had no effect on the membrane order in zaibp2 morphants. Lysates of zaibp2 knockdown embryos displayed increased phosphorylation of Vegfr2, Akt and Src, and decreased phosphorylation of Erk1 (FIG. 18f, FIG. 33, FIG. 34). These results demonstrate that zAibp2 regulates cholesterol levels, the membrane lipid order, and Vegfr2 signaling controls angiogenesis.

Injection of MOs targeting zaibp2 translation or splicing sites into one-cell stage embryos of Tg(fli1:eg4)$^{y1}$ zebrafish, which express EGFP in EC[19], resulted in remarkable dysregulation of angiogenesis, with profound ectopic branching of both SeA and subintestinal veins (SIV) (FIG. 18g and FIG. 35, FIG. 36). The zaibp2 knockdown was validated in western blot (FIG. 3f). The ectopic branching of SeAs in zaibp2 morphants was partially rescued by forced expression of zaibp2 mRNA lacking the MO target site (FIG. 18h).

The zaibp2 expression pattern (FIG. 18a) resembles that of type 3 semaphorins, non-cell autonomous repellent cues that guide the patterning of developing SeAs via endothelial-specific PlexinD1 receptors[20]. To determine the cell autonomy of the zAibp2 effect on angiogenesis, we performed cell transplantation experiments, using Tg(fli1: egfp)$^{y1}$ donors. Fluorescent EC from wild type donors found in non-fluorescent zaibp2 morphants displayed excessive branching and filopodial projections, while fluorescent EC from zaibp2 morphant donors found in wild type recipients had normal morphology (FIGS. 19a, b). In a gain-of-function experiment, overexpression of zAibp2 inhibited SeA sprouting from the dorsal aorta and normal growth of sprouted SeA (FIG. 36). These results suggest a role for zAibp2 as a repellent molecule whose function depends on the milieu surrounding EC but not on zAibp2 expression in the EC themselves.

The loss of zAibp2 resulted in increased expression of genes involved in angiogenesis, such as tie2, vegfr2, vegfr3 and fli1 (FIG. 37A, FIG. 37B, FIG. 38A). Thus, in addition to the zAibp2 effect on the membrane lipid order and Vegfr2 signaling (FIGS. 18d-f), zAibp2 affects expression of angiogenic genes as well.

To further validate that effective cholesterol efflux is required for normal angiogenesis, we knocked down zebrafish cholesterol transporters abca1 and abcg1[21,22] and observed higher levels of free cholesterol, increased levels of phosphorylated Akt, Vegfr2 and Src and dysregulated SeA and SIV angiogenesis (FIGS. 18f, 19c and FIG. 38B, FIG. 39A, FIG. 39B), closely reproducing the angiogenesis defects of zaibp2 morphants. Individual knockdown of each abca1 and abcg1 suggested a dominant role of abca1 in embryonic angiogenesis. In contrast to the zaibp2 non-cell autonomous regulation of angiogenesis, fluorescent EC from abca1/abcg1 morphant donors found in wild type recipients displayed excessive SeA branching (FIGS. 19a, b), confirming that cholesterol efflux from EC is required to restrain ectopic angiogenesis. Overexpression of zAibp2-mCherry in somites resulted in inhibition of SeA growth, which was rescued by knocking down abca1/abcg1 (FIGS. 19d, e). These results provide additional evidence that expression of zAibp2 limits blood vessel growth and also suggest that zebrafish Abca1- and/or Abcg1-mediated cholesterol efflux is required for the zAibp2 effect on angiogenesis.

Based on our results, we propose that there is an additional level of paracrine regulation for the VEGFR2 pathway in which cholesterol efflux and associated reduction of ordered membrane microdomains/lipid rafts interfere with the VEGFR2 membrane localization, dimerization, endocytosis, and signaling. Because in 24 hpf zebrafish zaibp2 mRNA is highly expressed in somites, but not in the inter-somitic spaces where SeA grow, it is likely that zAibp2-mediated cholesterol efflux inhibits Vegfr2 signaling in a site-specific manner to prevent lateral protrusions from stalk and tip cells and restrains ectopic SeA growth into somites (FIG. 20).

The role of cholesterol efflux mechanisms in protecting against endothelial dysfunction, in particular in hypercholesterolemic animals prone to development of atherosclerosis, has been reported[10,23]. However, our study is the first to demonstrate the role of AIBP in promoting cholesterol efflux from EC to HDL and the importance of this mechanism in regulation of angiogenesis. In contrast to the ApoA-I-containing HDL, ApoB-containing LDL and VLDL deliver cholesterol and other lipids to the cell and, thus, are positioned to promote angiogenesis.

Interestingly, a recent paper finds the opposite, that ApoB lipoproteins negatively regulate angiogenesis in zebrafish embryos[24]. The ApoB protein, but not the lipid components within ApoB-containing lipoproteins, may be responsible for transcriptional regulation of Vegfr1, a soluble decoy receptor for Vegf.

Our experiments uncovered a different, lipid-mediated mechanism in which effective cholesterol efflux is a critical process that ensures proper angiogenesis and Aibp secreted by the surrounding tissues serves as an important negative regulator of angiogenesis.

Figure Legends—Example 3

FIG. 16. Role of AIBP in cholesterol efflux from EC and in vitro angiogenesis.

FIG. 16a, hAIBP mediated-cholesterol efflux and effect of ABCG1 knockdown. HUVEC were transfected with control or ABCG1 siRNA, preloaded with $^3$H-cholesterol and incubated for 1 hour with 50 µg/ml $HDL_3$ in the presence or absence of 0.2 µg/ml hAIBP. Efflux was measured as the $^3$H counts in the medium divided by the sum of $^3$H counts in the medium and the cell lysate. Mean±SE; n=6.

FIG. 16b and FIG. 16c, Effect of hAIBP on $HDL_3$ binding to HUVEC. HUVEC were incubated on ice with the indicated concentration of biotinylated $HDL_3$ (b-$HDL_3$), in the presence or absence of hAIBP (at a 0.1:50 w/w hAIBP:$HDL_3$ ratio) and 40× excess of unlabeled HDL. Each data point is Mean±SE from 3 to 7 independent experiments. The binding parameters for b-$HDL_3$/HUVEC binding were calculated as $B_{max}$=0.8±0.1 and $K_d$=(0.33±0.10)×$10^{-6}$ M in absence of hAIBP (panel b; $R^2$=0.92, Sy.x=0.1), and $B_{max}$=1.5±0.4 and $K_d$=(1.03+0.5)×$10^{-6}$ M in the presence of hAIBP (panel c; $R^2$=0.94, Sy.x=0.1). The differences in $B_{max}$ and $K_d$ values were statistically significant ($p<0.01$ and $p<0.05$, respectively).

FIG. 16d, Effect of hAIBP and $HDL_3$ on EC tube formation. HUVEC were preincubated with or without 50 µg/ml $HDL_3$+0.1 µg/ml hAIBP for 4 hours. Cells were then seeded on Matrigel, in the presence or absence of 20 ng/ml VEGF, and imaged following a 12-hour incubation. Scale, 100 µm. e, The length of EC tubes in the experiment shown in panel d. Mean±SE; n=5.

FIG. 16f, Requirement for ABCG1 in hAIBP inhibition of angiogenesis. HUVEC were transfected with control or ABCG1 siRNA and assayed as in panel d. Mean±SE; n=6.

FIG. 16g, Mouse aortic ring angiogenesis assay. Aortic rings from C57BL6 and Abcg1$^{-/-}$ mice were embedded in Matrigel. HEK293 cells transiently expressing mCherry, zAibp2 or hAIBP were inserted approximately 0.5 mm away from the aortic ring, and the plates were incubated with 10 ng/ml VEGF for 7 days. Images show the edge of the aortic rings facing the HEK293 cell clusters. Immunoblots show expression of hAIBP and zAibp2 (both detected with a Flag tag antibody) and mCherry in HEK293 cells. h, The length of aortic ring sprouts. Mean±SE; n=10.

In all panels: #, not significant; *, $p<0.05$; , $p<0.01$; *, $p<0.001$.

FIG. 17 Effect of AIBP on HUVEC lipid rafts, VEGFR2 localization, dimerization and signaling.

FIG. 17a, Effect of hAIBP and $HDL_3$ on lipid rafts. HUVEC were preincubated with 50 µg/ml $HDL_3$, 0.1 µg/ml hAIBP, or 50 □g/ml $HDL_3$+0.1 µg/ml hAIBP for 4 hours. Cells were stained for nuclei (blue, DAPI) and for lipid rafts (red, cholera toxin B (CTB) and anti-CTB antibody). Scale, 10 µm. b, The area of lipid rafts per cell. Mean±SE; n=10; **, p<0.01; #, p=0.08.

FIG. 17c, Effect of hAIBP and $HDL_3$ on caveolin-1 and VEGFR2 surface localization. HUVEC were incubated with hAIBP and/or $HDL_3$ as in 2a, fixed and stained with antibodies to caveolin-1 and VEGFR2. Images were captured using TIRF microscopy and Pearson's coefficient was calculated to assess surface colocalization of VEGFR2 with caveolin-1. Mean±SE; n=38-50; ***, p<0.001.

FIG. 17d, VEGFR2 and caveolin-1 localization to lipid rafts. HUVEC were incubated with 20 µg/ml cholesterol-MβCD for six hours, followed by a 1 hour incubation with or without 50 µg/ml $HDL_3$+0.1 µg/ml hAIBP, or a 30 min incubation with 10 mM MβCD. HUVEC lysates were separated into lipid rafts and non-lipid rafts fractions by ultracentrifugation, run on SDS-PAGE and blotted with VEGFR2 and caveolin-1 antibodies.

FIG. 17e, Effect of hAIBP and $HDL_3$ on VEGFR2 dimerization. HUVEC were preincubated with $HDL_3$ and/or hAIBP as in 1a, followed by a 20 min stimulation with 50 ng/ml VEGF. Cells were treated with a crosslinking reagent, lysed and immunoprecipitated with a VEGFR2 antibody. Monomers and crosslinked dimers of VEGFR2 were visualized on western blot.

FIG. 17f, Effect of hAIBP and $HDL_3$ on VEGFR2 endocytosis. HUVEC were preincubated with or without 50 µg/ml $HDL_3$+0.1 µg/ml hAIBP for 4 hours, then stimulated with 50 ng/ml VEGF for 20 min, fixed and stained with antibodies to VEGFR2 (red) and the early endosome marker EEA-1 (green). Yellow and white arrows point to the surface and endosomal localization of VEGFR2. Red dotted line traces cell contour. Scale, 10 µm.

FIG. 17g, Effect of hAIBP and $HDL_3$ on VEGFR2 signaling. HUVEC were preincubated with $HDL_3$ and/or hAIBP as in 2a, followed by a 20 min stimulation with 50 ng/ml VEGF. Total cell lysates were run on SDS-PAGE and probed as indicated.

FIG. 18. Effect of Aibp deficiency on zebrafish cholesterol, membrane lipid order, Vegfr2 signaling and angiogenesis.

FIG. 18a, Tissue distribution of zaibp2 mRNA in zebrafish embryos. Embryos at 24 hpf were fixed and WISH was performed with antisense myod and zaibp2 probes. Scale, 100 µm.

FIG. 18b, Zebrafish embryos were injected with 8 ng of either control MO or zaibp2 MO. Twenty four hpf control and zaibp2 morphants were stained with filipin to detect free cholesterol in embryos. Note the yolks are artificially masked on the images. FIG. 18c, At 24 hpf, the trunk area (without yolk) was dissected, total lipids extracted, and free cholesterol levels determined by gas chromatography (GC). The cholesterol levels were normalized to the protein content and then to the values in control MO embryos. 50-70 embryos were pooled for each sample. Mean±SE; n=4; *, p<0.05.

FIG. 18d, Effect of zaibp2 MO on SeA membrane lipid order. Tg(flk1:ras-cherry)$^{s896}$ embryos were injected with control or zaibp2 MO as in 3b and at 24 hpf were stained with 5 µM Laurdan. In the same embryos, confocal images of mCherry fluorescence (bottom images) and the multiphoton images of Laurdan fluorescence (ex 800 nm, em 400-460 nm and 470-530 nm) were captured. The multiphoton results (top row images) are displayed as pseudocolored GP (generalized polarization, a measure of the membrane lipid order) images, cropped to show only the vasculature, i.e. mCherry-positive areas. Scale, 20 µm. FIG. 18e, The graph shows GP values in the areas corresponding to tip and stalk cells of growing SeA and the dorsal aorta (DA) as indicated in 3d. Some one-cell stage embryos were co-injected with 1 nl of 10 mg/ml human $HDL_3$ or BSA. Note the Y-scale is from 0.2 to 0.5. Mean±SE; n=44-119 SeA in 25-49 embryos; ***, p<0.001.

FIG. 18f, Phosphorylation of signaling proteins. Lysates of 24 hpf control (8 ng control MO), zaibp2 (8 ng zaibp2 MO) and abca1/g1 (4 ng abca1 MO+4ng abcg1 MO) morphants were separated on SDS-PAGE and immunoblotted as indicated.

FIG. 18g, Angiogenic defects in zaibp2 morphants. One-cell stage Tg(fli1:egfp)$^{y1}$ zebrafish embryos were injected with 8 ng of either control or zaibp2 MO. The images are of SeA in 30 hpf embryos (top row), and SeA (middle row) and of SIV (bottom row) in 3 dpf embryos. Arrows point to dysregulated sprouts. Scale, 25 µm. h, Quantification of the number of embryos with normal and abnormal angiogenesis (SeA with ectopic branching). The abnormal angiogenesis was partially rescued by co-injection of 40 pg of zaibp2 mRNA lacking the MO targeting site. Mean±SE; n=100-149. ***, p<0.001.

FIG. 19. Effect of Aibp and Abca1/Abcg1 deficiency on zebrafish angiogenesis.

FIG. 19a, Mosaic expression analysis of EC branching in control, zaibp2 and abca1/abcg1 knockdown embryos. At 4 hpf, cells were isolated from donor embryos and transplanted into recipient embryos. Recipient embryos were analyzed at 3 dpf. Arrows point to aberrant ectopic branches/sprouts. Scale, 25 µm. FIG. 19b, Numbers of ectopic branches/filopodial projections per SeA. Mean±SE; n=8-16. #, not significant; *, p<0.05; ***, p<0.001.

FIG. 19c, Angiogenic defects in abca1/abcg1 morphants. One-cell stage embryos were injected with 8 ng of control MO, 8 ng zaibp2 MO, or 4 ng abca1 MO+4 ng abcg1 MO. Images of SeA (30 hpf) and SIV (3 dpf) are shown. Scale, 50 µm.

FIG. 19d, Knockdown of abca1/g1 cancels the effect of zAibp2 overexpression. One-cell stage embryos were injected with 2 nl of 100 ng/µl myog:zaibp2-mCherry, myog:zaibp2-mCherry+abca1/g1 MO, or myog:mCherry. The arrow points to an aberrant SeA at the site of zAibp2-mCherry expression. Scale, 20 µm. FIG. 19e, Abnormal SeA formation was quantified in 8-16 embryos per group. Mean±SE; *** p<0.001.

Methods

Human and zebrafish AIBP were used in cholesterol efflux, angiogenesis and cellular assays as described[10,23,25]. In vivo angiogenesis was monitored in Tg(fli1:egfp)$^{y1}$ zebrafish with zaibp2 and/or abca1 and abcg1 knockdown or forced zaibp2 expression.

Cloning of Human and Zebrafish AIBP, Recombinant Protein Expression and Purification, and Antibody Production Zebrafish aibp2 and aibp1 were cloned from zebrafish brain cDNA using primers:

```
                                            (SEQ ID NO: 21)
CCGGAATTCCATGTTGGGGGTTCGAGCTCTG(5')
and
```

-continued

```
                                       (SEQ ID NO: 22)
CGCGGATCCTCAGTTGAGCTGAAACACACACTC(3')
for zaibp1; and (SEQ ID NO: 23)
CCGGAATTCCGCCACCATGAACCACAGCTCCAACG(5')
and (SEQ ID NO: 24)
CGCGGATCCCGCAGTTCTATAATACATTCTGTGC(3')
``` for zaibp2. The fragments were cloned in frame into pFLAG-CMV4 (Sigma). Human APOA1BP was cloned from HEK293 cell cDNA using primers:

```
                                       (SEQ ID NO: 25)
CCGGAATTCCATGTCCAGGCTGCGGGCGCTGCTGGGCCTCG(5')
and (SEQ ID NO: 26)
CGGGGTACCTCACTGCAGACGATAGACACACTC(3').
```

For expression of AIBP proteins, the genes were cloned in frame into pHUE vector[26] (kindly provided by Tracy Handel), expressed in BL21 DE3 competent cells (Invitrogen) and purified with a Ni-NTA agarose resin column (Qiagen). Deubiquitinase (DUB) expressed in pHUE was used as a negative control in experiments with recombinant AIBP. To produce a zAibp2 antibody, 500 µl (200 µg) of recombinant zAibp2 was mixed with 500 µl complete Freund's adjuvant (Sigma) and injected subcutaneously into a guinea pig. The guinea pig was boosted one month later with a subcutaneous injection of 200 µg antigen mixed with incomplete Freund's adjuvant (Sigma), followed by 2 more boosts (intramuscular injections of 200 µg antigen in 1 ml PBS, 2 weeks apart). Post-immune plasma was compared with pre-immune plasma from the same animal and used in western blot to detect zAibp2 in zebrafish lysates. The specificity of the antibody was confirmed by adding excess of recombinant zAibp2 to the antibody, which prevented its binding to a specific band on the western blot.

Cholesterol Efflux

A cholesterol efflux assay was performed as described[23, 27], with modifications. In brief, human umbilical vein endothelial cells (HUVEC; from ATCC) were loaded with 2 µCi/ml $^3$H-cholesterol in 5% fetal bovine serum (FBS)-supplemented EBM media (Lonza). Twenty-four hours later, cells were washed and equilibrated for 1 hour with EBM containing 0.2% bovine serum albumin (BSA). The cells were washed with PBS and cholesterol efflux was initiated by the addition of 0.2% BSA/EBM with 50 µg/ml HDL$_3$ (isolated from normolipidemic human plasma by ultracentrifugation), in the presence or absence of 0.2 µg/ml zAibp2, zAibp1, or hAIBP. Deubiquitinase (DUB), replacing AIBP, was used as a negative control. Background, non-specific release of $^3$H-cholesterol was measured in 0.2% BSA/EBM, in the absence of HDL or any other protein. After 1 to 6 hours of incubation, the medium was collected and counted in a multipurpose liquid scintillation counter LS 6500 (Beckman Coulter). The cells were extracted with 2-propanol, the lipid extract evaporated under argon gas, resuspended in 2-propanol and then added to ScintiVerse BD Cocktail (Fisher), and counted. Cholesterol efflux was expressed as a percentage of $^3$H counts in the medium compared to combined $^3$H counts in the cells and the medium. Background, non-specific release of $^3$H from the cells was subtracted.

ABCG1 Knockdown

Both negative control and ABCG1 siRNA oligonucleotides were from Ambion. HUVEC were plated in 6-well plates at 5×10$^5$ cells/well and transfected with 66.6 nM siRNA using SUPERFECT TRANSFECTION REAGENT™ (Qiagen) as described in the manufacturer's protocol. Two days after transfection, cells were washed and used in an efflux assay. Two additional wells of transfected cells were used to confirm ABCG1 knockdown in western blot using an antibody from Novus Biologicals.

AIBP/HDL$_3$—HUVEC Binding Assay hAIBP and HDL$_3$ were biotinylated with EZ-Link Sulfo-NHS-Biotin according the manufacture's protocol (Thermo Scientific). Binding of biotinylated hAIBP or biotinylated HDL$_3$ to HUVEC was assessed by a chemiluminescent binding assay as described by Fang et al.[28], with modifications. 2×10$^4$ HUVEC were seeded into 96-well flat bottom plates in 5% FBS-EBM. After 72 h, plates were washed gently 5 times with PBS using a microtiter plate washer (Dynex Technologies, Chantilly, Va.), blocked with 200 µl of ice-cold 1% BSA-PBS for 30 min on ice, incubated with ice-cold biotinylated proteins (100 µl/well) for 2 h on ice, washed, and fixed with ice-cold 4% paraformaldehyde (PFA) in PBS for 30 min. HUVEC-bound biotinylated hAIBP or HDL$_3$ were detected with NeutrAvidin-conjugated alkaline phosphatase (Pierce) and LUMIPHOS 530™ (Lumigen, Southfield, Mich.), using a DYNEX™ luminometer (Dynex Technologies). Data were recorded as relative light units counted per 100 ms. All samples were assayed in triplicates. The parameters of hAIBP and HDL$_3$ bindings to HUVEC ($B_{max}$ and $K_d$) were calculated using a total and non-specific binding algorithm within the GRAPHPAD PRISM 5.0™ software package. The following model was used: H+C↔HC, where H is unbound HDL$_3$, C is cells, and HC is HDL$_3$ bound to the cells. The equations used for calculating binding parameters were:

$$[HC]_{specific}=B_{max}\times[H]/([H]+K_d)$$

$$[HC]_{nonspecific}=a+b\times[H]$$

$$[HC]_{total}[HC]_{specific}+[HC]_{nonspecific},$$

where a is background and b is the slope of the linear fit of nonspecific binding. Goodness of fit of non-linear regression was estimated using $R^2$ and standard deviation of residuals (Sy.x), expressed in the same units as [H] and $B_{max}$. A molecular mass of 80 kDa was used for the HDL protein (2 molecules of ApoA-I, comprising 70% of the HDL protein mass).

In Vitro Angiogenesis Assay

The angiogenesis assay was carried out as described in reference[29]. Growth factor reduced Matrigel (BD Biosciences) was thawed at 4° C. overnight and diluted with an equal volume of serum-free EBM medium (Lonza). Each well of pre-chilled 96-well plates was coated with 50 µl diluted Matrigel and incubated at 37° C. for 1 hour. HUVEC were serum-starved and then pre-incubated for 4 hours with 50 µg/ml HLD$_3$, 0.1 µg/ml hAIBP, or 50 µg/ml HLD$_3$+0.1 µg/ml hAIBP. Cells were harvested and added to Matrigel-coated plates at 1×10$^4$ cells per well in EBM, in the presence or absence of 20 ng/ml VEGF (R&D Systems). Tubular structures were imaged following a 12 hour incubation with a phase contrast microscope.

Free Cholesterol Measurements in HUVEC

HUVEC cholesterol levels were measured in cellular lipid extracts using a colorimetric assay (BioVision) and manufacturer's protocol as described[14]. Because in HUVEC non-esterified, free cholesterol comprises more than 95% of total cholesterol[14] and because free cholesterol is the form of cholesterol that is transferred from the cells via ABC transporters to ApoA-I/HDL, we only measured free cholesterol in these experiments.

Aortic Ring Neovascularization Assay

The method was adopted from reference[30], with modifications. Thoracic aorta was isolated from a 6-week old male C57BL6 mouse or an age and gender matched Abcg1$^{-/-}$ mouse (kindly provided by Catherine Hedrick, La Jolla Institute for Allergy and Immunology), cleaned from surrounding fat and connective tissue and sliced into 1 mm long rings. The aortic rings were placed in wells of a 48-well plate containing solidified Matrigel and then covered with additional Matrigel and let it solidify for 30 min at 37° C. Small wells were made in Matrigel approximately 0.5 mm from aortic rings and 50 µl aliquots of Matrigel containing 1×10$^5$ HEK293 cells transfected with mCherry (negative control), zAIBP2 or hAIBP were placed in these wells. After 10 min, each well was filled with EBM medium supplemented with 10 ng/ml VEGF and the plates were incubated at 37° C. for 6 days. Media were changed every two days. The rings were photographed in phase contrast using a Nikon Eclipse Ti microscope.

Visualization of Lipid Rafts with Cholera Toxin B

HUVEC were plated on glass coverslips and preincubated with 50 µg/ml HDL$_3$, 0.1 µg/ml hAIBP, or 50 µg/ml HDL$_3$+ 0.1 µg/ml hAIBP for 4 hours. Cells were washed once with medium before the addition of 1 µg/ml Alexa Fluor 594-labeled cholera toxin B (CTB, from Invitrogen). Cells were incubated for 15 min at 4° C., washed with PBS, and then incubated for 15 min at 4° C. with an anti-CTB antibody (EMD Chemicals) to crosslink CTB and lipid rafts. After washing with PBS, cells were fixed in 4% PFA for 20 min at 4° C., mounted with a PROLONG ANTIFADE KIT with DAPI (Invitrogen/Life Technologies) and images were captured with a Leica DM IRE2™ fluorescent microscope.

Cell Fractionation

Lipid rafts (light membrane fractions) were isolated using a detergent-free, discontinuous gradient ultracentrifugation method[14]. Briefly, HUVEC were washed twice with ice cold PBS and cells were scraped from the plate in 0.5 M sodium carbonate buffer (pH 11.0) containing a protease inhibitor cocktail (Sigma), homogenized and sonicated 3×10 sec. Samples were adjusted to 45% sucrose by adding a 90% sucrose solution in MBS (25 mM Mes, 0.15 M NaCl, pH 6.5) and placed into ultracentrifugation tubes. A 5-35% sucrose discontinuous gradient was formed above the sample, followed by ultracentrifugation at 35×10$^3$ rpm for 18 hours at 4° C. in a SW-41 rotor (Beckman). Ten 1 ml fractions were collected from the top to the bottom of each gradient. The lipid rafts fraction (fraction 5) and the non-lipid rafts fraction (fraction 10) were used for further analysis, which included measurements of protein concentration and immunoblotting. Thirty µl of lipid rafts and non-lipid rafts fractions (adjusted to load equal protein concentrations of each sample) were run on SDS-PAGE, transferred to PVDF membranes and blotted with the indicated antibodies.

Caveolin-1 and VEGFR2 Colocalization

HUVEC plated on chamber coverglass (LAB-TEK II™) were incubated for 4 hours with 0.1 µg/ml hAIBP, 50 µg/ml HDL$_3$ or 0.1 µg/ml hAIBP+50 µg/ml HDL$_3$, and then cells were washed with PBS and fixed with warm 4% PFA for 15 min at room temperature. HUVEC were permeabilized with PBS containing 0.3% Triton X-100 (PBST) for 10 min, blocked with PBST containing 1% BSA and 5% normal goat serum for 1 hour at room temperature, incubated with anti-Caveolin-1 (BD Biosciences) and anti-VEGFR2 (Cell Signaling Technology) antibodies overnight at 4° C., followed by incubation with anti-mouse IgG-Alexa Fluor 488 and anti-rabbit IgG-Cy3 antibodies for 2 hours. Images were captured using a Nikon Eclipse Ti inverted fluorescent microscope operating in TIRF mode. Raw Tiff images of Caveolin-1 and VEGFR2 were analyzed using JACoP algorithm[31]. Colocalization was quantified using Pearson's coefficient. The JACoP plugin was loaded to ImageJ as described[31].

VEGFR2 Endocytosis

HUVEC were incubated for 4 hours with 0.1 µg/ml hAIBP, 50 µg/ml HDL$_3$ or 0.1 µg/ml hAIBP+50 µg/ml HDL$_3$, followed by a 20 min incubation with 50 ng/ml VEGF. Cells were fixed and stained with antibodies against VEGFR2 and the early endosomal marker EEA-1-FITC (BD Biosciences). Images were captured with a Nikon Eclipse Ti inverted fluorescent microscope. VEGFR2 and EEA-1 colocalization was quantified using Pearson's coefficient with the JACoP plugin loaded to ImageJ[31].

VEGFR2 Dimerization Assay

The assay was carried out as described in reference[32]. Two days after plating 1×10$^6$ HUVEC in a 10 cm dish, the cells were starved overnight in 0.5% FBS-EBM. Next day, cells were incubated for 4 hours with 0.2 µg/ml hAIBP, 50 µg/ml HDL$_3$ or 0.2 µg/ml hAIBP+50 µg/ml HDL$_3$ in EBM containing 0.2% BSA, followed by a 20 min incubation with 50 ng/ml VEGF and then crosslinked with 1 mg/ml bis-sulfosuccinimidyl (Thermo Scientific) for 30 min on ice. Cell lysates were immunoprecipitated with an anti-VEGFR2 antibody (Cell Signaling Technology) immobilized on agarose beads. The beads were washed and the eluted samples were run on SDS-PAGE, followed by immunoblotting with the VEGFR2 antibody.

HUVEC Migration Assay

Serum starved HUVEC were pretreated with 50 µg/ml HDL$_3$, 0.2 µg/ml hAIBP, or 50 µg/ml HDL$_3$+0.2 µg/ml hAIBP for 4 hours at 37° C. in 5% LPDS/EBM, harvested from the plate, washed, resuspended in 5% LPDS/EBM and added to the transwell (8 µm pore size). VEGF was added to the lower chamber at 20 ng/ml. Following a 4 hour incubation, the transwell membranes were fixed in ice-cold methanol for 10 min and stained with filtered 0.5% Crystal Violet for 10 min, and transmigrated cells were counted.

Zebrafish

Wild type AB and transgenic Tg(fli1:egfp)$^{y1}$ and Tg(flk1:ras-cherry)$^{s896}$ zebrafish lines[19,33] were kindly provided by Dr. David Traver and Neil Chi (UCSD). Zebrafish were maintained as previously described[34], and all experimental procedures were approved by the UCSD IACUC.

Confocal Microscopy

Confocal imaging was carried out as previously described[35]. Briefly, anaesthetized zebrafish embryos (treated at 24 hpf with 0.003% PTU) were housed in a sealed chamber (Invitrogen) in a small drop of 0.02% tricaine (Sigma) containing E3 medium. A Nikon C1-si confocal microscope was used in a one- or two-channel mode to detect fluorescence of one or two fluorophores in the same embryo. In the green channel, excitation was 488 nm for EGFP, and in the red channel, 561 nm for mCherry or DsRed. Z-stacks were acquired with a 1-3 µm step, and images were 3D rendered and analyzed using IMARIS® software (Bitplane). All 3D reconstructions were performed with the same threshold settings.

Morpholino Oligonucleotide Injections

To knock down gene expression, 4-8 ng of morpholino antisense oligonucleotides (MO; synthesized by GeneTools) were injected into one-cell stage embryos. A control MO was derived
from the zaibp2 sequence, with 5 mismatched oligonucleotides.

```
Control MO:
                              (SEQ ID NO: 27)
TGAGCTTCATGTTCATTTATTCCGC;

zaibp2 MO (zaibp2 MO1):
                              (SEQ ID NO: 28)
TGTGGTTCATCTTGATTTATTCGGC;

zaibp2 splicing MO (zaibp2 MO2):
                              (SEQ ID NO: 29)
TGTTGAGTGTCAGACAAACCTTGGT zaibp1 MO:
                              (SEQ ID NO: 30)
TCTGTATTCAAATCAGACGCTCAGT;

abca1 MO:
                              (SEQ ID NO: 31)
AACCCAACTGAGTGGAGACAGCCAT;

abcg1 MO:
                              (SEQ ID NO: 32)
AAAAGGCTGCCATGAGACATGCCAT.
```

Quantitative Analysis of Cell Sprouts in Segmental Arteries (SeA) and Subintestinal Veins (SIV)

To determine changes in segmental artery cell sprouts in embryos injected with MO targeting zaibp2, zaibp1, abca1 and/or abcg1, we counted abnormal projections in 4 to 6 pairs of segmental arteries in adjacent somite boundaries in each zebrafish. For each set of injections, 15 embryos (i.e. 60-90 sprouts) were examined. Values were expressed as a number of ectopic sprouts per SeA. To examine sprouts in SIV, only the sprouts moving in the ventral direction out of the SIV were counted. Values were expressed as a number of ventral SIV sprouts per zebrafish.

Measuring Membrane Lipid Order with Polarity-Sensitive Probe

The experiments were carried out as described in reference[36,37]. Briefly, live Tg(flk1:ras-cherry)$^{s896}$ zebrafish embryos were incubated with 5 µM Laurdan (Invitrogen) at 28° C. for 30 min. The concentration of a Laurdan stock solution was measured using OD at 365 nm and an extinction coefficient of 19000 cm$^{-1}$M$^{-1}$. After incubation with Laurdan, embryos were incubated with E3 medium for additional 30 min, fixed in PFA for 4 hours at room temperature, deyolked, and embedded in 1% low melting temperature agarose for imaging. Images were captured with a Leica SP5 confocal/multiphoton system, using a water immersion 20× objective. The confocal mode was used to capture mCherry fluorescence and the multiphoton mode was used to capture Laurdan images (ex 800 nm, em 400-460 nm and 470-530 nm) in the same embryos. The multiphoton results were displayed as pseudocolored GP (a measure of the membrane lipid order) images, derived from Laurdan ratiometric measurements and using a ImageJ plug-in as described[36]. The quantitative data were obtained by measuring GP values in the areas corresponding to tip cells (top 1/3 of the SeA length), stalk cells (bottom 2/3 of the SeA length) and the dorsal aorta in several individual, mCherry-masked z-sections. This method ensured that GP values were derived only from EC (e.g. from the areas where mCherry was in focus in each z-section). The GP images in FIG. 3e were composed each from four to five individual z-sections, with a minimal overlap of mCherry-masked GP images.

Whole Mount In Situ Hybridization

WISH was carried out as described[38-40]. Briefly, WT embryos or morphants at indicated developmental stages were fixed with 4% PFA and the embryos older than 24 hpf were permeabilized with 10 µg/ml protease K (Roche). Subsequently, the embryos were pre-hybridized at 70° C. for 4-6 hours, and then hybridized with a digoxigenin-labeled zaibp2 antisense probe at 65° C. for 2 days. Both the control sense and anti-sense RNA probes were directly synthesized from zaibp2 full length gene using a Roche T7/SP6 RNA or Ambion T3 RNA synthesis kit. After extensive wash, hybridized RNA was detected by immunohistochemistry using an alkaline phosphatase-conjugated antibody against digoxigenin (Roche) and a chromogenic substrate nitro blue tetrazolium (NBT) (Sigma) and 5-bromo-4-chloro-3-indolyl phosphate (BCIP)[38] (Sigma). A similar procedure was performed with tie2, vegfr2, vegfr3, fli1 and cdh5 probes. Double WISH were performed as described[41]. All the procedures were the same with the aforementioned one except that both digoxigenin-labeled zaibp2 and fluorescein-labeled myod were hybridized with the embryos. The embryos were then first incubated with alkaline phosphatase-conjugated anti-fluorescein Ab, and fast red (Roche) was used as a substrate. Subsequently, the embryos were washed, fixed with 4% PFA and incubated with anti-digoxigenin Ab conjugated alkaline phosphatase, and then NBT/BCIP was used as a chromogenic substrate.

Transplantation Experiments

Cell transplantation was performed as described[39], with different combinations of donors and recipients as indicated in FIG. 4a. Donor embryos were of the Tg(fli1:egfp)$^{y1}$ origin, and recipient embryos were of the wild type origin. At the one-cell stage, donor Tg(fli1:egfp)$^{y1}$ embryos were injected with rhodamine-labeled dextran (Mini-Ruby, Invitrogen) as a lineage tracer. At the sphere stage (approximately 4 hpf), embryos were dechorionated by 0.4 mg/ml pronase (Sigma) and transferred to agarose wells (Adaptive Science Tools, Worcester, Mass.). Approximately 20-40 cells from the margin of a donor embryo were transferred to the margin of a recipient embryo. The recipient embryos were subsequently grown at 28° C. and imaged at 72 hpf. Endothelial cells in chimeric zebrafish originating from donor embryos were visualized by their green fluorescence using a Leica M165FC fluorescent stereoscope. For detailed analysis, images were captured using a Nikon C1-si confocal microscope. Numbers of ectopic branches in each fluorescent SeA were counted.

Microarray

Fifty control MO or zaibp2 MO embryos at 12 hpf were dechorionated, and total RNA was extracted with a Qiagen's RNeasy Kit, with modifications. In brief, dechorionated embryos were immediately placed in RNAlater (Qiagen), and incubated for 10 min at room temperature. The embryos were then homogenized in Trizol (Invitrogen) for 30-60 seconds on ice, chloroform was added and the sample was vortexed for 30 sec, incubated for 5 min at room temperature and centrifuged for 30 min at 13,000 rpm at 4° C. The upper layer was transferred to a new tube, supplemented with 70% ethanol and mixed thoroughly. The sample was then processed according to the RNeasy kit manual. The microarray analysis was performed at UCSD's Biogem Core facility using a Zebrafish (V3) Gene Expression Microarray, 4×44 k, Cat# G2519F-026437 from Agilent.

Real Time PCR

Real time PCR was performed using a Rotor Gene Q qPCR machine (Qiagen). Real time PCR master mix Platinum SYBR Green qPCR SUPERMIX was from Invitrogen (Life Technologies). The primers were synthesized by IDT. The PCR program was: 50° C. for 2 minutes (UDG incubation), 95° C. for 2 minutes, 40 cycles of: 95° C. for 15 seconds, 60° C. for 1 minute. Primer sequences:

```
fli1 (F):
                              (SEQ ID NO: 33)
CTTGGCACGTTGCCTTGATAAG, fli1 (R):
                              (SEQ ID NO: 34)
CCTTCATATCTGAGAGTGATCCC;

tie2 (F):
                              (SEQ ID NO: 35)
GCGATGGATGGCAATAGAGT, tie2 (R):
                              (SEQ ID NO: 36)
CGACAGCAGGATCTGAGAGA;

vegfr2 (F):
                              (SEQ ID NO: 37)
TCCACGAGGGTGGGCAGTCA;

vegfr2 (R):
                              (SEQ ID NO: 38)
AGACGGGTGGTGTGGAGTAACGA.

kdrb (F):
                              (SEQ ID NO: 39)
TGCCCACATGGAGCTGCTAGCA;

kdrb (R):
                              (SEQ ID NO: 40)
TGTGGCACATTCAACCACATGAGC.

β-actin (F):
                              (SEQ ID NO: 41)
CTCTTCCAGCCTTCCTTCCT, β-actin (R):
                              (SEQ ID NO: 42)
GGTTGGTTCGTTCGTTTGAAT.
```

Immunoblot of Zebrafish Lysates

Zebrafish were lysed on ice with a lysis buffer (50 mM Tris-HCl, pH 7.5, 4 mM sodium deoxycholate, 1% Triton X 100, 150 mM NaCl, 1 mM EDTA, and protease inhibitor cocktail from Sigma). Protein content was determined with a DC protein assay kit (BioRad) and equal protein amounts of the cell lysates were run on a 4-12% Bis-Tris SDS-PAGE with MOPS buffer (Invitrogen) and then transferred to a PVDF membrane (Invitrogen). The blots were probed with appropriate antibodies against specific phosphorylated and non-phosphorylated proteins (Cell Signaling Technology), secondary antibodies conjugated with HRP and developed using a Super Signal West Dura substrate (Pierce).

Filipin Staining

Filipin staining of embryos was performed as described[42]. Zebrafish were fixed with 4% PFA overnight at 4° C. The fixed fish were incubated overnight with 0.05% filipin (Sigma) in PBS with 1% sheep serum, and then washed 3 times with PBS. Images were captured immediately with a Leica M165FC fluorescent stereoscope and quantified.

Total Lipid Extraction and Free Cholesterol Measurements in Zebrafish

Total lipid was extracted from zebrafish embryos as we previously described[28]. In brief, trunk/tail segments were dissected from fifty 24 hpf embryos and pooled together. The tissue was homogenized and supplemented with 50 µg stigmasterol, an internal standard to control for recovery of extracted sterols. Total lipid extraction was performed with 1:2 methanol/dichloromethane. No saponification of cholesterol esters was performed because the goal of this study was to measure free cholesterol, the form of cholesterol transferred from the cells via ABC transporters to ApoA-I/HDL. Cholesterol and stigmasterol were measured with a Shimadzu GC-2014 gas chromatograph using a 30 m×0.25 mm (i.d.) ZB-5HT inferno capillary column, film thickness 0.2 µm (Phenomenex). Cholesterol levels were normalized to protein and then to the levels in embryos injected with control MO.

REFERENCES—EXAMPLE 2

1. Klucken, J., et al. ABCG1 (ABC8). the human homolog of the *Drosophila* white gene, is a regulator of macrophage cholesterol and phospholipid transport. *Proc Natl Acad Sci USA* 97, 817-822 (2000).
2. Orso, E., et al. Transport of lipids from Golgi to plasma membrane is defective in tangier disease patients and Abc1-deficient mice. *Nat Genet* 24, 192-196 (2000).
3. Rust, S., et al. Tangier disease is caused by mutations in the gene encoding ATP-binding cassette transporter 1. *Nat Genet* 22, 352-355 (1999).
4. Yvan-Charvet, L., et al. ATP-Binding Cassette Transporters and HDL Suppress Hematopoietic Stem Cell Proliferation. *Science* 328, 1689-1693 (2010).
5. Armstrong, A. J., Gebre, A. K., Parks, J. S. & Hedrick, C. C. ATP-Binding Cassette Transporter G1 Negatively Regulates Thymocyte and Peripheral Lymphocyte Proliferation. *The Journal of Immunology* 184, 173-183 (2009).
6. Bensinger, S. J., et al. LXR Signaling Couples Sterol Metabolism to Proliferation in the Acquired Immune Response. *Cell* 134, 97-111 (2008).
7. Ritter, M., et al. Cloning and characterization of a novel apolipoprotein A-I binding protein, AI-BP, secreted by cells of the kidney proximal tubules in response to HDL or ApoA-I. *Genomics* 79, 693-702 (2002).
8. Bodnar, J. S., et al. Positional cloning of the combined hyperlipidemia gene Hyplip1. *Nat Genet* 30, 110-116 (2002).
9. Jha, K. N., et al. Biochemical and structural characterization of apolipoprotein A-I binding protein, a novel phosphoprotein with a potential role in sperm capacitation. *Endocrinology* 149, 2108-2120 (2008).
10. O'Connell, B. J. Cellular Physiology of Cholesterol Efflux in Vascular Endothelial Cells. *Circulation* 110, 2881-2888 (2004).
11. Terasaka, N., et al. ABCG1 and HDL protect against endothelial dysfunction in mice fed a high-cholesterol diet. *Journal of Clinical Investigation* 118, 3701-3713 (2008).
12. Mendez, A. J., Lin, G., Wade, D. P., Lawn, R. M. & Oram, J. F. Membrane lipid domains distinct from cholesterol/sphingomyelin-rich rafts are involved in the ABCA1-mediated lipid secretory pathway. *J Biol Chem* 276, 3158-3166 (2001).
13. Simons, K. & Ikonen, E. Functional rafts in cell membranes. *Nature* 387, 569-572 (1997).
14. Paila, Y. D. & Chattopadhyay, A. Membrane cholesterol in the function and organization of Gprotein coupled receptors, *Subcell Biochem* 51, 439-466 (2010).

15. Lawson, N. D. & Weinstein, B. M. In vivo imaging of embryonic vascular development using transgenic zebrafish. *Dev Biol* 248, 307-318 (2002).
16. Gu, C. Semaphorin 3E and Plexin-D1 Control Vascular Pattern Independently of Neuropilins. *Science* 307, 265-268 (2005).
17. Torres-Vázauez, J., et al. Semaphorin-Plexin Signaling Guides Patterning of the Developing Vasculature. *Developmental Cell* 7, 117-123 (2004).
18. Futter, M., et al. Wild-type but not mutant huntingtin modulates the transcriptional activity of liver X receptors. *J Med Genet* 46, 438-446 (2009).
19. Thisse, B., Pfumio, S., Fürthauer, M., Loppin B., Heyer, V., Dearave, A., Woehl, R., Lux, A., Steffan, T., Charbonnier, X. Q, and Thisse, C., Expression of the zebrafish genome during embryogenesis (NIH R01 RR15402). *ZFIN Direct Data Submission* (http://zfin.org) (2001).
20. Ruch, C., Skiniotis, G., Steinmetz, M. O., Walz, T. & Ballmer-Hofer, K. Structure of a VEGFVEGF receptor complex determined by electron microscopy. *Nat Struct Mol Biol* 14, 249-250 (2007).
21. Lawson, N. D. & Weinstein, B. M. Arteries and veins: making a difference with zebrafish. *Nat Rev Genet* 3, 674-682 (2002).
22. Adams, R. H. & Alitalo, K. Molecular regulation of angiogenesis and lymphangiogenesis. *Nat Rev Mol Cell Biol* 8, 464-478 (2007).
23. Herbert, S. P. & Stainier, D. Y. Molecular control of endothelial cell behaviour during blood vessel morphogenesis. *Nat Rev Mol Cell Biol* 12, 551-564 (2011).
24. Whetzel, A. M., et al. ABCG1 Deficiency in Mice Promotes Endothelial Activation and Monocyte-Endothelial Interactions. *Arteriosclerosis, Thrombosis, and Vascular Biology* 30, 809-817 (2010).
25. Kureishi, Y., et al. The HMG-CoA reductase inhibitor simvastatin activates the protein kinase Akt and promotes angiogenesis in normocholesterolemic animals. *Nature medicine* 6, 1004-1010 (2000).
26. Choi, J., et al. Aplexone targets the HMG-CoA reductase pathway and differentially regulates arteriovenous angiogenesis. *Development* 138, 1173-1181 (2011).
27. Aplin, A. C., Gelati, M., Fogel, E., Carnevale, E. & Nicosia, R. F. Angiopoietin-1 and vascular endothelial growth factor induce expression of inflammatory cytokines before angiogenesis. *Physiol Genomics* 27, 20-28 (2006).
28. Skawran, B., et al. Gene expression profiling in hepatocellular carcinoma: upregulation of genes in amplified chromosome regions. *Mod Pathol* 21, 505-516 (2008).
29. Lenburg, M. E., et al. Previously unidentified changes in renal cell carcinoma gene expression identified by parametric analysis of microarray data. *BMC Cancer* 3, 31 (2003).
30. Carmona, G., et al. Role of the small GTPase Rap1 for integrin activity regulation in endothelial cells and angiogenesis. *Blood* 113, 488-497 (2009).

REFERENCES—EXAMPLE 3

1. Bodzioch, M. et al. The gene encoding ATP-binding cassette transporter 1 is mutated in Tangier disease. *Nat Genet* 22, 347-351 (1999).
2. Rust, S. et al. Tangier disease is caused by mutations in the gene encoding ATP-binding cassette transporter 1. *Nat Genet* 22, 352-355 (1999).
3. Klucken, J. et al. ABCG1 (ABC8), the human homolog of the *Drosophila* white gene, is a regulator of macrophage cholesterol and phospholipid transport. *Proc Natl Acad. Sci USA* 97, 817-822 (2000).
4. Yvan-Charvet, L. et al. ATP-Binding Cassette Transporters and HDL Suppress Hematopoietic Stem Cell Proliferation. *Science* 328, 1689-1693 (2010).
5. Armstrong, A. J., Gebre, A. K., Parks, J. S. & Hedrick, C. C. ATP-binding cassette transporter G1 negatively regulates thymocyte and peripheral lymphocyte proliferation. *J Immunol* 184, 173-183 (2010).
6. Bensinger, S. J. et al. LXR signaling couples sterol metabolism to proliferation in the acquired immune response. *Cell* 134, 97-111 (2008).
7. Ritter, M. et al. Cloning and Characterization of a Novel Apolipoprotein A-I Binding Protein, AI-BP, Secreted by Cells of the Kidney Proximal Tubules in Response to HDL or ApoA-I. *Genomics* 79, 693-702 (2002).
8. Jha, K. N. et al. Biochemical and Structural Characterization of Apolipoprotein A-I Binding Protein, a Novel Phosphoprotein with a Potential Role in Sperm Capacitation. *Endocrinology* 149, 2108-2120 (2008).
9. Stefulj, J. et al. Human Endothelial Cells of the Placental Barrier Efficiently Deliver Cholesterol to the Fetal Circulation via ABCA1 and ABCG1. *Circ Res* 104, 600-608 (2009).
10. Terasaka, N. et al. ABCG1 and HDL protect against endothelial dysfunction in mice fed a high-cholesterol diet. *J Clin Invest* 118, 3701-3713 (2008).
11. Fessler, M. B. & Parks, J. S. Intracellular lipid flux and membrane microdomains as organizing principles in inflammatory cell signaling. *J Immunol* 187, 1529-1535 (2011).
12. Mendez, A. J. et al. Membrane Lipid Domains Distinct from Cholesterol/Sphingomyelin-Rich Rafts Are Involved in the ABCA1-mediated Lipid Secretory Pathway. *J Biol Chem* 276, 3158-3166 (2001).
13. Murphy, A. J. et al. High-Density Lipoprotein Reduces the Human Monocyte Inflammatory Response. *Arterioscler Thromb Vasc Biol* 28, 2071-2077 (2008).
14. Noghero, A. et al. Liver X Receptor Activation Reduces Angiogenesis by Impairing Lipid Raft Localization and Signaling of Vascular Endothelial Growth Factor Receptor-2. *Arterioscler Thromb Vasc Biol* 32, 2280-2288 (2012).
15. Oshikawa, J. et al. Novel role of p66Shc in ROS-dependent VEGF signaling and angiogenesis in endothelial cells. *Am J Physiol Heart Circ Physiol* 302, H724-H732 (2012).
16. Ikeda, S. et al. Novel Role of ARF6 in Vascular Endothelial Growth Factor-Induced Signaling and Angiogenesis. *Circ Res* 96, 467-475 (2005).
17. Liao, W. x. et al. Compartmentalizing VEGF-Induced ERK2/1 Signaling in Placental Artery Endothelial Cell Caveolae: A Paradoxical Role of Caveolin-1 in Placental Angiogenesis in Vitro. *Mol Endocrinol* 23, 1428-1444 (2009).
18. Eichmann, A. & Simons, M. VEGF signaling inside vascular endothelial cells and beyond. *Curr Opin Cell Biol* 24, 188-193 (2012).
19. Lawson, N. D. & Weinstein, B. M. In Vivo Imaging of Embryonic Vascular Development Using Transgenic Zebrafish. *Dev Biol* 248, 307-318 (2002).
20. Torres-Vazquez, J. et al. Semaphorin-plexin signaling guides patterning of the developing vasculature. *Dev Cell* 7, 117-123 (2004).
21. Dean, M. & Annilo, T. Evolution of the ATP-binding cassette (ABC) transporter superfamily in vertebrates. *Ann Rev Genomics Hum Genet* 6, 123-142 (2005).

22. Archer, A. et al. Transcriptional activity and developmental expression of liver X receptor (lxr) in Zebrafish. *Dev Dyn* 237, 1090-1098 (2008).
23. Whetzel, A. M. et al. ABCG1 Deficiency in Mice Promotes Endothelial Activation and Monocyte-Endothelial Interactions. *Arterioscler Thromb Vasc Biol* 30, 809-817 (2010).
24. Avraham-Davidi, I. et al. ApoB-containing lipoproteins regulate angiogenesis by modulating expression of VEGF receptor 1. *Nat Med* 18, 967-973 (2012).
25. Carmona, G. et al. Role of the small GTPase Rap1 for integrin activity regulation in endothelial cells and angiogenesis. *Blood* 113, 488-497 (2009).
26. Catanzariti, A. M., Soboleva, T. A., Jans, D. A., Board, P. G. & Baker, R. T. An efficient system for high-level expression and easy purification of authentic recombinant proteins. *Protein Sci* 13, 1331-1339 (2004).
27. O'Connell, B. J. Cellular Physiology of Cholesterol Efflux in Vascular Endothelial Cells. *Circulation* 110, 2881-2888 (2004).
28. Fang, L., et al. Oxidized cholesteryl esters and phospholipids in zebrafish larvae fed a high cholesterol diet: macrophage binding and activation. *J Biol Chem* 285, 32343-32351 (2010).
29. Gao, F., et al. L-5F, an apolipoprotein A-I mimetic, inhibits tumor angiogenesis by suppressing VEGF/basic FGF signaling pathways. *Integr Biol (Camb)* 3, 479-489 (2011).
30. Bellacen, K. & Lewis, E. C. Aortic ring assay. *J Vis Exp* (2009).
31. Bolte, S. & Cordelieres, F. P. A guided tour into subcellular colocalization analysis in light microscopy. *J Microsc* 224, 213-232 (2006).
32. Chung, T. W., et al. Ganglioside GM3 inhibits VEGF/VEGFR-2-mediated angiogenesis: direct interaction of GM3 with VEGFR-2. *Glycobiology* 19, 229-239 (2009).
33. Chi, N.C., et al. Foxn4 directly regulates tbx2b expression and atrioventricular canal formation. *Genes Dev* 22, 734-739 (2008).
34. Westerfield, M. *The Zebrafish Book*, (University of Oregon Press, Eugene, Oreg., 2007).
35. Stoletov, K., et al. Vascular lipid accumulation, lipoprotein oxidation, and macrophage lipid uptake in hypercholesterolemic zebrafish. *Circ Res* 104, 952-960 (2009).
36. Owen, D. M., Rentero, C., Magenau, A., Abu-Siniyeh, A. & Gaus, K. Quantitative imaging of membrane lipid order in cells and organisms. *Nature protocols* 7, 24-35 (2012).
37. Gaus, K., Le Lay, S., Balasubramanian, N. & Schwartz, M. A. Integrin-mediated adhesion regulates membrane order. *J Cell Biol* 174, 725-734 (2006).
38. Thisse, C. & Thisse, B. High-resolution in situ hybridization to whole-mount zebrafish embryos. *Nat Protoc* 3, 59-69 (2008).
39. Siekmann, A. F. & Lawson, N. D. Notch signalling limits angiogenic cell behaviour in developing zebrafish arteries. *Nature* 445, 781-784 (2007).
40. Lawson, N. D., et al. Notch signaling is required for arterial-venous differentiation during embryonic vascular development. *Development* 128, 3675-3683 (2001).
41. Jowett, T. Analysis of protein and gene expression. *Methods Cell Biol* 59, 63-85 (1999).
42. Schwend, T., Loucks, E. J., Snyder, D. & Ahlgren, S. C. Requirement of Npc1 and availability of cholesterol for early embryonic cell movements in zebrafish. *Journal of lipid research* 52, 1328-1344 (2011).

Example 4: Exemplary Compounds and Methods of the Invention are Effective for Treating or Ameliorating Cancer or Tumors This example describes and demonstrates exemplary activities, and the efficacy, of compounds and methods of the invention; and in particular describes and demonstrates that compounds and methods of the invention can inhibit or slow or reverse the growth of a vascularized tumor, dysplastic tissue, tissue or growth, or cancer, using a method comprising administering to an individual an effective amount of a APOA1BP activity increasing formulation or an APOA1BP activity-increasing pharmaceutical composition of the invention.

FIG. 1 (Example 4) shows the tumor growth in mice injected with B16 melanoma cells. After tumor initiation, one group of mice received intravenous injections of recombinant human AIBP and the other group received injections of a control protein. AIBP inhibited tumor growth.

FIG. 2 (Example 4) shows the white blood cell differential in mice fed a high-fed diet (HFD) for 4 weeks. It has been documented that the HFD induces myeloid cell (monocytes and neutrophils) proliferation, reflective of an inflammatory status of hyperlipidemic animals. Injections of human AIBP but not of a control protein reversed myelocytosis in these animals.

These results demonstrate that AIBP selectively inhibit proliferation of myeloid progenitor cells, and thus can be used for treatment of dysplastic tissue, tissue or growth, or cancer, including myeloid cell proliferation in patients with cardiovascular disease, diabetes and in the aging population, as well as for treatment of myeloproliferative disease.

While data described herein links the therapeutic effects of AIBP on angiogenesis and cancer and myeloproliferative conditions (FIGS. 1 and 2, Example 4) to its ability to promote cholesterol removal from endothelial cells, tumor and/or tumor-associated cells, and myeloid progenitor cells, respectively, the invention is not limited by any particular mechanism of action.

A number of embodiments of the invention have been described. Nevertheless, it will be understood that various modifications may be made without departing from the spirit and scope of the invention. Accordingly, other embodiments are within the scope of the following claims.

What is claimed is:

1. A method for treating, reversing, preventing or downregulating an inflammatory response associated with hyperlipidemia, comprising administering to an individual an effective amount of: an ApoA-I Binding Protein (APOA1BP, AIBP, or AI-BP) polypeptide or a pharmaceutical composition comprising an ApoA-I Binding Protein (APOA1BP, AIBP, or AI-BP) polypeptide,
wherein the ApoA-I Binding Protein (APOA1BP, AIBP, or AI-BP) polypeptide comprises a sequence as set forth in SEQ ID NO:43, SEQ ID NO:44 or SEQ ID NO:45.

2. The method of claim 1, wherein the APOA1BP polypeptide comprises a sequence as set forth in SEQ ID NO:43.

3. The method of claim 1, wherein the APOA1BP polypeptide is: a recombinant, a peptidomimetic or a synthetic APOA1 BP.

4. The method of claim 1, wherein the administration is in vitro, ex vivo or in vivo.

5. The method of claim 1, wherein the ApoA-I Binding Protein is formulated for administration in vivo.

6. The method of claim 1, wherein the APOA1BP polypeptide comprises a sequence as set forth in SEQ ID NO:44.

7. The method of claim 1, wherein the APOA1BP polypeptide comprises a sequence as set forth in SEQ ID NO:45.

8. The method of claim 1, wherein the individual is a human.

9. The method of claim 1, wherein the ApoA-I Binding Protein is formulated for enteral or parenteral administration.

10. The method of claim 1, wherein the ApoA-I Binding Protein is formulated as a liposome, a tablet, a pill, a capsule, a gel, a geltab, a liquid, a powder, an emulsion, a lotion, an aerosol, a spray, a lozenge, an aqueous or a sterile or an injectable solution, or an implant.

* * * * *